(12) United States Patent
Laufer et al.

(10) Patent No.: US 11,566,290 B2
(45) Date of Patent: Jan. 31, 2023

(54) PURIFICATION OF RNA FRACTIONS USING A HYDROPHILIC POLYMERIC MATERIAL

(71) Applicant: Hummingbird Diagnostics GmbH, Heidelberg (DE)

(72) Inventors: Thomas Laufer, Edingen-Neckarhausen (DE); Markus Beier, Weinheim (DE); Mustafa Kahraman, Saarbrucken (DE); Andreas Keller, Puttlingen (DE)

(73) Assignee: Hummingbird Diagnostics GmbH, Heidelberg (DE)

( * ) Notice: Subject to any disclaimer, the term of this patent is extended or adjusted under 35 U.S.C. 154(b) by 309 days.

(21) Appl. No.: 16/079,035

(22) PCT Filed: Feb. 28, 2017

(86) PCT No.: PCT/EP2017/054582
§ 371 (c)(1),
(2) Date: Aug. 22, 2018

(87) PCT Pub. No.: WO2017/157650
PCT Pub. Date: Sep. 21, 2017

(65) Prior Publication Data
US 2020/0199672 A1     Jun. 25, 2020

(30) Foreign Application Priority Data
Mar. 18, 2016 (EP) .................................. 16161077

(51) Int. Cl.
| C12Q 1/6883 | (2018.01) |
| C12N 15/10 | (2006.01) |
| G01N 1/34 | (2006.01) |
| G01N 1/40 | (2006.01) |

(52) U.S. Cl.
CPC ....... *C12Q 1/6883* (2013.01); *C12N 15/1006* (2013.01); *G01N 1/34* (2013.01); *G01N 1/405* (2013.01); *G01N 1/4055* (2013.01)

(58) Field of Classification Search
CPC .... C12Q 1/6883; C12N 15/1006; G01N 1/34; G01N 1/405; G01N 1/4055
See application file for complete search history.

(56) References Cited

U.S. PATENT DOCUMENTS 7,977,109 B2    7/2011    Ritt et al.

FOREIGN PATENT DOCUMENTS

| CN | 104254776 A | 12/2014 |
| JP | 2009/518020 A * | 5/2009 |
| WO | 2002072870 A1 | 9/2002 |
| WO | 2012007569 A1 | 1/2012 |
| WO | 2013022342 A1 | 2/2013 |
| WO | 2013043562 A1 | 3/2013 |
| WO | 2013067520 A1 | 5/2013 |
| WO | 2013/165870 A1 | 11/2013 |
| WO | 2013165870 A1 | 11/2013 |
| WO | 2014/143714 A2 | 9/2014 |
| WO | 2015059065 A1 | 4/2015 |

OTHER PUBLICATIONS

Buroker et al. Journal of Medical Diagnostic Methods. 2013. 2(3): 7 pages. (Year: 2013).*
Dauner et al. Am J Trap Med Hyg. 2015. 93(1):46-53. (Year: 2015).*
Andriamandimby et al. PLOS Neglected Tropical Diseases. 2013. 7(7):e2339. (Year: 2013).*
Prado et al. Journal of Virological Methods. 2005. 125:75-81. (Year: 2005).*
Karlsson et al. Clinical Chemistry. 2003. 49(6):979. (Year: 2003).*
Hill et al. Analysis of Circulating miRNA from Dried Blood Spots. Jul. 14, 2014. SelectScience. (Year: 2014).*
Atneosen-Asegg et al. Pediatric Research. 2021. 89:1780-1787. (Year: 2021).*
Diener et al. Critical Reviews in Clinical Laboratory Sciences. 2019. 56(2):111-117. (Year: 2019).*
International Search Report in PCT/EP2017/054582, dated May 2, 2017, 4 pages.
Edelbroek, et al. "Dried blood spot methods in therapeutic drug monitoring: methods, assays, and pitfalls." Therapeutic drug monitoring 31, No. 3 (2009): 327-336.
Göhring, et al. "Influence of different extraction methods and PCR techniques on the sensitivity of HCMV-DNA detection in dried blood spot (DBS) filter cards." Journal of Clinical Virology 48, No. 4 (2010): 278-281.
Vogel, et al. "Multivariate miRNA signatures as biomarkers for non-ischaemic systolic heart failure." European heart journal 34, No. 36 (2013): 2812-2823.
Voellenkle, et al. "MicroRNA signatures in peripheral blood mononuclear cells of chronic heart failure patients." Physiological genomics 42, No. 3 (2010): 420-426.
Ponnusamy et al., A study of microRNAs from dried blood spots in newborns after perinatal asphyxia: a simple and feasible biosampling method. Pediatric research. May 2016;79(5):799-805.
Taylor, R.T, et al., Circadian Rhythm of Cardiovascular Disease-Related Micro RNAs from HemaSpot™ Dried Blood Samples, B-010, Clinical Chemistry, vol. 61, No. 10, Supplement 2015, S123-S124.

* cited by examiner

*Primary Examiner* — Joseph G. Dauner
(74) *Attorney, Agent, or Firm* — Kilpatrick Townsend & Stockton LLP

(57) ABSTRACT

The present invention relates to a method of removing an RNA fraction with ≥200 nucleotides in length from a whole blood sample. The present invention also relates to a method of purifying an RNA fraction with <200 nucleotides in length from a whole blood sample. The present invention further relates to a method of determining the level of RNA molecules with <200 nucleotides in length. In addition, the present invention relates to a method for diagnosing a disease in an individual. Moreover, the present invention relates to a kit which is useful for carrying out the methods of the present invention.

12 Claims, 16 Drawing Sheets
Specification includes a Sequence Listing.

FIGURE 5

| SEQ ID NO: | miRNA | gTotal Gene Signal (A) | gTotal GeneSignal (B) |
|---|---|---|---|
| 1 | hsa-miR-451a | 163371 | 142265 |
| 2 | hsa-miR-16-5p | 139870 | 120550 |
| 3 | hsa-miR-15b-5p | 112389 | 75044 |
| 4 | hsa-miR-144-3p | 111793 | 48692 |
| 5 | hsa-let-7a-5p | 85577 | 67800 |
| 6 | hsa-miR-19b-3p | 79045 | 35603 |
| 7 | hsa-let-7f-5p | 72429 | 46812 |
| 8 | hsa-let-7b-5p | 71346 | 67652 |
| 9 | hsa-miR-20a-5p | 70079 | 37010 |
| 10 | hsa-miR-486-5p | 66439 | 54350 |
| 11 | hsa-miR-15a-5p | 64365 | 33946 |
| 12 | hsa-miR-26b-5p | 64186 | 32948 |
| 13 | hsa-miR-142-3p | 63789 | 17166 |
| 14 | hsa-let-7g-5p | 63079 | 34930 |
| 15 | hsa-let-7i-5p | 61276 | 36081 |
| 16 | hsa-miR-106b-5p | 60205 | 25911 |
| 17 | hsa-miR-107 | 52623 | 40784 |
| 18 | hsa-miR-25-3p | 45550 | 29761 |
| 19 | hsa-miR-19a-3p | 41505 | 9967 |
| 20 | hsa-miR-223-3p | 39792 | 19567 |
| 21 | hsa-miR-4306 | 37357 | 21482 |
| 22 | hsa-miR-92a-3p | 36912 | 31901 |
| 23 | hsa-miR-144-5p | 34077 | 22262 |
| 24 | hsa-miR-103a-3p | 33567 | 27524 |
| 25 | hsa-miR-20b-5p | 32324 | 16603 |
| 26 | hsa-miR-21-5p | 30748 | 13628 |
| 27 | hsa-let-7d-5p | 29179 | 21396 |
| 28 | hsa-miR-17-5p | 28916 | 17407 |
| 29 | hsa-miR-101-3p | 28060 | 6040 |
| 30 | hsa-miR-185-5p | 27711 | 12351 |
| 31 | hsa-miR-7977 | 25257 | 25273 |
| 32 | hsa-let-7c-5p | 24313 | 22411 |
| 33 | hsa-miR-126-3p | 23566 | 12387 |
| 34 | hsa-miR-93-5p | 22857 | 15302 |
| 35 | hsa-miR-22-3p | 21352 | 15362 |
| 36 | hsa-miR-363-3p | 18685 | 10983 |
| 37 | hsa-miR-374a-5p | 17002 | 3956 |
| 38 | hsa-miR-142-5p | 16124 | 2720 |
| 39 | hsa-miR-29c-3p | 14117 | 3887 |
| 40 | hsa-miR-5100 | 12321 | 15857 |
| 41 | hsa-miR-30b-5p | 11134 | 6402 |
| 42 | hsa-miR-425-5p | 10549 | 7636 |
| 43 | hsa-miR-26a-5p | 10358 | 6690 |
| 44 | hsa-miR-140-3p | 9299 | 5248 |
| 45 | hsa-miR-130a-3p | 7797 | 5272 |
| 46 | hsa-miR-30e-5p | 7670 | 2481 |
| 47 | hsa-miR-320d | 7402 | 7055 |
| 48 | hsa-miR-320b | 6417 | 6025 |
| 49 | hsa-miR-96-5p | 6320 | 1921 |
| 50 | hsa-miR-8069 | 6305 | 3660 |
| 51 | hsa-miR-320e | 5943 | 5683 |
| 52 | hsa-miR-151a-5p | 5201 | 3192 |
| 53 | hsa-miR-320c | 5013 | 4726 |
| 54 | hsa-miR-29b-3p | 4891 | 1072 |
| 55 | hsa-miR-18a-5p | 4287 | 1822 |
| 56 | hsa-miR-454-3p | 4086 | 2339 |
| 57 | hsa-miR-374b-5p | 3994 | 2281 |
| 58 | hsa-miR-7641 | 3820 | 6761 |
| 59 | hsa-miR-194-5p | 3707 | 1908 |
| 60 | hsa-miR-301a-3p | 3654 | 1051 |
| 61 | hsa-miR-320a | 3653 | 3603 |
| 62 | hsa-miR-192-5p | 3597 | 1366 |
| 63 | hsa-miR-4516 | 3507 | 2301 |
| 64 | hsa-miR-331-3p | 3444 | 1677 |
| 65 | hsa-miR-660-5p | 3431 | 1182 |
| 66 | hsa-miR-150-5p | 3430 | 2461 |
| 67 | hsa-miR-24-3p | 3224 | 2503 |
| 68 | hsa-miR-23a-3p | 2712 | 2086 |
| 69 | hsa-miR-18b-5p | 2700 | 1127 |
| 70 | hsa-miR-29a-3p | 2684 | 1111 |
| 71 | hsa-miR-30c-5p | 2649 | 1669 |
| 72 | hsa-miR-183-5p | 2477 | 1714 |
| 73 | hsa-miR-3960 | 2471 | 2226 |
| 74 | hsa-miR-590-5p | 2465 | 324 |
| 75 | hsa-miR-27a-3p | 2440 | 782 |
| 76 | hsa-miR-324-3p | 2431 | 2076 |
| 77 | hsa-miR-30d-5p | 2384 | 1796 |
| 78 | hsa-miR-6089 | 2295 | 2557 |
| 79 | hsa-miR-186-5p | 2138 | 1100 |
| 80 | hsa-miR-7-5p | 2137 | 749 |
| 81 | hsa-miR-151b | 2134 | 1427 |
| 82 | hsa-miR-652-3p | 2078 | 1658 |
| 83 | hsa-miR-215-5p | 2008 | 763 |
| 84 | hsa-miR-181a-5p | 1913 | 924 |
| 85 | hsa-miR-424-5p | 1872 | 305 |
| 86 | hsa-miR-4505 | 1735 | 402 |
| 87 | hsa-miR-148a-3p | 1680 | 339 |
| 88 | hsa-miR-1273g-3p | 1663 | 3600 |
| 89 | hsa-miR-6090 | 1620 | 2225 |
| 90 | hsa-miR-17-3p | 1595 | 252 |
| 91 | hsa-miR-1260a | 1544 | 2453 |
| 92 | hsa-miR-98-5p | 1508 | 779 |
| 93 | hsa-miR-130b-3p | 1366 | 1021 |
| 94 | hsa-miR-4286 | 1355 | 1834 |
| 95 | hsa-miR-6803-5p | 1309 | 354 |
| 96 | hsa-miR-140-5p | 1250 | 467 |
| 97 | hsa-miR-148b-3p | 1215 | 420 |
| 98 | hsa-miR-195-5p | 1194 | 779 |

Figure 5 Cont.

| 99 | hsa-miR-210-3p | 1173 | 747 | 151 | hsa-miR-584-5p | 283 | 247 |
|---|---|---|---|---|---|---|---|
| 100 | hsa-miR-423-5p | 1130 | 1255 | 152 | hsa-miR-29c-5p | 281 | 159 |
| 101 | hsa-miR-4507 | 1102 | 272 | 153 | hsa-miR-4459 | 279 | 597 |
| 102 | hsa-miR-32-5p | 1044 | 87 | 154 | hsa-miR-221-3p | 274 | 269 |
| 103 | hsa-miR-532-5p | 991 | 599 | 155 | hsa-miR-338-3p | 269 | 107 |
| 104 | hsa-miR-199a-3p | 874 | 396 | 156 | hsa-miR-1915-3p | 267 | 204 |
| 105 | hsa-miR-6125 | 866 | 805 | 157 | hsa-miR-4318 | 255 | 189 |
| 106 | hsa-miR-484 | 828 | 588 | 158 | hsa-miR-6749-5p | 251 | 527 |
| 107 | hsa-miR-342-3p | 721 | 566 | 159 | hsa-miR-629-5p | 251 | 169 |
| 108 | hsa-miR-362-5p | 696 | 430 | 160 | hsa-miR-199a-5p | 235 | 84 |
| 109 | hsa-miR-550a-3p | 656 | 297 | 161 | hsa-miR-502-5p | 235 | 70 |
| 110 | hsa-miR-6869-5p | 638 | 742 | 162 | hsa-miR-6085 | 228 | 393 |
| 111 | hsa-miR-6875-5p | 629 | 1159 | 163 | hsa-miR-190a-5p | 227 | 54 |
| 112 | hsa-miR-27b-3p | 613 | 318 | 164 | hsa-miR-6794-5p | 216 | 166 |
| 113 | hsa-miR-1587 | 582 | 114 | 165 | hsa-miR-361-3p | 215 | 154 |
| 114 | hsa-miR-126-5p | 579 | 223 | 166 | hsa-miR-625-5p | 214 | 176 |
| 115 | hsa-miR-4443 | 576 | 2918 | 167 | hsa-miR-15b-3p | 204 | 93 |
| 116 | hsa-miR-151a-3p | 570 | 361 | 168 | hsa-miR-374c-5p | 200 | 127 |
| 117 | hsa-miR-146b-5p | 562 | 244 | 169 | hsa-miR-4763-3p | 194 | 156 |
| 118 | hsa-miR-324-5p | 553 | 305 | 170 | hsa-miR-361-5p | 192 | 154 |
| 119 | hsa-miR-6821-5p | 523 | 653 | 171 | hsa-miR-4530 | 185 | 193 |
| 120 | hsa-miR-128-3p | 499 | 259 | 172 | hsa-let-7e-5p | 182 | 118 |
| 121 | hsa-miR-500a-3p | 478 | 268 | 173 | hsa-miR-6779-5p | 178 | 31 |
| 122 | hsa-miR-4281 | 467 | 456 | 174 | hsa-miR-638 | 177 | 283 |
| 123 | hsa-miR-6127 | 462 | 793 | 175 | hsa-miR-196b-5p | 173 | 71 |
| 124 | hsa-miR-362-3p | 450 | 65 | 176 | hsa-miR-5001-5p | 169 | 121 |
| 125 | hsa-miR-340-5p | 449 | 99 | 177 | hsa-miR-5739 | 169 | 482 |
| 126 | hsa-miR-378i | 445 | 317 | 178 | hsa-miR-505-5p | 167 | 151 |
| 127 | hsa-miR-550a-3-5p | 438 | 264 | 179 | hsa-miR-1202 | 166 | 286 |
| 128 | hsa-miR-146a-5p | 433 | 429 | 180 | hsa-miR-30e-3p | 161 | 91 |
| 129 | hsa-miR-3665 | 414 | 417 | 181 | hsa-miR-1207-5p | 161 | 186 |
| 130 | hsa-miR-532-3p | 413 | 270 | 182 | hsa-miR-6879-5p | 157 | 245 |
| 131 | hsa-miR-4687-3p | 406 | 426 | 183 | hsa-miR-28-5p | 156 | 72 |
| 132 | hsa-miR-6087 | 402 | 547 | 184 | hsa-miR-7-1-3p | 154 | 62 |
| 133 | hsa-miR-502-3p | 402 | 254 | 185 | hsa-miR-197-3p | 151 | 118 |
| 134 | hsa-miR-3656 | 389 | 277 | 186 | hsa-miR-6756-5p | 148 | 94 |
| 135 | hsa-miR-182-5p | 389 | 377 | 187 | hsa-miR-219a-5p | 147 | 14 |
| 136 | hsa-miR-16-2-3p | 386 | 423 | 188 | hsa-miR-3162-5p | 141 | 209 |
| 137 | hsa-miR-20a-3p | 368 | 161 | 189 | hsa-miR-342-5p | 140 | 143 |
| 138 | hsa-miR-6724-5p | 354 | 164 | 190 | hsa-miR-627-5p | 140 | 70 |
| 139 | hsa-miR-1260b | 353 | 534 | 191 | hsa-miR-335-5p | 137 | 54 |
| 140 | hsa-miR-23b-3p | 341 | 243 | 192 | hsa-miR-671-5p | 129 | 33 |
| 141 | hsa-miR-6088 | 327 | 315 | 193 | hsa-miR-4788 | 128 | 107 |
| 142 | hsa-miR-4466 | 322 | 354 | 194 | hsa-miR-4463 | 125 | 92 |
| 143 | hsa-miR-4284 | 319 | 403 | 195 | hsa-miR-501-5p | 119 | 50 |
| 144 | hsa-miR-6800-5p | 313 | 416 | 196 | hsa-miR-4787-5p | 117 | 101 |
| 145 | hsa-miR-7704 | 313 | 278 | 197 | hsa-miR-6780b-5p | 115 | 178 |
| 146 | hsa-miR-6727-5p | 306 | 68 | 198 | hsa-miR-378d | 115 | 65 |
| 147 | hsa-miR-2861 | 305 | 357 | 199 | hsa-miR-574-3p | 114 | 106 |
| 148 | hsa-miR-378a-3p | 299 | 225 | 200 | hsa-miR-545-3p | 111 | 15 |
| 149 | hsa-miR-222-3p | 294 | 263 | 201 | hsa-miR-500a-5p | 110 | 65 |
| 150 | hsa-miR-624-5p | 284 | 64 | 202 | hsa-miR-132-3p | 108 | 77 |

Figure 5 Cont.

| | | | | | | | |
|---|---|---|---|---|---|---|---|
| 203 | hsa-miR-4713-3p | 108 | 164 | 255 | hsa-miR-6723-5p | 59 | 85 |
| 204 | hsa-miR-598-3p | 106 | 32 | 256 | hsa-miR-365a-3p | 58 | 50 |
| 205 | hsa-miR-744-5p | 105 | 98 | 257 | hsa-miR-4291 | 57 | 57 |
| 206 | hsa-miR-7114-5p | 105 | 189 | 258 | hsa-miR-6850-5p | 57 | 81 |
| 207 | hsa-miR-155-5p | 104 | 120 | 259 | hsa-miR-125a-5p | 55 | 58 |
| 208 | hsa-miR-6740-5p | 104 | 153 | 260 | hsa-miR-1268a | 55 | 48 |
| 209 | hsa-miR-101-5p | 103 | 43 | 261 | hsa-miR-7847-3p | 54 | 40 |
| 210 | hsa-miR-4739 | 100 | 73 | 262 | hsa-miR-6791-5p | 54 | 59 |
| 211 | hsa-miR-6165 | 100 | 213 | 263 | hsa-miR-4298 | 53 | 32 |
| 212 | hsa-miR-371b-5p | 98 | 87 | 264 | hsa-miR-664a-3p | 52 | 56 |
| 213 | hsa-miR-6126 | 98 | 90 | 265 | hsa-miR-3195 | 52 | 105 |
| 214 | hsa-miR-6124 | 96 | 129 | 266 | hsa-miR-1268b | 51 | 54 |
| 215 | hsa-miR-3200-5p | 96 | 77 | 267 | hsa-miR-1305 | 51 | 77 |
| 216 | hsa-miR-1225-5p | 94 | 119 | 268 | hsa-miR-4442 | 51 | 64 |
| 217 | hsa-miR-1246 | 92 | 74 | 269 | hsa-miR-1285-3p | 51 | 28 |
| 218 | hsa-miR-4732-5p | 92 | 89 | 270 | hsa-miR-340-3p | 51 | 23 |
| 219 | hsa-miR-6068 | 91 | 117 | 271 | hsa-miR-3620-5p | 49 | 22 |
| 220 | hsa-miR-15a-3p | 90 | 22 | 272 | hsa-miR-642a-3p | 49 | 41 |
| 221 | hsa-miR-7107-5p | 89 | 187 | 273 | hsa-miR-3135b | 49 | 102 |
| 222 | hsa-miR-197-5p | 89 | 99 | 274 | hsa-miR-7108-5p | 49 | 46 |
| 223 | hsa-miR-181b-5p | 87 | 56 | 275 | hsa-miR-3141 | 49 | 38 |
| 224 | hsa-miR-1229-5p | 87 | 45 | 276 | hsa-miR-223-5p | 48 | 36 |
| 225 | hsa-miR-6826-5p | 86 | 129 | 277 | hsa-miR-378g | 48 | 24 |
| 226 | hsa-miR-939-5p | 85 | 127 | 278 | hsa-miR-145-5p | 48 | 34 |
| 227 | hsa-miR-3940-5p | 85 | 75 | 279 | hsa-miR-8063 | 48 | 36 |
| 228 | hsa-miR-937-5p | 82 | 53 | 280 | hsa-miR-5787 | 47 | 77 |
| 229 | hsa-miR-181c-5p | 81 | 49 | 281 | hsa-miR-4299 | 47 | 47 |
| 230 | hsa-miR-376c-3p | 80 | 25 | 282 | hsa-miR-3679-5p | 45 | 63 |
| 231 | hsa-miR-6717-5p | 79 | 130 | 283 | hsa-miR-542-5p | 45 | 21 |
| 232 | hsa-miR-505-3p | 77 | 38 | 284 | hsa-miR-4690-5p | 45 | 34 |
| 233 | hsa-miR-4685-5p | 76 | 108 | 285 | hsa-miR-21-3p | 45 | 24 |
| 234 | hsa-miR-494-3p | 75 | 118 | 286 | hsa-miR-1914-3p | 44 | 61 |
| 235 | hsa-miR-22-5p | 73 | 64 | 287 | hsa-miR-4270 | 44 | 44 |
| 236 | hsa-miR-550b-2-5p | 73 | 50 | 288 | hsa-miR-6763-5p | 44 | 70 |
| 237 | hsa-miR-582-5p | 72 | 44 | 289 | hsa-miR-542-3p | 44 | 8 |
| 238 | hsa-miR-30a-5p | 72 | 46 | 290 | hsa-miR-6831-5p | 43 | 14 |
| 239 | hsa-miR-6131 | 71 | 117 | 291 | hsa-miR-1255b-5p | 42 | 31 |
| 240 | hsa-miR-664b-3p | 70 | 78 | 292 | hsa-miR-378a-5p | 42 | 26 |
| 241 | hsa-miR-3200-3p | 69 | 39 | 293 | hsa-miR-6820-5p | 41 | 24 |
| 242 | hsa-miR-193a-3p | 69 | 6 | 294 | hsa-miR-4486 | 41 | 13 |
| 243 | hsa-miR-6891-5p | 65 | 82 | 295 | hsa-miR-6799-5p | 40 | 13 |
| 244 | hsa-miR-199b-5p | 64 | 23 | 296 | hsa-miR-628-5p | 40 | 17 |
| 245 | hsa-miR-4433b-3p | 64 | 45 | 297 | hsa-let-7d-3p | 40 | 36 |
| 246 | hsa-miR-6073 | 63 | 77 | 298 | hsa-miR-557 | 39 | 28 |
| 247 | hsa-miR-152-3p | 63 | 15 | 299 | hsa-miR-188-5p | 39 | 19 |
| 248 | hsa-miR-6734-5p | 62 | 79 | 300 | hsa-miR-500b-5p | 39 | 20 |
| 249 | hsa-miR-376a-3p | 62 | 21 | 301 | hsa-miR-3663-3p | 39 | 44 |
| 250 | hsa-miR-93-3p | 61 | 44 | 302 | hsa-miR-6789-5p | 39 | 29 |
| 251 | hsa-miR-3196 | 61 | 74 | 303 | hsa-miR-377-3p | 38 | 12 |
| 252 | hsa-miR-501-3p | 60 | 41 | 304 | hsa-miR-3652 | 38 | 86 |
| 253 | hsa-miR-3198 | 60 | 89 | 305 | hsa-miR-6767-5p | 38 | 53 |
| 254 | hsa-miR-4732-3p | 60 | 52 | 306 | hsa-miR-1307-5p | 37 | 3 |

Figure 5 Cont.

| 307 | hsa-miR-5581-5p | 37 | 53 | 359 | hsa-miR-339-3p | 22 | 17 |
|---|---|---|---|---|---|---|---|
| 308 | hsa-miR-99a-5p | 36 | 46 | 360 | hsa-miR-6512-5p | 21 | 29 |
| 309 | hsa-miR-4716-3p | 36 | 53 | 361 | hsa-miR-7150 | 21 | 84 |
| 310 | hsa-miR-1343-5p | 36 | 23 | 362 | hsa-miR-191-5p | 20 | 19 |
| 311 | hsa-miR-486-3p | 36 | 39 | 363 | hsa-miR-1275 | 20 | 23 |
| 312 | hsa-miR-766-3p | 36 | 26 | 364 | hsa-miR-339-5p | 20 | 26 |
| 313 | hsa-miR-4669 | 35 | 27 | 365 | hsa-miR-7106-5p | 20 | 3 |
| 314 | hsa-miR-141-3p | 35 | 7 | 366 | hsa-miR-5690 | 20 | 6 |
| 315 | hsa-miR-125b-5p | 35 | 197 | 367 | hsa-miR-410-3p | 19 | 10 |
| 316 | hsa-miR-6076 | 35 | 30 | 368 | hsa-miR-454-5p | 19 | 10 |
| 317 | hsa-miR-4695-5p | 34 | 17 | 369 | hsa-miR-4737 | 19 | 4 |
| 318 | hsa-miR-3651 | 34 | 39 | 370 | hsa-miR-7110-5p | 19 | 31 |
| 319 | hsa-miR-942-5p | 34 | 19 | 371 | hsa-miR-1255a | 19 | 11 |
| 320 | hsa-miR-5194 | 33 | 47 | 372 | hsa-miR-193a-5p | 19 | 14 |
| 321 | hsa-miR-450a-5p | 33 | 8 | 373 | hsa-miR-5088-5p | 18 | 27 |
| 322 | hsa-miR-1227-5p | 32 | 46 | 374 | hsa-miR-4651 | 18 | 14 |
| 323 | hsa-miR-4271 | 32 | 20 | 375 | hsa-miR-6812-5p | 18 | 12 |
| 324 | hsa-miR-34a-5p | 32 | 24 | 376 | hsa-miR-664a-5p | 18 | 28 |
| 325 | hsa-miR-874-3p | 32 | 21 | 377 | hsa-miR-99b-5p | 18 | 10 |
| 326 | hsa-miR-4653-3p | 31 | 42 | 378 | hsa-miR-503-5p | 17 | 6 |
| 327 | hsa-miR-769-5p | 31 | 21 | 379 | hsa-miR-548e-3p | 17 | 4 |
| 328 | hsa-miR-328-3p | 31 | 22 | 380 | hsa-miR-5010-5p | 17 | 18 |
| 329 | hsa-miR-183-3p | 31 | 26 | 381 | hsa-miR-1307-3p | 17 | 12 |
| 330 | hsa-miR-192-3p | 31 | 9 | 382 | hsa-miR-548am-5p | 17 | 10 |
| 331 | hsa-miR-6775-5p | 30 | 41 | 383 | hsa-miR-6893-5p | 17 | 17 |
| 332 | hsa-miR-487b-3p | 29 | 22 | 384 | hsa-miR-3127-5p | 17 | 23 |
| 333 | hsa-miR-136-5p | 28 | 8 | 385 | hsa-miR-762 | 17 | 33 |
| 334 | hsa-miR-326 | 28 | 13 | 386 | hsa-miR-4497 | 17 | 29 |
| 335 | hsa-miR-4741 | 28 | 32 | 387 | hsa-miR-409-3p | 16 | 16 |
| 336 | hsa-miR-6722-3p | 28 | 28 | 388 | hsa-miR-3188 | 16 | 18 |
| 337 | hsa-miR-221-5p | 28 | 18 | 389 | hsa-miR-4659a-3p | 16 | 7 |
| 338 | hsa-miR-296-5p | 28 | 24 | 390 | hsa-miR-4745-5p | 15 | 20 |
| 339 | hsa-miR-575 | 26 | 57 | 391 | hsa-miR-4665-3p | 15 | 15 |
| 340 | hsa-miR-6807-5p | 25 | 30 | 392 | hsa-miR-497-5p | 15 | 6 |
| 341 | hsa-miR-3667-5p | 25 | 4 | 393 | hsa-miR-3156-5p | 15 | 19 |
| 342 | hsa-miR-6785-5p | 25 | 69 | 394 | hsa-miR-421 | 15 | 12 |
| 343 | hsa-miR-628-3p | 24 | 22 | 395 | hsa-miR-654-3p | 15 | 7 |
| 344 | hsa-miR-574-5p | 24 | 81 | 396 | hsa-miR-103a-2-5p | 15 | 17 |
| 345 | hsa-miR-200c-3p | 24 | 19 | 397 | hsa-miR-1271-5p | 14 | 6 |
| 346 | hsa-miR-940 | 24 | 26 | 398 | hsa-miR-4317 | 14 | 10 |
| 347 | hsa-miR-10a-5p | 24 | 26 | 399 | hsa-miR-3136-5p | 14 | 9 |
| 348 | hsa-miR-378f | 24 | 12 | 400 | hsa-miR-6840-3p | 14 | 28 |
| 349 | hsa-miR-423-3p | 23 | 17 | 401 | hsa-miR-579-3p | 14 | 3 |
| 350 | hsa-miR-1288-3p | 23 | 29 | 402 | hsa-miR-19b-1-5p | 14 | 6 |
| 351 | hsa-miR-3125 | 23 | 33 | 403 | hsa-miR-1537-3p | 14 | 3 |
| 352 | hsa-miR-3907 | 23 | 96 | 404 | hsa-miR-4455 | 14 | 21 |
| 353 | hsa-let-7i-3p | 23 | 5 | 405 | hsa-miR-499a-5p | 14 | 3 |
| 354 | hsa-miR-7152-3p | 22 | 37 | 406 | hsa-miR-548q | 14 | 13 |
| 355 | hsa-miR-4672 | 22 | 19 | 407 | hsa-miR-495-3p | 14 | 5 |
| 356 | hsa-miR-6780a-5p | 22 | 32 | 408 | hsa-miR-1233-5p | 14 | 40 |
| 357 | hsa-miR-211-3p | 22 | 62 | 409 | hsa-miR-4534 | 13 | 14 |
| 358 | hsa-miR-572 | 22 | 35 | 410 | hsa-miR-378e | 13 | 8 |

Figure 5 Cont.

| | | | | | | | |
|---|---|---|---|---|---|---|---|
| 411 | hsa-miR-4313 | 13 | 9 | 463 | hsa-miR-4261 | 6 | 10 |
| 412 | hsa-miR-148b-5p | 13 | 7 | 464 | hsa-miR-4327 | 4 | 13 |
| 413 | hsa-miR-4323 | 13 | 10 | 465 | hsa-miR-6769b-5p | 4 | 18 |
| 414 | hsa-miR-610 | 13 | 7 | 466 | hsa-miR-483-5p | 3 | 10 |
| 415 | hsa-miR-4634 | 13 | 18 | 467 | hsa-miR-623 | 3 | 13 |
| 416 | hsa-miR-328-5p | 13 | 67 | | | | |
| 417 | hsa-miR-381-3p | 13 | 3 | | | | |
| 418 | hsa-miR-4721 | 13 | 20 | | | | |
| 419 | hsa-miR-6516-5p | 12 | 10 | | | | |
| 420 | hsa-miR-31-5p | 12 | 5 | | | | |
| 421 | hsa-miR-7845-5p | 12 | 16 | | | | |
| 422 | hsa-miR-892b | 12 | 17 | | | | |
| 423 | hsa-miR-6786-5p | 12 | 14 | | | | |
| 424 | hsa-miR-3163 | 12 | 6 | | | | |
| 425 | hsa-miR-1270 | 12 | 12 | | | | |
| 426 | hsa-miR-642b-3p | 12 | 11 | | | | |
| 427 | hsa-miR-106a-3p | 12 | 4 | | | | |
| 428 | hsa-miR-6728-5p | 12 | 17 | | | | |
| 429 | hsa-miR-143-3p | 12 | 3 | | | | |
| 430 | hsa-miR-4499 | 11 | 13 | | | | |
| 431 | hsa-miR-4632-5p | 11 | 12 | | | | |
| 432 | hsa-miR-548d-5p | 11 | 2 | | | | |
| 433 | hsa-miR-3911 | 11 | 8 | | | | |
| 434 | hsa-miR-6075 | 11 | 7 | | | | |
| 435 | hsa-miR-1228-3p | 11 | 12 | | | | |
| 436 | hsa-miR-134-5p | 11 | 18 | | | | |
| 437 | hsa-miR-6515-3p | 11 | 13 | | | | |
| 438 | hsa-miR-1234-3p | 11 | 11 | | | | |
| 439 | hsa-miR-6833-5p | 10 | 8 | | | | |
| 440 | hsa-miR-224-5p | 10 | 12 | | | | |
| 441 | hsa-miR-6829-5p | 10 | 15 | | | | |
| 442 | hsa-miR-4742-5p | 10 | 14 | | | | |
| 443 | hsa-miR-2110 | 10 | 12 | | | | |
| 444 | hsa-miR-100-5p | 10 | 410 | | | | |
| 445 | hsa-miR-1973 | 10 | 28 | | | | |
| 446 | hsa-miR-5006-5p | 10 | 12 | | | | |
| 447 | hsa-miR-6872-3p | 10 | 12 | | | | |
| 448 | hsa-miR-4465 | 9 | 18 | | | | |
| 449 | hsa-miR-1281 | 9 | 11 | | | | |
| 450 | hsa-miR-8072 | 9 | 18 | | | | |
| 451 | hsa-miR-6752-5p | 9 | 14 | | | | |
| 452 | hsa-miR-630 | 8 | 42 | | | | |
| 453 | hsa-miR-212-3p | 8 | 23 | | | | |
| 454 | hsa-miR-6510-5p | 8 | 22 | | | | |
| 455 | hsa-miR-2392 | 8 | 13 | | | | |
| 456 | hsa-miR-181d-5p | 8 | 13 | | | | |
| 457 | hsa-miR-6849-5p | 8 | 31 | | | | |
| 458 | hsa-miR-150-3p | 7 | 14 | | | | |
| 459 | hsa-miR-29b-2-5p | 7 | 11 | | | | |
| 460 | hsa-miR-4800-5p | 7 | 13 | | | | |
| 461 | hsa-miR-432-5p | 6 | 11 | | | | |
| 462 | hsa-miR-127-3p | 6 | 11 | | | | | hsa-miR-1250-3p (SEQ ID NO: 468)
hsa-miR-3138 (SEQ ID NO: 469)
hsa-miR-4767 (SEQ ID NO: 470)
hsa-miR-551b-3p (SEQ ID NO: 471)
hsa-miR-5703 (SEQ ID NO: 472)
hsa-miR-6716-3p (SEQ ID NO: 473)
hsa-miR-718 (SEQ ID NO: 474)
hsa-miR-8071 (SEQ ID NO: 475)

Figure 10

| miRNA | limma.rawp | limma.adjp | ttest.rawp | ttest.adjp | AUC | mean.adjuvant | mean.palliative | fold_change | log2_fold_change |
|---|---|---|---|---|---|---|---|---|---|
| hsa-miR-1202 | 0.029817521 | 0.608516285 | 0.027447818 | 0.477107663 | 0.681372549 | 597.0639952 | 873.0397815 | 0.683890938 | -0.548161822 |
| hsa-miR-1250-3p | 0.019778769 | 0.608516285 | 0.035582751 | 0.496147911 | 0.261437908 | 28.37065111 | 21.50904813 | 1.319010071 | 0.39945558 |
| hsa-miR-140-5p | 0.014325763 | 0.608516285 | 0.013557299 | 0.419479035 | 0.264705882 | 646.6693735 | 520.6639018 | 1.242009233 | 0.312675899 |
| hsa-miR-146b-5p | 0.014028398 | 0.608516285 | 0.010703438 | 0.419479035 | 0.289215686 | 209.8421757 | 160.5142154 | 1.307312098 | 0.386603601 |
| hsa-miR-150-3p | 0.043202265 | 0.608516285 | 0.010749976 | 0.419479035 | 0.691176471 | 24.23207734 | 30.06110828 | 0.806093944 | -0.310980111 |
| hsa-miR-150-5p | 0.003318936 | 0.608516285 | 0.019034207 | 0.43119737 | 0.308823529 | 1955.064781 | 668.2694351 | 2.925563671 | 1.548714617 |
| hsa-miR-1915-3p | 0.0682736 | 0.624382729 | 0.042509788 | 0.523401761 | 0.661764706 | 114.6648605 | 134.5660703 | 0.852108263 | -0.230891353 |
| hsa-miR-2861 | 0.019345011 | 0.608516285 | 0.010864012 | 0.419479035 | 0.689542484 | 135.8860881 | 165.468412 | 0.821220718 | -0.284158071 |
| hsa-miR-296-5p | 0.033039325 | 0.608516285 | 0.035453444 | 0.496147911 | 0.66503268 | 27.00515256 | 30.22588154 | 0.893444664 | -0.162549718 |
| hsa-miR-3138 | 0.076201354 | 0.68234849 | 0.023347404 | 0.43119737 | 0.691176471 | 23.08891757 | 27.30473184 | 0.84560133 | -0.241950448 |
| hsa-miR-328-5p | 0.028075461 | 0.608516285 | 0.017397433 | 0.43119737 | 0.684640523 | 37.74116241 | 56.12899723 | 0.67240044 | -0.572607427 |
| hsa-miR-331-3p | 0.028013859 | 0.608516285 | 0.007817933 | 0.419479035 | 0.300653595 | 1459.120362 | 1250.814424 | 1.166536246 | 0.222231134 |
| hsa-miR-342-3p | 0.008489608 | 0.608516285 | 0.004353233 | 0.419479035 | 0.282679739 | 251.8517796 | 195.0531664 | 1.291195545 | 0.368707506 |
| hsa-miR-342-5p | 0.049065548 | 0.608516285 | 0.038424755 | 0.504645122 | 0.326797386 | 57.05980733 | 46.4788392 | 1.227651299 | 0.295900837 |
| hsa-miR-3679-5p | 0.029282091 | 0.608516285 | 0.014657504 | 0.419479035 | 0.656862745 | 148.5992996 | 213.3654346 | 0.696454418 | -0.521899161 |
| hsa-miR-4270 | 0.028741569 | 0.608516285 | 0.01496353 | 0.419479035 | 0.668300654 | 61.01227575 | 83.77119061 | 0.728320504 | -0.457354634 |
| hsa-miR-4327 | 0.06182773 | 0.624382729 | 0.018331141 | 0.43119737 | 0.647058824 | 20.47150825 | 25.72606435 | 0.79574971 | -0.329613369 |
| hsa-miR-4459 | 0.068110204 | 0.624382729 | 0.032292938 | 0.496147911 | 0.617647059 | 676.8462427 | 1299.790012 | 0.52073507 | -0.941378524 |
| hsa-miR-4466 | 0.062775291 | 0.624382729 | 0.035633156 | 0.496147911 | 0.645424837 | 185.1573635 | 221.0290968 | 0.837705832 | -0.255484377 |
| hsa-miR-4530 | 0.064698238 | 0.624382729 | 0.038140222 | 0.504645122 | 0.666666667 | 250.9580914 | 329.5938549 | 0.761416172 | -0.393242882 |
| hsa-miR-4634 | 0.04089815 | 0.608516285 | 0.046160141 | 0.556747827 | 0.673202614 | 115.8567308 | 147.377253 | 0.78612356 | -0.347172008 |
| hsa-miR-4672 | 0.039478591 | 0.608516285 | 0.033534918 | 0.496147911 | 0.683006536 | 41.77141326 | 48.71698667 | 0.857430151 | -0.221908945 |
| hsa-miR-4745-5p | 0.013956618 | 0.608516285 | 0.006766681 | 0.419479035 | 0.676470588 | 23.94985284 | 28.67755317 | 0.835142827 | -0.259905144 |
| hsa-miR-4763-3p | 0.031838583 | 0.608516285 | 0.025488464 | 0.456475212 | 0.68627451 | 126.4012197 | 162.1244303 | 0.779655598 | -0.359091121 |
| hsa-miR-4767 | 0.049526793 | 0.608516285 | 0.033417537 | 0.496147911 | 0.678104575 | 36.75234435 | 43.45202917 | 0.8458144224 | -0.241587272 |
| hsa-miR-551b-3p | 0.00269497 | 0.608516285 | 0.007570867 | 0.419479035 | 0.269607843 | 20.31119751 | 16.90918941 | 1.201192856 | 0.264467799 |

Figure 10 Cont.

| | | | | | | | |
|---|---|---|---|---|---|---|---|
| hsa-miR-5703 | 0.017864211 | 0.608516285 | 0.015402228 | 0.419479035 | 0.681372549 | 216.7224571 | 410.8403815 | 0.527510115 | -0.922729336 |
| hsa-miR-575 | 0.010590652 | 0.608516285 | 0.006061606 | 0.419479035 | 0.709150327 | 84.34844129 | 117.0417951 | 0.720669409 | -0.472590488 |
| hsa-miR-6087 | 0.020992589 | 0.608516285 | 0.015615125 | 0.419479035 | 0.679738562 | 694.5589831 | 1040.775772 | 0.667347378 | -0.583490163 |
| hsa-miR-630 | 0.029456907 | 0.608516285 | 0.022811749 | 0.43119737 | 0.666666667 | 182.3812212 | 322.8984684 | 0.564825291 | -0.824123407 |
| hsa-miR-638 | 0.009717849 | 0.608516285 | 0.002590664 | 0.419479035 | 0.722222222 | 72.08661638 | 96.1316202 | 0.749874144 | -0.415279616 |
| hsa-miR-642a-3p | 0.038543523 | 0.608516285 | 0.013503849 | 0.419479035 | 0.619281046 | 144.0000965 | 295.9646622 | 0.486544898 | -1.039355152 |
| hsa-miR-642b-3p | 0.044664051 | 0.608516285 | 0.012014663 | 0.419479035 | 0.612745098 | 30.95796752 | 40.399639 | 0.766293172 | -0.384031644 |
| hsa-miR-6512-5p | 0.035256292 | 0.608516285 | 0.041939348 | 0.523401761 | 0.328431373 | 33.24701485 | 29.26072917 | 1.136233299 | 0.184825909 |
| hsa-miR-6716-3p | 0.036880867 | 0.608516285 | 0.047268692 | 0.558715941 | 0.313372549 | 62.74897117 | 43.92181554 | 1.42865158 | 0.514654114 |
| hsa-miR-6752-5p | 0.048488349 | 0.608516285 | 0.019268544 | 0.43119737 | 0.668300654 | 30.12179058 | 34.87045608 | 0.863819805 | -0.211977 |
| hsa-miR-6786-5p | 0.006499207 | 0.608516285 | 0.001565159 | 0.419479035 | 0.715686275 | 27.88426612 | 34.36232102 | 0.811477959 | -0.301376186 |
| hsa-miR-6789-5p | 0.035059896 | 0.608516285 | 0.023345508 | 0.43119737 | 0.676470588 | 43.89483604 | 54.71030855 | 0.802313809 | -0.317761467 |
| hsa-miR-6791-5p | 0.018415696 | 0.608516285 | 0.006454289 | 0.419479035 | 0.72875817 | 29.96471892 | 34.74218485 | 0.86248804 | -0.213423644 |
| hsa-miR-6831-5p | 0.048456867 | 0.608516285 | 0.021094283 | 0.43119737 | 0.64689281 | 48.87471308 | 58.33658517 | 0.83780552 | -0.255312705 |
| hsa-miR-6850-5p | 0.027764277 | 0.608516285 | 0.011317232 | 0.419479035 | 0.668300654 | 52.111133631 | 64.1649768 | 0.81214611 | -0.300188794 |
| hsa-miR-6891-5p | 0.010960066 | 0.608516285 | 0.001812554 | 0.419479035 | 0.709150327 | 41.37465602 | 51.19489566 | 0.808179321 | -0.307252657 |
| hsa-miR-7107-5p | 0.062098907 | 0.624382729 | 0.030540288 | 0.496147911 | 0.650326797 | 155.486494 | 196.6454463 | 0.790694608 | -0.338807509 |
| hsa-miR-7110-5p | 0.029358816 | 0.608516285 | 0.008609658 | 0.419479035 | 0.650326797 | 77.00612265 | 116.9960397 | 0.658194268 | -0.603414633 |
| hsa-miR-7150 | 0.007999271 | 0.608516285 | 0.003548561 | 0.419479035 | 0.70751634 | 74.89441412 | 112.3330749 | 0.666717386 | -0.584852745 |
| hsa-miR-718 | 0.046823041 | 0.608516285 | 0.021056296 | 0.43119737 | 0.660130719 | 20.40825361 | 25.17934604 | 0.810515634 | -0.303088081 |
| hsa-miR-762 | 0.054963372 | 0.6153398223 | 0.048840067 | 0.565970192 | 0.689542484 | 54.15375937 | 68.78024245 | 0.7873447 | -0.344932708 |
| hsa-miR-7704 | 0.066641102 | 0.624382729 | 0.031674408 | 0.496147911 | 0.630718954 | 92.61822591 | 116.5360963 | 0.794759983 | -0.331408862 |
| hsa-miR-8071 | 0.032852994 | 0.608516285 | 0.036098748 | 0.496147911 | 0.336601307 | 16.3416183 | 14.779708 | 1.105679375 | 0.144933093 |
| hsa-miR-8072 | 0.090880859 | 0.716141171 | 0.023113643 | 0.43119737 | 0.593137255 | 22.619903149 | 27.70214424 | 0.816508329 | -0.292460493 |
| hsa-miR-940 | 0.03685856 | 0.608516285 | 0.041605891 | 0.523401761 | 0.668300654 | 146.6708879 | 183.394924 | 0.799754349 | -0.322371163 |

PURIFICATION OF RNA FRACTIONS USING A HYDROPHILIC POLYMERIC MATERIAL

The present invention relates to a method of removing an RNA fraction with ≥200 nucleotides in length from a whole blood sample. The present invention also relates to a method of purifying an RNA fraction with <200 nucleotides in length from a whole blood sample. The present invention further relates to a method of determining the level of RNA molecules with <200 nucleotides in length. In addition, the present invention relates to a method for diagnosing a disease in an individual. Moreover, the present invention relates to a kit which is useful for carrying out the methods of the present invention.

BACKGROUND OF THE INVENTION

Whole blood samples are used for molecular biological analyses, e.g. in order to determine whether a patient suffers from a specific disease or not. These samples are often collected by sampling whole blood freezing and then processing the frozen blood later. Frozen blood requires a sample size of at least 200 µl. High costs are involved with the freezing transportation and processing of whole blood.

Therefore, the collection of whole blood samples using a bloodspot technique is preferred. It requires smaller sample volumes, typically 45-60 µl for humans, although evolving analytical techniques are using samples using 10-15 µl of human blood and smaller. Once sampling is complete, the blood spots are dried in air before transferring or mailing to labs for processing. Because the blood is dried, it is not considered hazardous. Thus no special precautions need be taken in handling or shipping. Once at the analysis site, the desired components, e.g. proteins or metabolites, are extracted from the dried blood spots into a supernatant which is then further analyzed, e.g. by liquid chromatography and/or mass spectrometry.

Today, biomarkers which are comprised in whole blood play a key role in early diagnosis, risk stratification, and therapeutic management of diseases. In particular, microRNAs (miRNAs) are biomarkers which are found in whole blood. They represent a group of regulatory elements that enable cells to fine-tune complex gene expression cascades in a wide range of biological processes, such as proliferation, differentiation, apoptosis, stress-response, and oncogenesis. They exist in blood as free circulating nucleic acids and in blood cells. This is due to the fact that miRNAs are expressed in blood cells or in diverse tissues which release the miRNAs into circulating blood.

At present, blood is collected using PaxGene blood RNA tubes in order to determine the level of RNA biomarkers such as miRNAs comprised therein. Great instrument-based and analytical effort is necessary to purify and isolate RNA biomarkers such as miRNAs comprised therein. In addition, this techniques are very time consuming and expensive.

There is, thus, a need for an improved method of blood preparation that reduces or eliminates one or more of the above errors and difficulties.

The inventors of the present invention assessed for the first time that the bloodspot technique is useful in order to reduce the complexity of a RNA fraction derived from a whole blood sample. In particular, the inventors of the present invention found that the bloodspot technique is valuable in order to remove RNA fractions with ≥200 nucleotides in length from a whole blood sample or to purify RNA fractions with <200 nucleotides in length (including miRNA) from a whole blood sample. The purified and/or isolated RNA fractions comprise RNA molecules. The inventors of the present invention further found that expression profiles of such purified and/or isolated RNA molecules, e.g. miRNA molecules, can be determined and that said expression profiles are of great quality. In addition, the inventors of the present invention found that the blood spot technique provides sample stability under different environmental conditions (e.g. temperature and/or humidity), provides technical stability and allows the diagnosis or differential diagnosis of an individual suffering from a disease.

SUMMARY OF THE INVENTION

In a first aspect, the present invention relates to a method of removing an RNA fraction with ≥200 nucleotides in length from a whole blood sample comprising the steps of:
(i) providing an absorbent probe comprising a hydrophilic polymeric material into which whole blood from the whole blood sample has been absorbed,
(ii) contacting the absorbent probe with a fluid (to reconstitute the whole blood), and
(iii) recovering the fluid from step (ii), thereby removing the RNA fraction with ≥200 nucleotides in length.

In a second aspect, the present invention relates to a method of purifying an RNA fraction with <200 nucleotides in length from a whole blood sample comprising the steps of:
(i) providing an absorbent probe comprising a hydrophilic polymeric material into which whole blood from the whole blood sample has been absorbed,
(ii) contacting the absorbent probe with a fluid (to reconstitute the whole blood), and
(iii) recovering the fluid from step (ii), thereby purifying the RNA fraction with <200 nucleotides in length.

In a third aspect, the present invention relates to a method of determining the level of RNA molecules with <200 nucleotides in length comprising the steps of:
(i) carrying out the method of the second aspect, and
(ii) determining the level of RNA molecules with <200 nucleotides in length by a suitable technique.

In a fourth aspect, the present invention relates to a method for diagnosing a disease in an individual comprising the steps of:
(i) carrying out the method according to the second aspect, wherein the whole blood sample is from an individual,
(ii) determining the level of RNA molecules with <200 nucleotides in length by a suitable technique,
(iii) comparing said level to one or more reference level(s), and
(iv) diagnosing or differentially diagnosing whether the individual is afflicted by the disease based on the comparison.

Said fourth aspect may alternatively be formulated as follows: A method for diagnosing a disease in an individual comprising the steps of:
(i) carrying out the method according to the third aspect, wherein the whole blood sample is from an individual,
(ii) comparing said level to one or more reference level(s), and
(iii) diagnosing or differentially diagnosing whether the individual is afflicted by the disease based on the comparison.

In a fifth aspect, the present invention relates to the use of a hydrophilic polymeric material for removing an RNA fraction with ≥200 nucleotides in length from a whole blood sample.

In a sixth aspect, the present invention relates to the use of a hydrophilic polymeric material for purifying an RNA fraction with <200 nucleotides in length from a whole blood sample.

In a seventh aspect, the present invention relates to the use of a method according to the third aspect for diagnosing or differentially diagnosing a disease.

In an eight aspect, the present invention relates to a kit comprising
(i) an absorbent probe comprising a hydrophilic polymeric material.

In a ninth aspect, the present invention relates to a kit comprising
(i) a fluid to reconstitute whole blood absorbed into an absorbent probe comprising a hydrophilic polymeric material.

This summary of the invention does not necessarily describe all features of the present invention. Other embodiments will become apparent from a review of the ensuing detailed description.

DETAILED DESCRIPTION OF THE INVENTION

Definitions

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention. In the event of a conflict between the definitions or teachings of such incorporated references and definitions or teachings recited in the present specification, the text of the present specification takes precedence.

The term "comprise" or variations such as "comprises" or "comprising" according to the present invention means the inclusion of a stated integer or group of integers but not the exclusion of any other integer or group of integers. The term "consisting essentially of" according to the present invention means the inclusion of a stated integer or group of integers, while excluding modifications or other integers which would materially affect or alter the stated integer. The term "consisting of" or variations such as "consists of" according to the present invention means the inclusion of a stated integer or group of integers and the exclusion of any other integer or group of integers.

The terms "a" and "an" and "the" and similar reference used in the context of describing the invention (especially in the context of the claims) are to be construed to cover both the singular and the plural, unless otherwise indicated herein or clearly contradicted by context.

The term "nucleotides", as used herein, refers to organic molecules that serve as the monomers, or subunits, of nucleic acids like DNA (deoxyribonucleic acid) and RNA (ribonucleic acid). The building blocks of nucleic acids, nucleotides are composed of a nitrogenous base, a five-carbon sugar (ribose or deoxyribose), and at least one phosphate group. Thus a nucleoside plus a phosphate group yields a nucleotide.

The term "RNA fraction with ≥200 nucleotides in length", as used herein, refers to an RNA portion which comprises large RNA molecules, namely one or more RNA molecules having a length of ≥200 nucleotides. The one or more RNA molecules encompass ribosomal RNA (rRNA) molecules. They may be selected from the group consisting of ribosomal 18S RNA and ribosomal 28S RNA.

In the context of the present invention, term "ribosomal ribonucleic acid (abbreviated rRNA)" refers to the RNA component of the ribosome, and is essential for protein synthesis in all living organisms. It constitutes the predominant material within the ribosome, which is approximately 60% rRNA and 40% protein by weight. Ribosomes contain two major rRNAs and 50 or more proteins. The ribosomal RNAs form two subunits, the large subunit (LSU) and small subunit (SSU). The large subunit encompasses the ribosomal 28S RNA and the small subunit encompasses the ribosomal 18S RNA.

The term "RNA fraction with <200 nucleotides in length", as used herein, refers to an RNA portion which comprises small RNA molecules, namely one or more RNA molecules having a length of <200 nucleotides in length. The one or more RNA molecules may be selected from the group consisting of miRNA, tRNA, siRNA, piRNA, and snorRNA.

The term "microRNA (abbreviated miRNA)" refers to single-stranded RNA molecules having a length of at least 10 nucleotides and of not more than 40 nucleotides. The nucleotides are covalently linked together. For example, the single-stranded RNA molecules have a length of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides. The miRNAs regulate gene expression and are encoded by genes from whose DNA they are transcribed but miRNAs are not translated into protein (i.e. miRNAs are non-coding RNAs). The genes encoding miRNAs are longer than the processed mature miRNA molecules. The miRNAs are first transcribed as primary transcripts or pri-miRNAs with a cap and poly-A tail and processed to short, 70 nucleotide stem-loop structures known as pre-miRNAs in the cell nucleus. This processing is performed in animals by a protein complex known as the Microprocessor complex consisting of the nuclease Drosha and the double-stranded RNA binding protein Pasha. These pre-miRNAs are then processed to mature miRNAs in the cytoplasm by interaction with the endonuclease Dicer, which also initiates the formation of the RNA-induced silencing complex (RISC). When Dicer cleaves the pre-miRNA stem-loop, two complementary short RNA molecules are formed, but only one is integrated into the RISC. This strand is known as the guide strand and is selected by the argonaute protein, the catalytically active RNase in the RISC, on the basis of the stability of the 5' end. The remaining strand, known as the miRNA*, anti-guide (anti-strand), or passenger strand, is degraded as a RISC substrate. Therefore, the miRNA*s are derived from the same hairpin structure like the "normal" miRNAs. So if the "normal" miRNA is then later called the "mature miRNA" or "guide strand", the miRNA* is the "anti-guide strand" or "passenger strand".

The term "transfer RNA (abbreviated tRNA)", as used herein, refers to an adaptor molecule composed of RNA, typically 76 to 90 nucleotides in length that serves as the physical link between the mRNA and the amino acid sequence of proteins. It does this by carrying an amino acid to the protein synthetic machinery of a cell (ribosome) as directed by a three-nucleotide sequence (codon) in a messenger RNA (mRNA). As such, tRNAs are a necessary component of translation, the biological synthesis of new proteins according to the genetic code.

The term "small interfering RNA (abbreviated siRNA)", as used herein, refers to a class of double-stranded RNA molecules, 20-25 base pairs in length. siRNA plays many roles, but it is most notable in the RNA interference (RNAi) pathway, where it interferes with the expression of specific genes with complementary nucleotide sequences. siRNA functions by causing mRNA to be broken down after transcription, resulting in no translation.

The term "piwi-interacting RNA (abbreviated piRNA)", as used herein, refer to the largest class of small non-coding RNA molecules expressed in animal cells. piRNAs form RNA-protein complexes through interactions with piwi proteins. These piRNA complexes have been linked to both epigenetic and post-transcriptional gene silencing of retrotransposons and other genetic elements in germ line cells, particularly those in spermatogenesis. They are distinct from microRNA (miRNA) in size (26-31 nt rather than 21-24 nt), lack of sequence conservation, and increased complexity.

The term, "small nucleolar RNA (abbreviated snoRNAs)", as used herein, refers to a class of small RNA molecules that primarily guide chemical modifications of other RNAs, mainly ribosomal RNAs, transfer RNAs and small nuclear RNAs. There are two main classes of snoRNA, the C/D box snoRNAs, which are associated with methylation, and the H/ACA box snoRNAs, which are associated with pseudouridylation. SnoRNAs are commonly referred to as guide RNAs but should not be confused with the guide RNAs that direct RNA editing in trypanosomes.

The term "whole blood" as used herein, refers to non-fractionated blood. It, thus, comprises all blood components. Whole blood is made up of an acellular fluid (plasma or serum) and a mixture of multiple blood cell types. The three primary blood cell types are red blood cells (erythrocytes), white blood cells (leukocytes), and platelets (thrombocytes). Each type contributes a different amount of RNA to the total RNA in blood.

The terms "red blood cells (RBC)" and "erythrocytes", as used herein, refer to the most abundant cells in whole blood, constituting 44% of the blood volume. Mature RBCs lose their nucleus and organelles during maturation and, thus, do not contribute any RNA to the total blood RNA pool. However, immature RBCs, also known as reticulocytes, may retain some residual nucleic acids. Because reticulocytes constitute about 1% of the RBC population, residual RNA from reticulocytes contributes up to 70% of the RNA in the total blood RNA pool.

The terms "white blood cells (WBC)" and "leukocytes", as used herein, refer to nucleated blood cells that carry out the immune functions of the body. Leukocytes are the most transcriptionally active cells in blood. Leukocytes are made up of granulocytes, lymphocytes, and monocytes. Granulocytes can be further divided into neutrophils, basophils, and eosinophils. Lymphocytes can be divided into B-cells, T-cells, and natural killer (NK) cells. The number of cells in each leukocyte subtype can change significantly during disease states such as inflammation and leukemia.

The terms "platelets" and "thrombocytes", as used herein, refer to blood cells playing a major role in blood clotting. Platelets enter the blood circulation by fragmentation of large bone marrow cells called megakaryocytes. Like red blood cells, platelets lack a nucleus and organelles. Immature platelets, called reticulated platelets, contain residual RNA from megakaryocytes. Up to 4.5% of platelet counts can be reticulated platelets. Platelet RNA, therefore, also contributes to the total RNA blood pool.

The term "plasma", as used herein, refers to the pale yellow liquid component of blood that normally holds the blood cells in whole blood in suspension. This makes plasma the extracellular matrix of blood cells. It is a fluid which is composed of about 92% water, 7% vital proteins such as albumin, gamma globulin, anti-hemophilic factor, and other clotting factors, and 1% mineral salts, sugars, fats, hormones and vitamins.

The term "serum", as used herein, refers to the blood component that is neither a blood cell (serum does not contain white or red blood cells) nor a clotting factor. It is the blood plasma not including the fibrinogens. Serum includes all proteins not used in blood clotting (coagulation) and all the electrolytes, antibodies, antigens, hormones, and any exogenous substances (e.g., drugs and microorganisms).

The term "whole blood sample", as used herein, refers to blood material which is not part of the body of an individual anymore. A whole blood sample may be provided by removing blood from an individual, but may also be provided by using previously isolated blood material. The whole blood sample may be removed from an individual using conventional blood collection techniques. For example, the whole blood may be extracted from a vein in the arm of an individual using a needle, or via finger prick. Thus, the whole blood sample may have the form of a blood drop. Said blood drop may be on an individual, e.g. on a fingertip of the individual. The whole blood sample may also be comprised in a blood collection tube, e.g. capillary tube, or in a pipette tip.

The term "blood spot" refers to a filter paper comprising one or more blood drops. Usually, the filter paper comprising the one or more blood drops is dried after sampling. The inventors of the present invention used a hydrophilic polymeric material to absorb the blood drops.

The term "blood spot technique" refers to a form of biosampling where blood samples are blotted on filter paper. After the biosampling, the filter paper comprising the blood is preferably dried. The dried samples can easily be shipped to an analytical laboratory and analyzed using various methods such as RNA expression analysis. In particular, blood spot specimens are collected by applying a few drops of blood, drawn by lancet from the finger, heel or toe, onto absorbent filter paper. The blood is allowed to thoroughly saturate the paper and is preferably air dried. Specimens may be stored in low gas-permeability plastic bags with desiccant added to reduce humidity, and may be kept at ambient temperature, even in tropical climates. Once in the laboratory, technicians may separate a small disc of saturated paper from the sheet using an automated or manual hole punch for further analysis. As an alternative to punching out a paper disc, recent automation solutions may extract the sample by flushing an eluent through the filter without punching it out. The inventors of the present invention used a hydrophilic polymeric material onto which the blood is blotted/applied.

The term "individual" as used herein, refers to any subject from which a whole blood sample can be taken, obtained, or isolated.

The term "individual", as used herein, further refers to any subject for whom it is desired to know whether she or he suffers from a disease. In particular, the term "individual", as used herein, refers to a subject suspected to be affected by a disease. The individual may be diagnosed to be affected by the disease, i.e. diseased, or may be diagnosed to be not affected by the disease, i.e. healthy. The term "individual", as used herein, also refers to a subject which is affected by the disease, i.e. diseased. The patient may be retested for the disease and may be diagnosed to be still affected by the disease, i.e. diseased, or not affected by the disease anymore, i.e. healthy, for example after therapeutic intervention. It should be noted that a patient that is diagnosed as being healthy, i.e. not suffering from the disease, may possibly suffer from another disease not tested/known. The disease may be lung cancer. The individual for whom it is desired to know whether she or he suffers from a disease may also be designated as patient.

The individual may be a mammal, including both a human and another mammal, e.g. an animal such as a rodent, a rabbit, or a monkey. The rodent may be a mouse, rat, hamster, guinea pig, or chinchilla.

The term "(control) subject", as used herein, refers to a subject known to be affected by a disease (positive control), i.e. diseased. The term "(control) subject", as used herein, also refers to a subject known to be not affected by a disease (negative control), i.e. healthy. Thus, the term "healthy subject", as used herein, means a subject which is known to be not affected by a disease. It should be noted that a (control) subject which is known to be healthy, i.e. not suffering from the disease tested/known, may possibly suffer from another disease not tested/known. The disease may be lung cancer.

The (control) subject may be a mammal, including both a human and another mammal, e.g. an animal such as a rodent, a rabbit, or a monkey. The rodent may be a mouse, rat, hamster, guinea pig, or chinchilla.

The term "diagnosing a disease", as used herein, means determining whether an individual shows signs of or suffers from the disease. Preferably, the disease is lung cancer. The term "differentially diagnosing a disease", as used herein, means determining whether an individual shows the signs of or suffers from a disease or shows the signs of or suffers from another disease. Preferably, the disease is lung cancer. The other disease is any other disease than lung cancer. "Differentially diagnosing a disease", as used in the context of the present invention, may also allow to distinguish differently treated diseases from each other. For example, the disease may be an adjuvant-treated disease, e.g. adjuvant-treated lung cancer, and the other disease may be a palliative-treated disease, e.g. palliative-treated lung cancer, or the disease may be a palliative-treated disease, e.g. palliative-treated lung cancer, and the other disease may be an adjuvant-treated disease, e.g. adjuvant-treated lung cancer.

The term "treatment", in particular "therapeutic treatment", as used herein, refers to any therapy which improves the health status and/or prolongs (increases) the lifespan of an individual. Said therapy may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease. The therapeutic treatment may be a treatment of lung cancer. The therapeutic treatment of lung cancer is selected from the group consisting of chemotherapy, surgery, radiotherapy, adjuvant therapy, and palliative therapy.

The term "absorbent probe", as used herein, refers to any probe which can absorb whole blood comprised in the whole blood sample. The absorbent probe used herein comprises, essentially consists of, or consists of a hydrophilic polymeric material.

The term "hydrophilic polymeric material", as used herein, refers to any material which can absorb whole blood comprised in the whole blood sample. The term "hydrophilic polymeric material", as used herein, further refers to a polymeric material which contains polar or charged functional groups, rendering the material soluble in water. A hydrophilic polymeric material comprises hydrophilic polymers. A hydrophilic polymer is produced from two or more hydrophilic monomers. The term "hydrophilic polymeric material", as used herein, also encompasses a polymeric material which is not hydrophilic by nature, e.g. polyethylene, but which has been rendered hydrophilic. If the polymeric material is not initially hydrophilic, then there are numerous methods for converting the material into a hydrophilic state. Methods for creating hydrophilic surfaces include adsorptive treatment with surfactants such as Tween-40 or Tween-80 to create hydrophilic surfaces. Treatment may also occur with other molecules containing both hydrophilic and hydrophobic elements. The hydrophobic elements will interact strongly with the hydrophobic polymeric material and expose the hydrophilic elements creating hydrophilic surfaces. Additionally treatment with plasma (Corona, Air, Flame, or Chemical) is another well-known method of adding polar groups to the surfaces of such materials, including oxygen plasma treatments. Likewise, the grafting of hydrophilic polymers to the surface and the chemical functionalization of active groups on the surface with polar or hydrophilic molecules such as sugars can be used to achieve a hydrophilic surface on a polymeric material. Covalent modification could also be used to add polar or hydrophilic functional groups to the surface of a polymeric material.

The hydrophilic polymeric material may be selected from the group consisting of a cellulose comprising material, e.g. cotton, a polysaccharide, a polyolefin, and a polyester, or modifications thereof. The polysaccharide may be cellulose, the polyolefin may be selected from the group consisting of polyethylene, polypropylene, polybutylene, polyisobutylene, and polymethylpentene, and the polyester may be selected from the group consisting of polycarbonate and polyethylenterephthalate. Cotton, cellulose, and polyethylene as hydrophilic polymeric materials are particularly preferred.

Examples of devices/probes comprising a hydrophilic polymeric material include, but are not limited to, Mitra Microsampling Device (neoteryx, Torrance, Calif., USA), Non-Indicating FTA Classic Card (GE Healthcare Life Science, Buckinghamshire, Great Britain), Non-Indicating FTA Elute Micro Card (GE Healthcare Life Science, Buckinghamshire, Great Britain), HemaSpot HF (Spot On Sciences, Austin, Tex., USA), HemaSpot SE (Spot On Sciences, Austin, Tex., USA), TFN (Munktell, Bärenstein, Germany), and TFN-Di (Munktell, Bärenstein, Germany).

The term "level", as used herein, refers to an amount (measured for example in grams, mole, or ion counts) or concentration (e.g. absolute or relative concentration) of RNA molecules with <200 nucleotides in length. The term "level", as used herein, also comprises scaled, normalized, or scaled and normalized amounts or values. In one embodiment, the level is the expression level of RNA molecules with <200 nucleotides in length. Said expression level may be indicated as (relative) RNA (e.g. miRNA) concentration, (relative) RNA (e.g. miRNA) amount, or (relative) RNA (e.g. miRNA) extinction units such as relative fluorescence units.

In the context of the present invention, the term "kit of parts (abbreviated kit)" is understood to be any combination of at least some of the components identified herein, which are combined, coexisting spatially, to a functional unit, and which can contain further components.

Embodiments of the Invention

The present invention will now be further described. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous, unless clearly indicated to the contrary.

The inventors of the present invention assessed for the first time that the bloodspot technique is useful in order to reduce the complexity of a whole blood sample. In particular, the inventors of the present invention found that the bloodspot technique is valuable in order to remove RNA fractions with ≥200 nucleotides in length from a whole blood sample or to purify RNA fractions with <200 nucleotides in length (including miRNA) from a whole blood sample. The purified and/or isolated RNA fractions comprise RNA molecules. The inventors of the present invention further found that expression profiles of such purified and/or isolated RNA molecules, e.g. miRNA molecules, can be determined and that said expression profiles are of great quality. In addition, the inventors of the present invention found that the blood spot technique provides sample stability under different environmental conditions (e.g. temperature and/or humidity), provides technical stability and allows the diagnosis or differential diagnosis of an individual suffering from a disease.

Thus, in a first aspect, the present invention relates to a method of removing an RNA fraction with ≥200 nucleotides in length from a whole blood sample comprising the steps of:
(i) providing an absorbent probe comprising, essentially consisting of, or consisting of a hydrophilic polymeric material into which whole blood from the whole blood sample has been absorbed,
(ii) contacting the absorbent probe with a fluid (to reconstitute the whole blood), and
(iii) recovering the fluid from step (ii), thereby removing the RNA fraction with ≥200 nucleotides in length.

In step (i), an absorbent probe is provided, which comprises, essentially consists of, or consists of a hydrophilic polymeric material into which whole blood from the whole blood sample has been absorbed. Therewith, RNA molecules with ≥200 nucleotides in length as well as RNA molecules with <200 nucleotides in length which are comprised in the whole blood have been absorbed into the hydrophilic polymeric material.

The absorbent probe provided in step (i) may be obtained by placing an absorbent probe comprising, essentially consisting of, or consisting of a hydrophilic polymeric material in (physical) contact with the whole blood sample, thereby absorbing whole blood into the hydrophilic polymeric material.

A (physical) contact between the absorbent probe and the whole blood sample may be achieved by dipping or immersing the absorbent probe into the whole blood sample. The whole blood sample may have the form of a blood drop. The whole blood may also be comprised in a blood collection tube. Alternatively, one or more drops of the whole blood sample may be applied to the absorbent probe, e.g. via a pipette. Due to the (physical) contact, the whole blood is soaked into the hydrophilic polymeric material and therewith the RNA molecules with ≥200 nucleotides in length as well as RNA molecules with <200 nucleotides in length which are comprised in the whole blood.

Normally, it is sufficient to maintain the probe in (physical) contact with the whole blood sample for between 1 to 20 seconds, preferably for between 1 to 10 seconds, more preferably for between 1 to 5 seconds, e.g. for 1, 2, 3, 4, 5, 6, 7, 8, 9, 10, 11, 12, 13, 14, 15, 16, 17, 18, 19, or 20 seconds. The contact time is desirably as short as possible. The probe absorbs a predetermined volume of blood during that time and, once saturated, does not absorb more blood. The size and shape of the probe can be varied to adjust the volume of absorbed blood and rate of absorption. Blood volumes of between 1 to 50 µl, preferably of between 5 to 25 µl, and even more preferably of between 10 to 20 µl, e.g. of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 µl, are believed suitable.

In step (ii), the absorbent probe is contacted with a fluid. The fluid may be a liquid or gas. Preferably, the fluid is a chaotropic fluid, e.g. a chaotropic liquid or gas. More preferably, the chaotropic fluid is selected from the group consisting of guanidinium thiocyanate, guanidinium isothiocyanate, guanidinium hydrochloride, guanidinium chloride, alkali thiocyanate, alkali isothiocyanate, alkali iodide, and alkali perchlorate. Even more preferably, the chaotropic fluid is guanidinium thiocyanate. Alternatively, the chaotropic fluid, e.g. the chaotropic liquid or gas, may comprise guanidinium thiocyanate, guanidinium isothiocyanate, guanidinium hydrochloride, guanidinium chloride, alkali thiocyanate, alkali isothiocyanate, alkali iodide, and alkali perchlorate. Preferably, the chaotropic fluid comprises guanidinium thiocyanate.

A contact between the absorbent probe and the fluid may be achieved by dipping or immersing the absorbent probe into the fluid. This can be done by hand or by a fluid handling robot. Step (ii) allows to reconstitute the whole blood. Physical agitation techniques such as sonication, mixing, or vortexing of the fluid and/or the absorbent probe can accelerate the reconstitution process. In particular, step (ii) allows the separation of molecules comprised in the whole blood from each other. Some molecules can be removed from the hydrophilic polymeric material, other molecules cannot. These molecules remain absorbed into the hydrophilic polymeric material. The inventors of the present invention surprisingly found that RNA molecules with >200 nucleotides in length remain absorbed into the hydrophilic polymeric material and do not enter the fluid, while RNA molecules with <200 nucleotides in length can be extracted from the hydrophilic polymeric material by the fluid in step (ii).

In step (iii) the fluid is recovered from step (ii). Due to this process, the RNA fraction with ≥200 nucleotides in length is removed. In this respect, it should be noted that the removal of the RNA fraction with ≥200 nucleotides in length does not necessarily mean that the RNA fraction with ≥200 nucleotides in length is completely removed. The present invention also covers embodiments, wherein at least a part of the RNA molecules with ≥200 nucleotides in length is removed. For example, in some embodiments, at least 10, 20, 30, 40, 50, 60, 70, 80, 90, 95, 96, 97, 98, 99%, or 100% of the RNA molecules with ≥200 nucleotides in length are removed. It is preferred that at least 90% of the RNA molecules with ≥200 nucleotides in length are removed. It is more preferred that at least 95% of the RNA molecules with ≥200 nucleotides in length are removed. It is even more preferred that at least 98% or 99% of the RNA molecules with ≥200 nucleotides in length are removed. It is most preferred that 100% of the RNA molecules with >200 nucleotides in length, i.e. all RNA molecules with ≥200 nucleotides in length, are removed. The recovering of the fluid from step (ii) may be achieved by removing the absorbent probe from the fluid.

Preferably, the RNA fraction with ≥200 nucleotides in length comprises one or more RNA molecules selected from the group consisting of ribosomal 18S RNA and ribosomal 28S RNA.

In a second aspect, the present invention relates to a method of purifying an RNA fraction with <200 nucleotides in length from a whole blood sample comprising the steps of:
(i) providing an absorbent probe comprising, essentially consisting of, or consisting of a hydrophilic polymeric material into which whole blood from the whole blood sample has been absorbed,
(ii) contacting the absorbent probe with a fluid (to reconstitute the whole blood), and
(iii) recovering the fluid from step (ii), thereby purifying the RNA fraction with <200 nucleotides in length.

In step (i), an absorbent probe is provided, which comprises, essentially consists of, or consists of a hydrophilic polymeric material into which whole blood from the whole blood sample has been absorbed. Therewith, RNA molecules with ≥200 nucleotides in length as well as RNA molecules with <200 nucleotides in length which are comprised in the whole blood has been absorbed into the hydrophilic polymeric material.

The absorbent probe provided in step (i) may be obtained by placing an absorbent probe comprising, essentially consisting of, or consisting of a hydrophilic polymeric material in (physical) contact with the whole blood sample, thereby absorbing whole blood into the hydrophilic polymeric material, A (physical) contact between the absorbent probe and the whole blood sample may be achieved by dipping or immersing the absorbent probe into the whole blood sample. The whole blood sample may have the form of a blood drop. The whole blood may also be comprised in a blood collection tube. Alternatively, one or more drops of the whole blood sample may be applied to the absorbent probe, e.g. via a pipette. Due to the (physical) contact, the whole blood is soaked into the hydrophilic polymeric material and therewith the RNA molecules with ≥200 nucleotides in length as well as RNA molecules with <200 nucleotides in length which are comprised in the whole blood.

Normally, it is sufficient to maintain the probe in (physical) contact with the whole blood sample for between 1 to 20 seconds, preferably for between 1 to 10 seconds, more preferably of between 1 to 5 seconds, e.g. 1, 2, 3, 4, 5, 6, 7, 8, 9, 10, 11, 12, 13, 14, 15, 16, 17, 18, 19, or 20 seconds. The contact time is desirably as short as possible. The probe absorbs a predetermined volume of blood during that time and, once saturated, does not absorb more blood. The size and shape of the probe can be varied to adjust the volume of absorbed blood and rate of absorption. Blood volumes of between 1 to 50 µl, preferably of between 5 to 25 µl, even more preferably of between 10 to 20 µl, e.g. of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 µl, are believed suitable.

In step (ii), the absorbent probe is contacted with a fluid. The fluid may be a liquid or gas. Preferably, the fluid is a chaotropic fluid, e.g. a chaotropic liquid or gas. More preferably, the chaotropic fluid is selected from the group consisting of guanidinium thiocyanate, guanidinium isothiocyanate, guanidinium hydrochloride, guanidinium chloride, alkali thiocyanate, alkali isothiocyanate, alkali iodide, and alkali perchlorate. Even more preferably, the chaotropic fluid is guanidinium thiocyanate. Alternatively, the chaotropic fluid, e.g. the chaotropic liquid or gas, may comprise guanidinium thiocyanate, guanidinium isothiocyanate, guanidinium hydrochloride, guanidinium chloride, alkali thiocyanate, alkali isothiocyanate, alkali iodide, and alkali perchlorate. Preferably, the chaotropic fluid comprises guanidinium thiocyanate.

A contact between the absorbent probe and the fluid may be achieved by dipping or immersing the absorbent probe into the fluid. This can be done by hand or by a fluid handling robot. Step (ii) allows to reconstitute the whole blood. Physical agitation techniques such as sonication or vortexing of the fluid and/or the absorbent probe can accelerate the reconstitution process. In particular, step (ii) allows the separation of molecules comprised in the whole blood from each other. Some molecules can be removed from the hydrophilic polymeric material, other molecules cannot. These molecules remain absorbed into the hydrophilic polymeric material. The inventors of the present invention surprisingly found that RNA molecules with ≥200 nucleotides in length remain absorbed into the hydrophilic polymeric material and does not enter the fluid, while RNA molecules with <200 nucleotides in length can be removed from the hydrophilic polymeric material by the fluid in step (ii).

In step (iii) the fluid is recovered from step (ii). Due to this process, the RNA fraction with <200 nucleotides in length is purified. It is particularly purified from the aqueous phase of the reconstituted blood sample. Preferably, the purified RNA fraction with <200 nucleotides in length has a purity of at least 50% or at least 60%, more preferably of at least 70%, even more preferably of at least 80%, and most preferably of at least 90,%, e.g. at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.9%, or 100%.

The recovering of the fluid from step (ii) may be achieved by removing the absorbent probe from the fluid.

Preferably, the RNA fraction with <200 nucleotides in length comprises one or more RNA molecules selected from the group consisting of miRNA, tRNA, siRNA, piRNA, and snorRNA.

In one embodiment of the first and second aspect of the present invention, the absorbent probe is contacted with the fluid for ≤20 hours, preferably for ≤5 hours, e.g. for ≤1, 2, 3, 4, 5, 6, 7, 8, 9, 10, 11, 12, 13, 14, 15, 16, 17, 18, 19, 20, 21, 22, 23, 24, 25, 26, 27, 28, 29 minute(s), 0.5, 1, 1.5, 2, 2.5, 3, 3.5, 4, 4.5, 5, 6, 7, 8, 9, 10, 11, 12, 13, 14, 15, 16, 17, 18, 19, or 20 hour(s). More preferably, the absorbent probe is contacted with the fluid for between 1 minute and 20 hours, even more preferably for between 1 minute and 5 hours, e.g.

for 1, 2, 3, 4, 5, 6, 7, 8, 9, 10, 11, 12, 13, 14, 15, 16, 17, 18, 19, 20, 21, 22, 23, 24, 25, 26, 27, 28, 29 minute(s), 0.5, 1, 1.5, 2, 2.5, 3, 3.5, 4, 4.5, 5, 6, 7, 8, 9, 10, 11, 12, 13, 14, 15, 16, 17, 18, 19, or 20 hour(s).

In one embodiment of the first and second aspect of the present invention, the hydrophilic polymeric material has a density of $\leq 6$ g/cm$^3$, preferably of $\leq 4$ g/cm$^3$, e.g. of 0.5, 1.5, 2, 2.5, 3, 3.5, 4, 4.5, 5, 5.5, or 6 g/cm$^3$. More preferably, the hydrophilic polymeric material has a density of between 0.5 and 6 g/cm$^3$, even more preferably of between 1 and 4 g/cm$^3$, e.g. of 0.5, 1.5, 2, 2.5, 3, 3.5, 4, 4.5, 5, 5.5, or 6 g/cm$^3$.

In one embodiment of the first and second aspect of the present invention, the hydrophilic polymeric material is porous.

In one embodiment of the first and second aspect of the present invention, the hydrophilic polymeric material has a pore volume of between 20 and 70%, preferably of between 30 and 50%, e.g. of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70% of the total volume of the material.

In one embodiment of the first and second aspect of the present invention, the hydrophilic polymeric material comprises pores that are $\leq 100$ μm, preferably $\leq 50$ μm, e.g. $\leq 10$, 15, 20, 25, 30, 35, 40, 45, 50, 55, 60, 65, 70, 75, 80, 85, 90, 95, or 100 μm, in diameter or largest cross-sectional dimension. More preferably, the hydrophilic polymeric material comprises pores that are between 10 to 100 μm, even more preferably between 20 and 50 μm, e.g. 10, 15, 20, 25, 30, 35, 40, 45, 50, 55, 60, 65, 70, 75, 80, 85, 90, 95, or 100 μm, in diameter or largest cross-sectional dimension.

In one embodiment of the first and second aspect of the present invention, the hydrophilic polymeric material is selected from the group consisting of a cellulose comprising material, e.g. cotton, a polysaccharide, a polyolefin, and a polyester. Preferably,
(i) the polysaccharide is cellulose,
(ii) the polyolefin is selected from the group consisting of polyethylene, polypropylene, polybutylene, polyisobutylene, and polymethylpentene, or
(iii) the polyester is selected from the group consisting of polycarbonate and polyethylenterephthalate.
More preferably, the hydrophilic polymeric material is cotton, cellulose or polyethylene.

In one embodiment of the first and second aspect of the present invention, the absorbent probe has absorbed a predetermined maximum volume of whole blood of between 1 to 50 μl, e.g. of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 μl.

In one embodiment of the first and second aspect of the present invention, the absorbent probe has a length of $\leq 10$ mm, preferably of $\leq 5$ mm, e.g. of $\leq 2$, 2.5, 3, 3.5, 4, 4.5, 5, 5.5, 6, 6.5, 7, 7.5, 8, 8.5, 9, 9.5, or 10 mm, and a cross-sectional area of $\leq 40$ mm$^2$, preferably of $\leq 20$ mm$^2$, e.g. of $\leq 5$, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 mm$^2$.

Such sizes are believed suitable when the whole blood sample is a blood drop, e.g. from a finger prick.

In an alternative embodiment of the first and second aspect of the present invention the absorbent probe has a volume of $\leq 250$ mm$^3$, preferably of $\leq 200$ mm$^3$, e.g. of $\leq 1$, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, 200, 210, 220, 230, 240, or 250 mm$^3$.

Such volumes are believed suitable when the whole blood sample is a blood drop, e.g. from a finger prick.

More preferably, the absorbent probe has a length of between 2 and 10 mm, preferably of between 2 and 5 mm, e.g. of 2, 2.5, 3, 3.5, 4, 4.5, 5, 5.5, 6, 6.5, 7, 7.5, 8, 8.5, 9, 9.5, or 10 mm, and a cross-sectional area of between 5 and 40 mm$^2$, preferably of between 5 and 20 mm$^2$, e.g. of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 mm$^2$.

In an alternative embodiment of the first and second aspect of the present invention the absorbent probe has a volume of between 1 mm$^3$ to 250 mm$^3$, preferably of between 2.5 mm$^3$ to 200 mm$^3$, e.g. of 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, 200, 210, 220, 230, 240, or 250 mm$^3$.

Flat ended cylinders or semicircular ends on cylindrical probes are believed desirable, but various configurations may be used.

In one embodiment of the first and second aspect of the present invention, the whole blood absorbed into the hydrophilic polymeric material has been dried. Drying may be carried out in the open air, e.g. at room temperature (20° C.) or elevated temperatures (e.g. 30° C.). Alternatively, the absorbent probe may be transferred to a special drying container configured to help drying while minimizing the contact between the absorbent probe and the walls of the drying container or other potential contaminant surfaces. The drying container may comprise a desiccant to facilitate drying. Drying may be carried out for between 0.5 and 5 hour(s) or for between 0.5 and 3 hour(s), e.g. for 0.5, 1, 1.5, 2, 2.5, 3, 3.5, 4, 4.5, or 5 hour(s). In this respect, is should be noted that the drying time may vary as it depends on humidity, temperature, volume to be dried and the shape and configuration of the absorbent probe. In addition, drying the blood quickly helps to slow down blood sample degradation. Drying a small sample is faster than drying a large sample. To reduce drying time, the hydrophilic material is preferably selected to be air permeable or gas permeable so that air can enter the absorbent probe and dry it faster.

The fluid may be separated from the absorbent probe for further processing (e.g. concentrating) or analysis (e.g. microarray analysis), while the absorbent probe may be discarded. Thus, in one embodiment of the second aspect of the present invention, the method further comprises the step of:
(iv) isolating the RNA fraction with <200 nucleotides in length by one or more separation techniques.

It is preferred that the one or more separation techniques are selected from the group consisting of centrifugation, evaporation/reconstitution, concentration, precipitation, liquid/liquid extraction, and solid phase extraction.

Due to this isolation step, the purity of the RNA fraction with <200 nucleotides in length can be further improved. It is particularly preferred that the isolated RNA fraction with <200 nucleotides in length has a purity of at least 70% or at least 75%, more preferably of at least 80%, even more preferably of at least 90%, and most preferably of at least 95,%, e.g. at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.9%, or 100%.

In one embodiment of the first and second aspect of the present invention, the absorbent probe further comprises a substance selected from the group consisting of a reference standard, an anti-coagulant, and a stabilizer.

The use of anticoagulants may be useful in maintaining the homogeneity of the blood as well as preventing unwanted degradation. An anticoagulant may be applied dry to the absorbent probe, but is preferably applied wet or in liquid form and allowed to dry before use. The most common anticoagulants fall into two categories polyanions (e.g. Heparin) or metal chelators (e.g. EDTA, citrate). Suitable anticoagulants are believed to include acid citrate dextrose, citrate phosphate dextrose, citrate phosphate dextrose adenine, sodium citrate, K2 EDTA, K3 EDTA, sodium EDTA, lithum heparin, sodium heparin, potassium and oxalate. Any anticoagulant applied to the absorbent probe should be suitably matched with the fluid used and the downstream analysis so as not to adversely affect the accuracy of the analysis.

The use of a reference standard, e.g. internal and external standard, during analysis is common practice. Thus, a reference standard (wet or dried) may be applied to the absorbent probe during manufacture or sampling of the fluid, or it may be added to the reconstituting fluid when the (dried) blood is extracted from the absorbent probe. Many non-volatile materials which do not affect the analysis of the blood may be used as reference standards. Radiolabels, fluorescent labels, and deuterated labels may be used.

The use of stabilizers is also common practice. Stabilizers may be useful in stabilizing the blood. A stabilizer may be applied dry to the absorbent probe, but is preferably applied wet or in liquid form and allowed to dry before use. Examples of stabilizers include, but are not limited to, RNA-later, RNAstable, PAXgene-reagent, RNAsin, and catrimox-14.

In one embodiment of the first and second aspect of the present invention, the absorbent probe is a probe as described in WO 2013/067520 A1 or US 2013116597 A1. In particular, the absorbent probe is part of a biological fluid sampling device as described in WO 2013/067520 A1 or US 2013116597 A1. In this respect, it is referred to page 10, line 28 to page 34, line 27, FIGS. 2, 3 and 8, and claims 1 to 19 of WO 2013/067520 A1 and to paragraphs [0068] to [0129], FIGS. 2, 3 and 8, and claims 1 to 19 of US 2013116597 A1.

In a third aspect, the present invention relates to a method of determining the level of RNA molecules with <200 nucleotides in length comprising the steps of.
(i) carrying out the method of the second aspect, and
(ii) determining the level of RNA molecules with <200 nucleotides in length by a suitable technique.

The inventors of the present invention surprisingly found that the level of RNA molecules, e.g. miRNAs, purified/ isolated according to the second aspect of the present invention, can be determined. In this way, sample processing times can be shorten, sample analysis (e.g. due to expression profiling) can be simplified, and costs can be saved.

Preferably, the RNA molecules with <200 nucleotides in length are selected from the group consisting of miRNA, tRNA, siRNA, piRNA, and snoRNA.

In one embodiment of the third aspect of the present invention, the level which is determined in step (ii) is the expression level.

The determination in step (ii) may be carried out by any convenient means for determining the level of the RNA molecules, e.g. miRNAs, particularly the expression level of the RNA molecules, e.g. miRNAs. For example, qualitative, semi-quantitative, and/or quantitative detection methods may be used. A variety of techniques are well known to the person skilled in the art.

It is preferred that the level of the RNA molecules, e.g. miRNAs, particularly the expression level of the RNA molecules, e.g. miRNAs, is determined by nucleic acid hybridization, nucleic acid amplification, polymerase extension, sequencing, mass spectroscopy or any combination thereof.

Nucleic acid amplification may be performed using real time polymerase chain reaction (RT-PCR) such as real time quantitative polymerase chain reaction (RT qPCR). The real time polymerase chain reaction (RT-PCR) is preferred for the analysis of a single RNA molecule, e.g. a miRNA, or a low number of RNA molecules, e.g. miRNAs. It is particularly suitable for detecting low abundance RNA molecules, e.g. miRNAs. The real time quantitative polymerase chain reaction (RT qPCR), however, allows the analysis of a single RNA molecule, e.g. a miRNA, and a high number of RNA molecules, miRNAs.

A variety of kits and protocols to determine the expression level of miRNAs by real time polymerase chain reaction (RT-PCR) such as real time quantitative polymerase chain reaction (RT qPCR) are available. For example, reverse transcription of miRNAs may be performed using the TaqMan MicroRNA Reverse Transcription Kit (Applied Biosystems) according to manufacturer's recommendations. Briefly, miRNA may be combined with dNTPs, MultiScribe reverse transcriptase and the primer specific for the target miRNA. The resulting cDNA may be diluted and may be used for PCR reaction. The PCR may be performed according to the manufacturer's recommendation (Applied Biosystems). Briefly, cDNA may be combined with the TaqMan assay specific for the target miRNA and PCR reaction may be performed using ABI7300.

Nucleic acid hybridization may be performed using a microarray/biochip or in situ hybridization. In situ hybridization is preferred for the analysis of a single RNA molecule, e.g. a miRNA, or a low number of RNA molecules, miRNAs. The microarray/biochip, however, allows the analysis of a single RNA molecule, e.g. a miRNA, and a high number of RNA molecules, e.g. miRNAs.

It is more preferred that (i) the nucleic acid hybridization is performed using a microarray/biochip or beads, or using in situ hybridization, and/or (ii) the nucleic acid amplification is performed using real-time PCR.

It is preferred that the suitable technique in step (ii) is selected from the group consisting of nucleic acid hybridization, nucleic acid amplification, polymerase extension, sequencing, and mass spectroscopy, or any combination thereof. It is more preferred that (i) the nucleic acid hybridization is performed using a microarray/biochip, beads, or in situ hybridization, and/or (ii) the nucleic acid amplification is performed using real-time PCR.

In a fourth aspect, the present invention relates to a method for diagnosing a disease in an individual comprising the steps of.
(i) carrying out the method according to the second aspect, wherein the whole blood sample is (taken, obtained, isolated) from an individual,
(ii) determining the level of RNA molecules with <200 nucleotides in length by a suitable technique,
(iii) comparing said level to one or more reference level(s), and (iv) diagnosing or differentially diagnosing whether the individual is afflicted by the disease based on the comparison.

The determination in step (ii) may be carried out by any convenient means for determining the level of the RNA molecules, e.g. miRNAs, particularly the expression level of the RNA molecules, e.g. miRNAs. For example, qualitative, semi-quantitative, and/or quantitative detection methods may be used. A variety of techniques are well known to the person skilled in the art.

It is preferred that the level of the RNA molecules, e.g. miRNAs, particularly the expression level of the RNA molecules, e.g. miRNAs, is determined by nucleic acid hybridization, nucleic acid amplification, polymerase extension, sequencing, mass spectroscopy or any combination thereof.

Nucleic acid amplification may be performed using real time polymerase chain reaction (RT-PCR) such as real time quantitative polymerase chain reaction (RT qPCR). The real time polymerase chain reaction (RT-PCR) is preferred for the analysis of a single RNA molecule, e.g. a miRNA, or a low number of RNA molecules, e.g. miRNAs. It is particularly suitable for detecting low abundance RNA molecules, e.g. miRNAs. The real time quantitative polymerase chain reaction (RT qPCR), however, allows the analysis of a single RNA molecule, e.g. a miRNA, and a high number of RNA molecules, miRNAs.

A variety of kits and protocols to determine the expression level of miRNAs by real time polymerase chain reaction (RT-PCR) such as real time quantitative polymerase chain reaction (RT qPCR) are available. For example, reverse transcription of miRNAs may be performed using the TaqMan MicroRNA Reverse Transcription Kit (Applied Biosystems) according to manufacturer's recommendations. Briefly, miRNA may be combined with dNTPs, MultiScribe reverse transcriptase and the primer specific for the target miRNA. The resulting cDNA may be diluted and may be used for PCR reaction. The PCR may be performed according to the manufacturer's recommendation (Applied Biosystems). Briefly, cDNA may be combined with the TaqMan assay specific for the target miRNA and PCR reaction may be performed using ABI7300.

Nucleic acid hybridization may be performed using a microarray/biochip or in situ hybridization. In situ hybridization is preferred for the analysis of a single RNA molecule, e.g. a miRNA, or a low number of RNA molecules, miRNAs. The microarray/biochip, however, allows the analysis of a single RNA molecule, e.g. a miRNA, and a high number of RNA molecules, e.g. miRNAs.

It is more preferred that (i) the nucleic acid hybridization is performed using a microarray/biochip or beads, or using in situ hybridization, and/or (ii) the nucleic acid amplification is performed using real-time PCR.

It is preferred that the suitable technique in step (ii) is selected from the group consisting of nucleic acid hybridization, nucleic acid amplification, polymerase extension, sequencing, and mass spectroscopy, or any combination thereof. It is more preferred that (i) the nucleic acid hybridization is performed using a microarray/biochip, beads, or in situ hybridization, and/or (ii) the nucleic acid amplification is performed using real-time PCR.

Said fourth aspect may alternatively be formulated as follows: A method for diagnosing a disease in an individual comprising the steps of:
(i) carrying out the method according to the third aspect, wherein the whole blood sample is (taken, obtained, isolated) from an individual,
(ii) comparing said level to one or more reference level(s), and
(iii) diagnosing or differentially diagnosing whether the individual is afflicted by the disease based on the comparison.

The reference level may be any level which allows to determine whether an individual suffers from the disease or not. Preferably, the one or more reference level(s) (is) are determined by measuring one or more reference whole blood sample(s), e.g. 1, 2, 3, 4, 5, 6, 7, 8, 9, 10, 20, 30, 40, 50, 60, 70, 80, 90, 100, 150, 200, 250, 300, 400, or 500 reference whole blood sample(s), from one or more healthy subject(s), e.g. 1, 2, 3, 4, 5, 6, 7, 8, 9, 10, 20, 30, 40, 50, 60, 70, 80, 90, 100, 150, 200, 250, 300, 400, or 500 healthy subject(s),
one or more subject(s) suffering from a disease, e.g. 1, 2, 3, 4, 5, 6, 7, 8, 9, 10, 20, 30, 40, 50, 60, 70, 80, 90, 100, 150, 200, 250, 300, 400, or 500 subject(s) suffering from a disease, and/or
one or more subject(s) suffering from another disease e.g. 1, 2, 3, 4, 5, 6, 7, 8, 9, 10, 20, 30, 40, 50, 60, 70, 80, 90, 100, 150, 200, 250, 300, 400, or 500 subject(s) suffering from another disease.

In particular, the one or more reference level(s) is (are) determined by measuring one or more reference whole blood sample(s) from
one or more lung cancer subject(s), preferably lung cancer subjects subjected to lung cancer therapy, more preferably lung cancer subjects subjected to palliative or adjuvant lung cancer therapy, and/or one or more subject(s) being healthy, preferably subjects not being subjected to lung cancer therapy, more preferably subjects not being subjected to palliative or adjuvant lung cancer therapy.

It is practicable to take one reference whole blood sample per subject for analysis. If additional reference whole blood sample(s) are required, the same subject may be (re)tested. Said reference level may be an average reference level. It may be determined by measuring reference levels and calculating the "average" value (e.g. mean, median or modal value) thereof. It is preferred that the reference level is from a subject of the same gender (e.g. female or male) and/or of a similar age/phase of life (e.g. adults or elderly) than the patient to be tested or diagnosed.

The disease may be any disease, e.g. lung cancer. The other disease may be any other disease than lung cancer.

In one embodiment, the method for diagnosing a disease in an individual comprises the steps of:
(i) carrying out the method according to the third aspect, wherein the whole blood sample is (taken, obtained, isolated) from an individual,
(ii) comparing said level to a reference level which is determined by measuring one or more reference whole blood sample(s) from one or more healthy subject(s), and
(iii) diagnosing whether the individual is afflicted by the disease based on the comparison.

Preferably, the disease is lung cancer.

In one another embodiment, the method for diagnosing a disease in an individual comprises the steps of:
(i) carrying out the method according to the third aspect, wherein the whole blood sample is (taken, obtained, isolated) from an individual,
(ii) comparing said level to a reference level which is determined by measuring one or more reference whole blood sample(s) from one or more subject(s) suffering from the disease, and (iii) diagnosing whether the individual is afflicted by the disease based on the comparison. Preferably, the disease is lung cancer.

In one another embodiment, the method for diagnosing a disease in an individual comprises the steps of:
(i) carrying out the method according to the third aspect, wherein the whole blood sample is (taken, obtained, isolated) from an individual,
(ii) comparing said level to a reference level which is determined by measuring one or more reference whole blood sample(s) from one or more subject(s) suffering from the disease and to a reference level which is determined by measuring one or more reference whole blood sample(s) from one or more subject(s) suffering from another disease, and
(iii) diagnosing whether the individual is afflicted by the disease based on the comparison.

Preferably, the disease is lung cancer and the other disease is any other disease than lung cancer.

The method may also allow to distinguish differently treated diseases from each other. For example, the disease may be an adjuvant-treated disease, e.g. adjuvant-treated lung cancer, and the other disease may be a palliative-treated disease, e.g. palliative-treated lung cancer, or the disease may be a palliative-treated disease, e.g. palliative-treated lung cancer, and the other disease may be an adjuvant-treated disease, e.g. adjuvant-treated lung cancer.

In a fifth aspect, the present invention relates to the use of a hydrophilic polymeric material for removing an RNA fraction with ≥200 nucleotides in length from a whole blood sample. Preferably, the RNA fraction with ≥200 nucleotides in length comprises one or more RNA molecules selected from the group consisting of ribosomal 18S RNA and ribosomal 28S RNA.

In a sixth aspect, the present invention relates to the use of a hydrophilic polymeric material for purifying an RNA fraction with <200 nucleotides in length from a whole blood sample. Preferably, the RNA fraction with <200 nucleotides in length comprises one or more RNA molecules selected from the group consisting of miRNA, tRNA, siRNA, piRNA, and snoRNA.

In one embodiment of the fifth and sixth aspect of the present invention, the hydrophilic polymeric material is comprised in an adsorbent probe (see first and second aspect of the present invention).

In one embodiment of the fifth and sixth aspect of the present invention, the hydrophilic polymeric material has a density of ≤6 g/cm$^3$, preferably of ≤4 g/cm$^3$, e.g. of 0.5, 1.5, 2, 2.5, 3, 3.5, 4, 4.5, 5, 5.5, or 6 g/cm$^3$. More preferably, the hydrophilic polymeric material has a density of between 0.5 and 6 g/cm$^3$, even more preferably of between 1 and 4 g/cm$^3$, e.g. of 0.5, 1.5, 2, 2.5, 3, 3.5, 4, 4.5, 5, 5.5, or 6 g/cm$^3$.

In one embodiment of the fifth and sixth aspect of the present invention, the hydrophilic polymeric material is porous.

In one embodiment of the fifth and sixth aspect of the present invention, the hydrophilic polymeric material has a pore volume of between 20 and 70%, preferably of between 30 and 50%, e.g. of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70% of the total volume of the material.

In one embodiment of the fifth and sixth aspect of the present invention, the hydrophilic polymeric material comprises pores that are ≤100 μm, preferably ≤50 μm, e.g. ≤10, 15, 20, 25, 30, 35, 40, 45, 50, 55, 60, 65, 70, 75, 80, 85, 90, 95, or 100 μm, in diameter or largest cross-sectional dimension. More preferably, the hydrophilic polymeric material comprises pores that are between 10 to 100 μm, even more preferably between 20 and 50 μm, e.g. 10, 15, 20, 25, 30, 35, 40, 45, 50, 55, 60, 65, 70, 75, 80, 85, 90, 95, or 100 μm, in diameter or largest cross-sectional dimension.

In one embodiment of the fifth and sixth aspect of the present invention, the hydrophilic polymeric material is selected from the group consisting of a cellulose comprising material, e.g. cotton, a polysaccharide, a polyolefin, and a polyester. Preferably,
(i) the polysaccharide is cellulose,
(ii) the polyolefin is selected from the group consisting of polyethylene, polypropylene, polybutylene, polyisobutylene, and polymethylpentene, or
(iii) the polyester is selected from the group consisting of polycarbonate and polyethylenterephthalate.

More preferably, the hydrophilic polymeric material is cotton, cellulose or polyethylene.

In one embodiment of the fifth and sixth aspect of the present invention, the hydrophilic polymeric material is a material as described in WO 2013/067520 A1 or US 2013116597 A1. In particular, the hydrophilic polymeric material is part of an absorbent probe which is comprised in a biological fluid sampling device as described in WO 2013/067520 A1 or US 2013116597 A1. In this respect, it is referred to page 10, line 28 to page 34, line 27, FIGS. 2, 3 and 8, and claims 1 to 19 of WO 2013/067520 A1 and to paragraphs [0068] to [0129], FIGS. 2, 3 and 8, and claims 1 to 19 of US 2013116597 A1.

With respect to other embodiments of the absorbent probe and/or hydrophilic polymeric material, it is referred to the first or second aspect of the present invention.

In a seventh aspect, the present invention relates to the use of a method according to the third aspect for diagnosing or differentially diagnosing a disease. The disease may be lung cancer. As to the diagnosis or differential diagnosis of a disease, it is referred to the fourth aspect of the present invention.

In an eight aspect, the present invention relates to a kit comprising
(i) an absorbent probe comprising, essentially consisting of, or consisting of a hydrophilic polymeric material.

The kit is useful for taking a whole blood sample.

In one embodiment of the eight aspect of the present invention, the kit further comprises
(ii) means to remove blood from an individual,
(iii) a container, and/or
(iv) a data carrier comprising the information that the absorbent probe with the whole blood from the whole blood sample absorbed into it is usable in the methods of the first to fourth aspect of the present invention.

In one alternative embodiment of the eight aspect of the present invention, the kit further comprises
(ii) means to remove blood from an individual,
(iii) means for determining the level of RNA molecules with ≥200 nucleotides in length and/or of RNA molecules with <200 nucleotides in length,
(iv) a container, and/or
(v) a data carrier comprising the information that the absorbent probe with the whole blood from the whole blood sample absorbed into it is usable in the methods of the first to fourth aspect of the present invention.

The means to remove blood from an individual may be selected from the group consisting of a syringe (with a needle), a needle, and a lancet. The syringe (with a needle) may be used to extract blood from a vein in the arm of an individual. The needle or lancet may be used to destroy the upper skin layer and remove a blood drop (e.g. via a finger prick) from an individual. The absorbent probe comprising, essentially consisting of, or consisting of a hydrophilic polymeric material is then placed in (physical) contact with the whole blood sample, thereby absorbing whole blood into the hydrophilic polymeric material. Afterwards, the absorbent probe may be dried, e.g. air dried. This can be done at room temperature (20° C.) or at elevated temperatures (e.g. 30° C.).

The absorbent probe comprising a hydrophilic polymeric material into which whole blood from the whole blood sample has been absorbed may then be sent in a laboratory for further analysis.

The means for determining the level of RNA molecules with ≥200 nucleotides in length and/or of RNA molecules with <200 nucleotides in length may comprise:
(i) polynucleotides for detecting RNA molecules with ≥200 nucleotides in length and/or of RNA molecules with <200 nucleotides in length, and/or
(ii) a biochip, a RT-PCT system, a PCR-system, a flow cytometer or a next generation sequencing system.

Preferably, the RNA molecules with <200 nucleotides in length are miRNA molecules.

Said polynucleotides may be attached to a biochip. Said polynucleotides may also be used as primers in a RT-PCT system, a PCR-system, or a next generation sequencing system.

The data carrier may be a non-electronical data carrier, e.g. a graphical data carrier such as an information leaflet (e.g. including details on how to employ said kit according to the first to fourth aspect of the present invention), an information sheet, a bar code or an access code, or an electronical data carrier such as a floppy disk, a compact disk (CD), a digital versatile disk (DVD), a microchip or another semiconductor-based electronical data carrier. The access code may allow the access to a database, e.g. an internet database, a centralized, or a decentralized database. The access code may also allow access to an application software that causes a computer to perform tasks for computer users or a mobile app which is a software designed to run on smartphones and other mobile devices.

Said data carrier may further comprise one or more reference level(s) of the level of the RNA molecules, e.g. miRNAs, determined herein. In case that the data carrier comprises an access code which allows the access to a database, said one or more reference level(s) may be deposited in this database.

The kit may optionally comprise materials desirable from a commercial and user standpoint including a buffer(s), a reagent(s) and/or a diluent(s) which may be useful in taking a whole blood sample.

In a ninth aspect, the present invention relates to a kit comprising
(i) a fluid to reconstitute whole blood absorbed into an absorbent probe (from a whole blood sample) comprising, essentially consisting of or consisting of a hydrophilic polymeric material.

The fluid may be a liquid or gas. Preferably, the fluid is a chaotropic fluid, e.g. a chaotropic liquid or gas. More preferably, the chaotropic fluid is selected from the group consisting of guanidinium thiocyanate, guanidinium isothiocyanate, guanidinium hydrochloride, guanidinium chloride, alkali thiocyanate, alkali isothiocyanate, alkali iodide, and alkali perchlorate. Even more preferably, the chaotropic fluid is guanidinium thiocyanate. Alternatively, the chaotropic fluid, e.g. chaotropic liquid or gas, may comprise guanidinium thiocyanate, guanidinium isothiocyanate, guanidinium hydrochloride, guanidinium chloride, alkali thiocyanate, alkali isothiocyanate, alkali iodide, and alkali perchlorate. Preferably, the chaotropic fluid comprises guanidinium thiocyanate.

The kit is useful for carrying out the methods of the first to fourth aspect of the present invention, i.e. for removing an RNA fraction with ≥200 nucleotides in length from a whole blood sample, for purifying an RNA fraction with <200 nucleotides in length from a whole blood sample, and for purifying an RNA fraction with <200 nucleotides in length from a whole blood sample and (subsequently) determining the level of said RNA molecules.

The RNA fractions mentioned above comprise one or more RNA molecules, e.g. miRNA molecules. The RNA fraction with ≥200 nucleotides in length preferably comprises one or more RNA molecules selected from the group consisting of ribosomal 18S RNA and ribosomal 28S RNA and the RNA fraction with <200 nucleotides in length preferably comprises one or more RNA molecules selected from the group consisting of miRNA, tRNA, siRNA, piRNA, and snorRNA.

If the kit is for purifying an RNA fraction with <200 nucleotides in length from a whole blood sample and (subsequently) determining the level of said RNA molecules, it further comprises means for determining the level, particularly the expression level, of the RNA molecules (e.g. miRNA molecules). Preferably, said means comprise one or more polynucleotides for determining the (expression) level of one or more RNA molecules (e.g. miRNA molecules), and/or a microarray, a RT-PCT system, a PCR-system, a flow cytometer, a bead-based multiplex system or a next generation sequencing system.

In one embodiment of the ninth aspect of the present invention, the kit further comprises
(ii) a container, and/or
(iii) a data carrier with instructions on how to carry out the methods of the first to fourth aspect of the present invention.

In an alternative embodiment of the ninth aspect of the invention, the kit further comprises:
(ii) means for determining the level of RNA molecules with ≥200 nucleotides in length and/or of RNA molecules with <200 nucleotides in length,
(iii) a container, and/or
(iv) a data carrier with instructions on how to carry out the methods of the first to fourth aspect of the present invention.

The means for determining the level of RNA molecules with ≥200 nucleotides in length and/or of RNA molecules with <200 nucleotides in length may comprise:
(i) polynucleotides for detecting RNA molecules with ≥200 nucleotides in length and/or of RNA molecules with <200 nucleotides in length, and/or
(ii) a biochip, a RT-PCT system, a PCR-system, a flow cytometer or a next generation sequencing system.

Preferably, the RNA molecules with <200 nucleotides in length are miRNA molecules.

Said polynucleotides may be attached to a biochip. Said polynucleotides may also be used as primers in a RT-PCT system, a PCR-system, or a next generation sequencing system.

The kit may comprise one or more container. For example, the fluid may be comprised in a container, e.g. in a bottle, in particular spray bottle. In addition, the means for determining the level of said RNA molecules may be comprised in a container.

The data carrier may be a non-electronical data carrier, e.g. a graphical data carrier such as an information leaflet, an information sheet, a bar code or an access code, or an electronical data carrier such as a floppy disk, a compact disk (CD), a digital versatile disk (DVD), a microchip or another semiconductor-based electronical data carrier. The access code may allow the access to a database, e.g. an internet database, a centralized, or a decentralized database. The access code may also allow access to an application software that causes a computer to perform tasks for computer users or a mobile app which is a software designed to run on smartphones and other mobile devices.

Said data carrier may further comprise one or more reference level(s) of the level of the RNA molecules, e.g. miRNAs, determined herein. In case that the data carrier comprises an access code which allows the access to a database, said one or more reference level(s) may be deposited in this database.

The kit may optionally comprise materials desirable from a commercial and user standpoint including a buffer(s), a reagent(s) and/or a diluent(s) to carry out the methods of the first to fourth aspect of the present invention.

In one embodiment of the eighth or ninth aspect of the present invention, the hydrophilic polymeric material has a density of ≤6 g/cm$^3$, preferably of ≤4 g/cm$^3$, e.g. of 0.5, 1.5, 2, 2.5, 3, 3.5, 4, 4.5, 5, 5.5, or 6 g/cm$^3$. More preferably, the hydrophilic polymeric material has a density of between 0.5 and 6 g/cm$^3$, even more preferably of between 1 and 4 g/cm$^3$, e.g. of 0.5, 1.5, 2, 2.5, 3, 3.5, 4, 4.5, 5, 5.5, or 6 g/cm$^3$.

In one embodiment of the eighth or ninth aspect of the present invention, the hydrophilic polymeric material is porous.

In one embodiment of the eighth or ninth aspect of the present invention, the hydrophilic polymeric material has a pore volume of between 20 and 70%, preferably of between 30 and 50%, e.g. of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70% of the total volume of the material.

In one embodiment of the eighth or ninth aspect of the present invention, the hydrophilic polymeric material comprises pores that are ≤100 μm, preferably ≤50 μm, e.g. ≤10, 15, 20, 25, 30, 35, 40, 45, 50, 55, 60, 65, 70, 75, 80, 85, 90, 95, or 100 μm, in diameter or largest cross-sectional dimension. More preferably, the hydrophilic polymeric material comprises pores that are between 10 to 100 μm, even more preferably between 20 and 50 μm, e.g. 10, 15, 20, 25, 30, 35, 40, 45, 50, 55, 60, 65, 70, 75, 80, 85, 90, 95, or 100 μm, in diameter or largest cross-sectional dimension.

In one embodiment of the eight or ninth aspect of the present invention, the hydrophilic polymeric material is selected from the group consisting of a cellulose comprising material, e.g. cotton, a polysaccharide, a polyolefin, and a polyester. Preferably,
(i) the polysaccharide is cellulose,
(ii) the polyolefin is selected from the group consisting of polyethylene, polypropylene, polybutylene, polyisobutylene, and polymethylpentene, or
(iii) the polyester is selected from the group consisting of polycarbonate and polyethylenterephthalate.
More preferably, the hydrophilic polymeric material is cotton, cellulose or polyethylene.

In one embodiment of the eighth or ninth aspect of the present invention, the absorbent probe has absorbed a predetermined maximum volume of whole blood of between 1 to 50 μl, e.g. of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 μl.

In one embodiment of the eighth or ninth aspect of the present invention, the absorbent probe has a length of ≤10 mm, preferably of ≤5 mm, e.g. of ≤2, 2.5, 3, 3.5, 4, 4.5, 5, 5.5, 6, 6.5, 7, 7.5, 8, 8.5, 9, 9.5, or 10 mm, and a cross-sectional area of ≤40 mm$^2$, preferably of ≤20 mm$^2$, e.g. of ≤5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 mm$^2$.

Such sizes are believed suitable when the whole blood sample is a blood drop, e.g. from a finger prick.

In an alternative embodiment of the eighth or ninth aspect of the present invention the absorbent probe has a volume of ≤250 mm$^3$, preferably of ≤200 mm$^3$, e.g. of ≤1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, 200, 210, 220, 230, 240, or 250 mm$^3$.

Such volumes are believed suitable when the whole blood sample is a blood drop, e.g. from a finger prick.

More preferably, the absorbent probe has a length of between 2 and 10 mm, preferably of between 2 and 5 mm, e.g. of 2, 2.5, 3, 3.5, 4, 4.5, 5, 5.5, 6, 6.5, 7, 7.5, 8, 8.5, 9, 9.5, or 10 mm, and a cross-sectional area of between 5 and 40 mm$^2$, preferably of between 5 and 20 mm$^2$, e.g. of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 mm$^2$.

In an alternative embodiment of the eighth or ninth aspect of the present invention the absorbent probe has a volume of between 1 mm$^3$ to 250 mm$^3$, preferably of between 2.5 mm$^3$ to 200 mm$^3$, e.g. of 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, 200, 210, 220, 230, 240, or 250 mm$^3$.

In one embodiment of the eighth or ninth aspect of the present invention, the absorbent probe is configured to absorb a predetermined maximum volume of whole blood of between 1 to 50 μl, preferably of between 5 to 25 μl, and even more preferably of between 10 to 20 μl, e.g. of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 μl.

With respect to other embodiments of the absorbent probe and/or hydrophilic polymeric material, it is referred to the first or second aspect of the present invention.

The present invention is summarized as follows:
1. A method of removing an RNA fraction with ≥200 nucleotides in length from a whole blood sample comprising the steps of:
   (i) providing an absorbent probe comprising a hydrophilic polymeric material into which whole blood from the whole blood sample has been absorbed,
   (ii) contacting the absorbent probe with a fluid (to reconstitute the whole blood), and
   (iii) recovering the fluid from step (ii), thereby removing the RNA fraction with ≥200 nucleotides in length.
2. The method of item 1, wherein the RNA fraction with ≥200 nucleotides in length comprises one or more RNA molecules selected from the group consisting of ribosomal 18S RNA and ribosomal 28S RNA.

3. A method of purifying an RNA fraction with <200 nucleotides in length from a whole blood sample comprising the steps of:
   (i) providing an absorbent probe comprising a hydrophilic polymeric material into which whole blood from the whole blood sample has been absorbed,
   (ii) contacting the absorbent probe with a fluid (to reconstitute the whole blood), and
   (iii) recovering the fluid from step (ii), thereby purifying the RNA fraction with <200 nucleotides in length.
4. The method of item 3, wherein the RNA fraction with <200 nucleotides in length comprises one or more RNA molecules selected from the group consisting of miRNA, tRNA, siRNA, piRNA, and snorRNA.
5. The method of any one of items 1 to 4, wherein the hydrophilic polymeric material has a density of ≤6 g/cm$^3$, preferably of ≤4 g/cm$^3$.
6. The method of item 5, wherein the hydrophilic polymeric material has a density of between 0.5 and 6 g/cm$^3$, preferably of between 1 and 4 g/cm$^3$.
7. The method of any one of items 1 to 6, wherein the hydrophilic polymeric material is porous.
8. The method of any one of item 1 to 7, wherein the hydrophilic polymeric material has a pore volume of between 20 and 70%, preferably of between 30 and 50%, of the total volume of the material.
9. The method of items 7 or 8, wherein the hydrophilic polymeric material comprises pores that are ≤100 μm, preferably ≤50 μm, in diameter or largest cross-sectional dimension.
10. The method of item 9, wherein the hydrophilic polymeric material comprises pores that are between 10 to 100 μm, preferably between 20 and 50 μm, in diameter or largest cross-sectional dimension.
11. The method of any one of items 1 to 10, wherein the hydrophilic polymeric material is selected from the group consisting of cotton, a polysaccharide, a polyolefin, and a polyester.
12. The method of item 11, wherein
   (i) the polysaccharide is cellulose,
   (ii) the polyolefin is selected from the group consisting of polyethylene, polypropylene, polybutylene, polyisobutylene, and polymethylpentene, or
   (iii) the polyester is selected from the group consisting of polycarbonate and polyethylenterephthalate.
13. The method of any one of items 1 to 12, wherein the absorbent probe has absorbed a predetermined maximum volume of whole blood of between 1 to 50 μl.
14. The method of any one of items 1 to 13, wherein
   the absorbent probe has a length of ≤10 mm, preferably of ≤5 mm, and a cross-sectional area of ≤40 mm$^2$, preferably of ≤20 mm$^2$, or
   the absorbent probe has a volume of ≤250 mm$^3$, preferably of ≤200 mm$^3$.
15. The method of item 14, wherein
   the absorbent probe has a length of between 2 and 10 mm, preferably of between 2 and 5 mm, and a cross-sectional area of between 5 and 40 mm$^2$, preferably of between 5 and 20 mm$^2$, or
   the absorbent probe has a volume of between 1 mm$^3$ to 250 mm$^3$, preferably of between 2.5 mm$^3$ to 200 mm$^3$.
16. The method of any one of items 1 to 15, wherein the whole blood absorbed into the hydrophilic polymeric material has been dried.
17. The method of any one of items 3 to 16, wherein the method further comprises the step of:
   (iv) isolating the RNA fraction with <200 nucleotides in length by one or more separation techniques.
18. The method of item 17, wherein the one or more separation techniques are selected from the group consisting of centrifugation, evaporation/reconstitution, concentration, precipitation, liquid/liquid extraction, and solid phase extraction.
19. A method of determining the level of RNA molecules with <200 nucleotides in length comprising the steps of:
   (i) carrying out the method of any one of items 3 to 18, and
   (ii) determining the level of RNA molecules with <200 nucleotides in length by a suitable technique.
20. The method of item 19, wherein the RNA molecules with <200 nucleotides in length are selected from the group consisting of miRNA, tRNA, siRNA, piRNA, and snorRNA.
21. The method of items 19 or 20, wherein the level which is determined in step (ii) is the expression level.
22. The method of any one of items 19 to 21, wherein the suitable technique is selected from the group consisting of nucleic acid hybridization, nucleic acid amplification, polymerase extension, sequencing, and mass spectroscopy, or any combination thereof.
23. The method of item 22, wherein
   (i) the nucleic acid hybridization is performed using a microarray/biochip, beads, or in situ hybridization, and/or
   (ii) the nucleic acid amplification is performed using real-time PCR.
24. A method for diagnosing a disease in an individual comprising the steps of:
   (i) carrying out the method of any one of items 3 to 18, wherein the whole blood sample is from an individual,
   (ii) determining the level of RNA molecules with <200 nucleotides in length by a suitable technique,
   (iii) comparing said level to one or more reference level(s), and
   (iv) diagnosing or differentially diagnosing whether the individual is afflicted by the disease based on the comparison.
25. The method of item 24, wherein the suitable technique is selected from the group consisting of nucleic acid hybridization, nucleic acid amplification, polymerase extension, sequencing, and mass spectroscopy, or any combination thereof.
26. A method for diagnosing a disease in an individual comprising the steps of:
   (i) carrying out the method of any one of items 19 to 23, wherein the whole blood sample is from an individual,
   (ii) comparing said level to one or more reference level(s), and
   (iii) diagnosing or differentially diagnosing whether the individual is afflicted by the disease based on the comparison.
27. The method of any one of items 24 to 26, wherein the one or more reference level(s) are determined by measuring one or more reference whole blood sample(s) from one or more healthy subject(s),
   one or more subject(s) suffering from a disease, and/or one or more subject(s) suffering from another disease.
28. Use of a hydrophilic polymeric material for removing an RNA fraction with ≥200 nucleotides in length from a whole blood sample.

29. The use of item 28, wherein the RNA fraction with ≥200 nucleotides in length comprises one or more RNA molecules selected from the group consisting of ribosomal 18S RNA and ribosomal 28S RNA.
30. Use of a hydrophilic polymeric material for purifying an RNA fraction with <200 nucleotides in length from a whole blood sample.
31. The use of item 30, wherein the RNA fraction with <200 nucleotides in length comprises one or more RNA molecules selected from the group consisting of miRNA, tRNA, siRNA, piRNA, and snorRNA.
32. The use of any one of items 28 to 31, wherein the hydrophilic polymeric material has a density of ≤6 g/cm$^3$, preferably of ≤4 g/cm$^3$.
33. The use of item 32, wherein the hydrophilic polymeric material has a density of between 0.5 and 6 g/cm$^3$, preferably of between 1 and 4 g/cm$^3$.
34. The use of any one of items 28 to 33, wherein the hydrophilic polymeric material is porous.
35. The use of any one of items 28 to 34, wherein the hydrophilic polymeric material has a pore volume of between 20 and 70%, preferably of between 30 and 50%, of the total volume of the material.
36. The use of items 34 or 35, wherein the hydrophilic polymeric material comprises pores that are ≤100 μm, preferably ≤50 μm, in diameter or largest cross-sectional dimension.
37. The use of item 36, wherein the hydrophilic polymeric material comprises pores that are between 10 to 100 μm, preferably between 20 and 50 μm, in diameter or largest cross-sectional dimension.
38. The use of any one of items 28 to 37, wherein the hydrophilic polymeric material is selected from the group consisting of cotton, a polysaccharide, a polyolefin, and a polyester.
39. The use of item 38, wherein
   (i) the polysaccharide is cellulose,
   (ii) the polyolefin is selected from the group consisting of polyethylene, polypropylene, polybutylene, polyisobutylene, and polymethylpentene, or
   (iii) the polyester is selected from the group consisting of polycarbonate and polyethylenterephthalate.
40. Use of a method according to any one of items 19 to 23 for diagnosing or differentially diagnosing a disease.
41. A kit comprising
   (i) an absorbent probe comprising a hydrophilic polymeric material.
42. The kit of item 41, wherein the kit is useful for taking a whole blood sample.
43. The kit of items 41 or 42, wherein the kit further comprises
   (ii) means to remove blood from an individual,
   (iii) means for determining the level of RNA molecules with ≥200 nucleotides in length and/or of RNA molecules with <200 nucleotides in length,
   (iv) a container, and/or
   (v) a data carrier comprising the information that the absorbent probe with the whole blood from the whole blood sample absorbed into it is usable in the methods of any one of items 1 to 27.
44. A kit comprising
   (i) a fluid to reconstitute whole blood absorbed into an absorbent probe comprising a hydrophilic polymeric material.
45. The kit of item 44, wherein the kit is useful for carrying out the methods of any one of items 1 to 27.
46. The kit of items 44 or 45, wherein the kit further comprises
   (ii) means for determining the level of RNA molecules with ≥200 nucleotides in length and/or of RNA molecules with <200 nucleotides in length,
   (iii) a container, and/or
   (iv) a data carrier with instructions on how to carry out the methods of any one of items 1 to 23.
47. The kit of any one of items 41 to 46, wherein the hydrophilic polymeric material has a density of ≤6 g/cm$^3$, preferably of ≤4 g/cm$^3$.
48. The kit of item 47, wherein the hydrophilic polymeric material has a density of between 0.5 and 6 g/cm$^3$, preferably of between 1 and 4 g/cm$^3$.
49. The kit of any one of items 41 to 48, wherein the hydrophilic polymeric material is porous.
50. The kit of any one of items 41 to 49, wherein the hydrophilic polymeric material has a pore volume of between 20 and 70%, preferably of between 30 and 50%, of the total volume of the material.
51. The kit of items 49 or 50, wherein the hydrophilic polymeric material comprises pores that are ≤100 μm, preferably ≤50 μm, in diameter or largest cross-sectional dimension.
52. The kit of item 51, wherein the hydrophilic polymeric material comprises pores that are between 10 to 100 μm, preferably between 20 and 50 μm, in diameter or largest cross-sectional dimension.
53. The kit of any one of items 41 to 52, wherein the hydrophilic polymeric material is selected from the group consisting of cotton, a polysaccharide, a polyolefin, and a polyester.
54. The kit of item 53, wherein
   (i) the polysaccharide is cellulose,
   (ii) the polyolefin is selected from the group consisting of polyethylene, polypropylene, polybutylene, polyisobutylene, and polymethylpentene, or
   (iii) the polyester is selected from the group consisting of polycarbonate and polyethylenterephthalate.
55. The kit of any one of items 41 to 54, wherein the absorbent probe is configured to absorb a predetermined maximum volume of whole blood of between 1 to 50 μl.
56. The kit of any one of items 41 to 55, wherein
   the absorbent probe has a length of ≤10 mm, preferably of ≤5 mm, and a cross-sectional area of ≤40 mm$^2$, preferably of ≤20 mm$^2$, or
   the absorbent probe has a volume of ≤250 mm$^3$, preferably of ≤200 mm$^3$.
57. The kit of item 56, wherein
   the absorbent probe has a length of between 2 and 10 mm, preferably of between 2 and 5 mm, and a cross-sectional area of between 5 and 40 mm$^2$, preferably of between 5 and 20 mm$^2$, or
   the absorbent probe has a volume of between 1 mm$^3$ to 250 mm$^3$, preferably of between 2.5 mm$^3$ to 200 mm$^3$.

Various modifications and variations of the invention will be apparent to those skilled in the art without departing from the scope of invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art in the relevant fields are intended to be covered by the present invention.

BRIEF DESCRIPTION OF THE FIGURES

The following Figures are merely illustrative of the present invention and should not be construed to limit the scope of the invention as indicated by the appended claims in any way.

(FIG. 4A) hydrophilic cellulose comprising polymeric absorbent probe material; such as Non-Indicating FTA Classic Card (GE Healthcare Life Science, Buckinghamshire, Great Britain), Non-Indicating FTA Elute Micro Card (GE Healthcare Life Science, Buckinghamshire, Great Britain), HemaSpot HF (Spot On Sciences, Austin, Tex., USA), HemaSpot SE (Spot On Sciences, Austin, Tex., USA), TFN (Munktell, Bärenstein, Germany), TFN-Di (Munktell, Bärenstein, Germany); (FIG. 4B) hydrophilic organic polymeric absorbent probe material; such as Mitra microsampling device.

FIG. 5: miRNA expression data: depicted are the miRNAs that were found to be expressed (on an Agilent dna-microarray, for details see Example 8) in the small RNA fraction that was obtained after removal of the >200 nt fraction from a whole blood sample that has been processed by use of an hydrophilic polymeric absorbent probe. Herein, as examples polymeric absorbent probes such as the Mitra microsampling device or a hydrophilic cellulose comprising absorbent probe (such as Non-Indicating FTA Classic Card (GE Healthcare Life Science, Buckinghamshire, Great Britain), Non-Indicating FTA Elute Micro Card (GE Healthcare Life Science, Buckinghamshire, Great Britain), HemaSpot HF (Spot On Sciences, Austin, Tex., USA), HemaSpot SE (Spot On Sciences, Austin, Tex., USA), TFN (Munktell, Bärenstein, Germany), TFN-Di (Munktell, Bärenstein, Germany)) were used as the device comprising said hydrophilic polymeric absorbent probe to remove the >200 nt RNA fraction form the whole blood sample. With: SEQ ID NO=sequence identification number; miRNA=microRNA identifier according to miRBase; gTotalGeneSignal (A)=relative expression level of the corresponding miRNAs detected when employing a hydrophilic cellulose comprising absorbent material for >200 nt RNA removal; gTotalGeneSignal (B)=relative expression level of the corresponding miRNAs detected when employing a hydrophilic polymeric absorbent material (Mitra microsampling device) for >200 nt RNA removal.

FIG. 8A. Scatterplots and correlations of different conditions for each environmental factor. FIG. 8B. PVCA plot of influencing environmental factors.

FIG. 10: Biological variation depending on lung cancer therapy. Expression intensities, fold changes, p-values and the area under the receiver operator characteristics curve (AUC value) of deregulated miRNAs.

EXAMPLES

The examples given below are for illustrative purposes only and do not limit the invention described above in any way.

Part I:

Example 1: Blood Sample Collection Using Hydrophilic Polymeric Absorbent Device (Mitra Microsampling Device)

Figure 1:
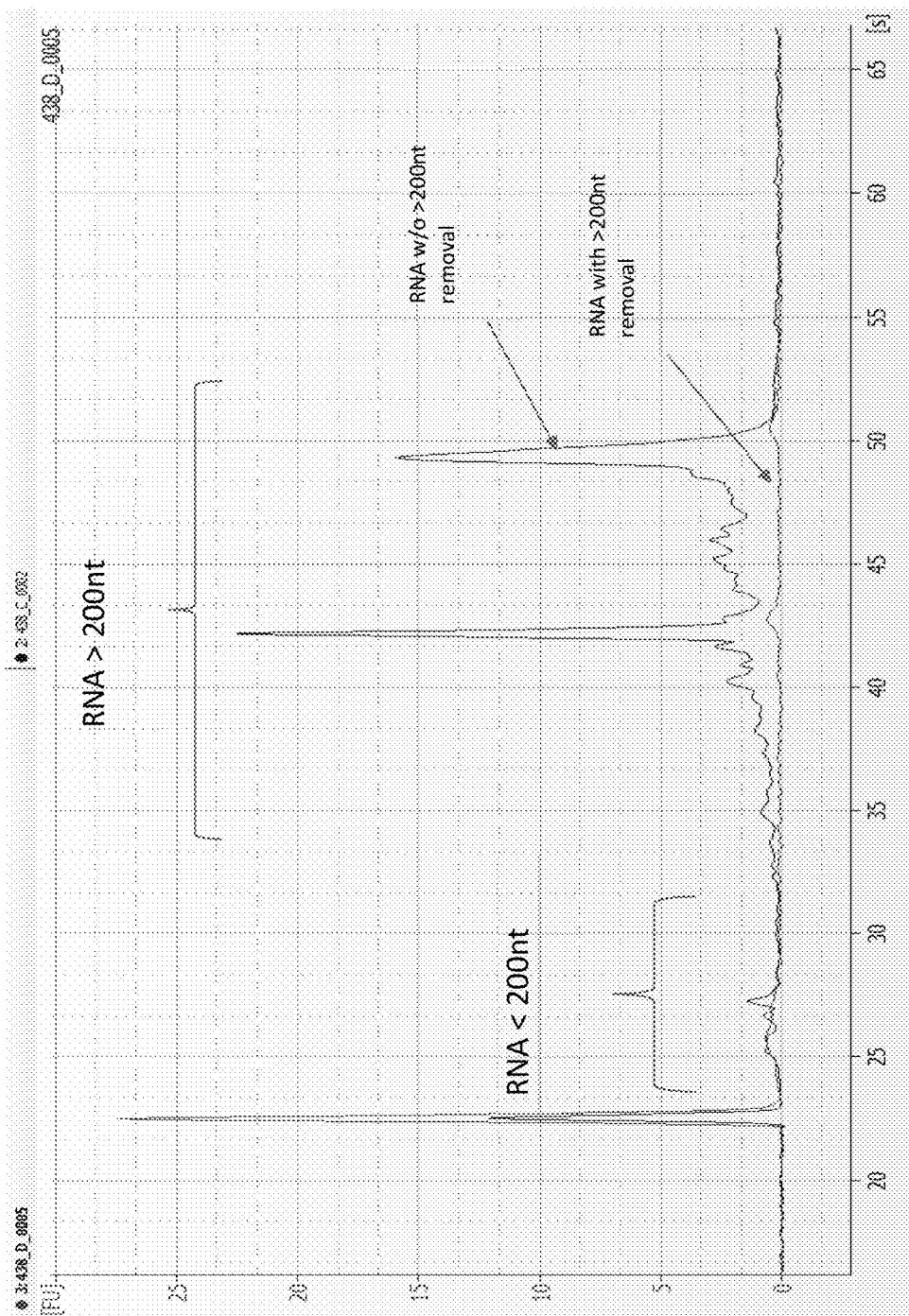
FIG. 1: Depicted is the comparison of the Agilent Bioanalyzer Nano results of RNA isolated from whole blood samples i) with removal of the RNA-fraction with >200 nt in length making use of an absorbent probe (Mitra Microsampling Device, lower curve) and ii) without removal of the RNA-fraction with >200 nt in length (whole blood collected in PAXgene Blood RNA Tube, upper curve) from a human individual. The upper curve clearly shows that the mayor RNA peaks (18S, 28S ribosomal RNA) is still present, while in the lower curve said 18S and 28S RNAs and other RNA species with >200 nt in length have been effectively removed by absorbing the whole blood sample to an absorbent probe of hydrophilic polymeric material.
Figure 2:
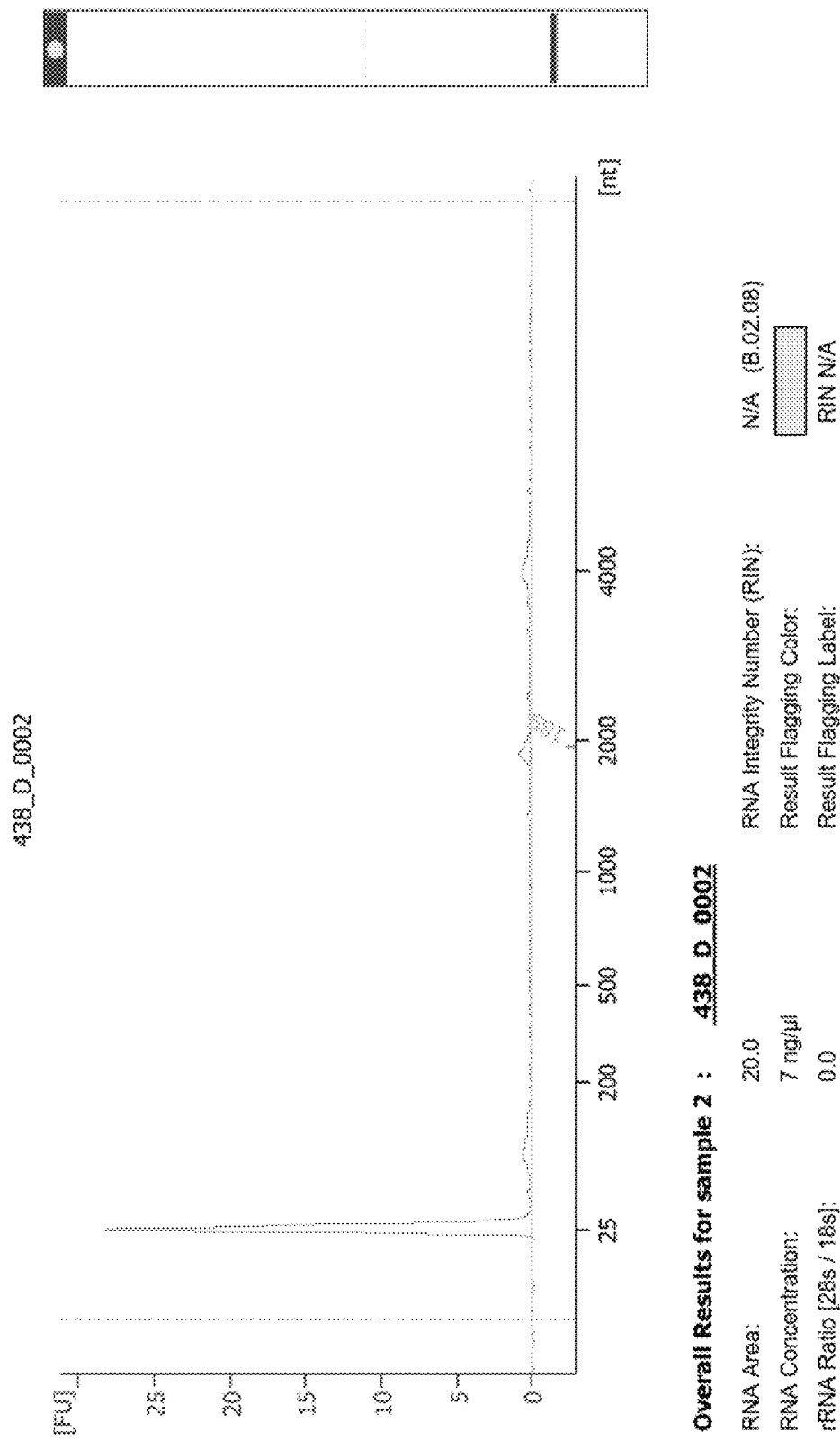
FIG. 2: Shown are the Agilent Bioanalyzer (Nano RNA kit) results of RNA isolated from whole blood samples collected from a human individual with removal of the RNA-fraction with >200 nt in length making use of an absorbent probe of hydrophilic polymeric material (Mitra Microsampling Device): the >200 nt RNA-fractions, including—but not limited to—the most prominent ribosomal RNA peaks (18S fragment at ~2,000 nt and 28S fragment at ~4,000 nt) are removed from the RNA obtained from a whole blood sample by use of an absorbent probe of hydrophilic polymeric material (Mitra Microsampling Device).
Figure 3:
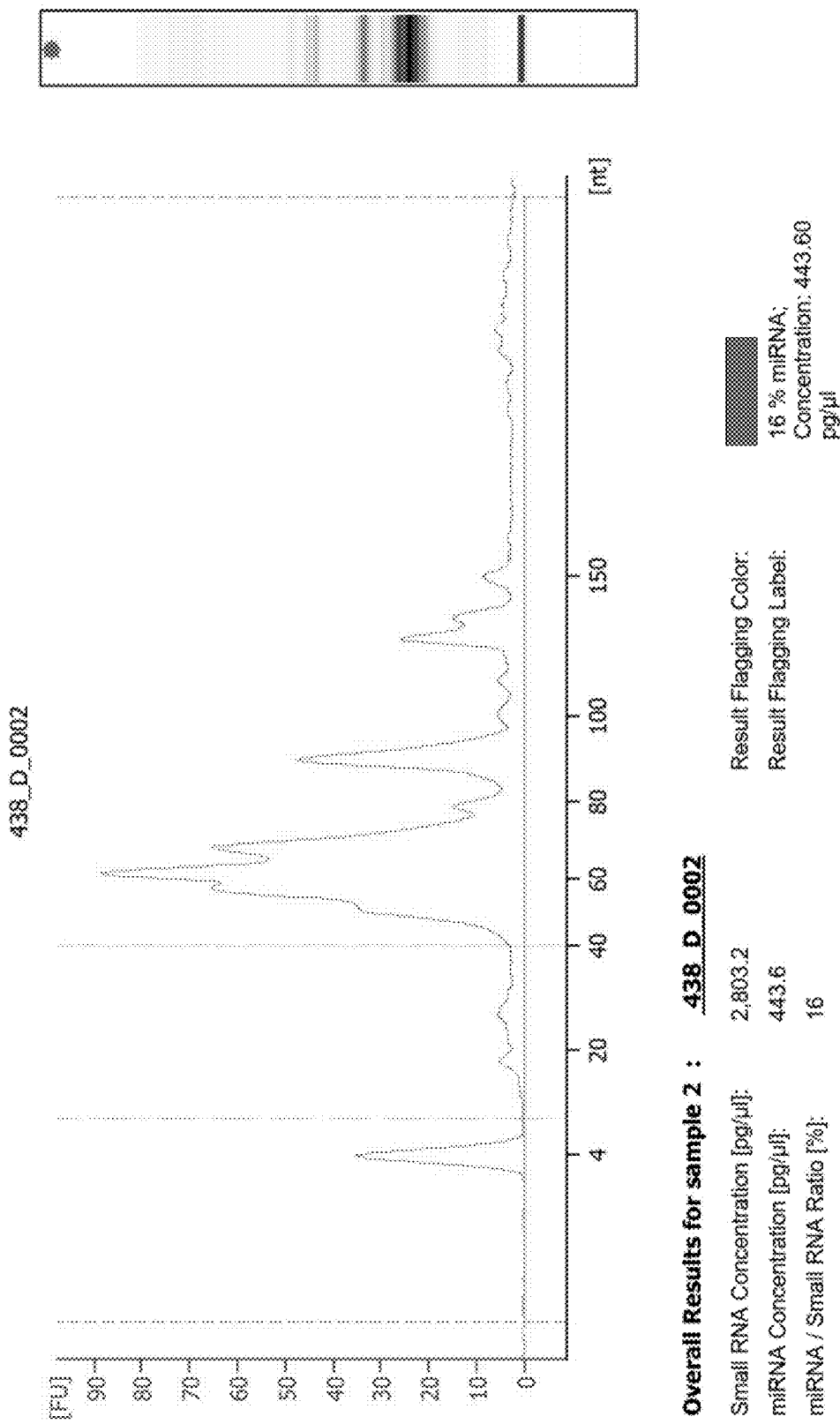
FIG. 3: Close-up of the small RNA fraction with <200 nt in length derived from a whole blood sample from which the RNA-fraction of >200 nt in length has been removed by use of a hydrophilic polymeric absorbent probe. Herein, said small RNA-fraction comprises various small-RNA species, such as miRNA (~15-35 nt), tRNA (~60-80 nt), siRNA (~20-25 nt), piRNA (~26-31 nt) or snorRNA.
Figure 4B:
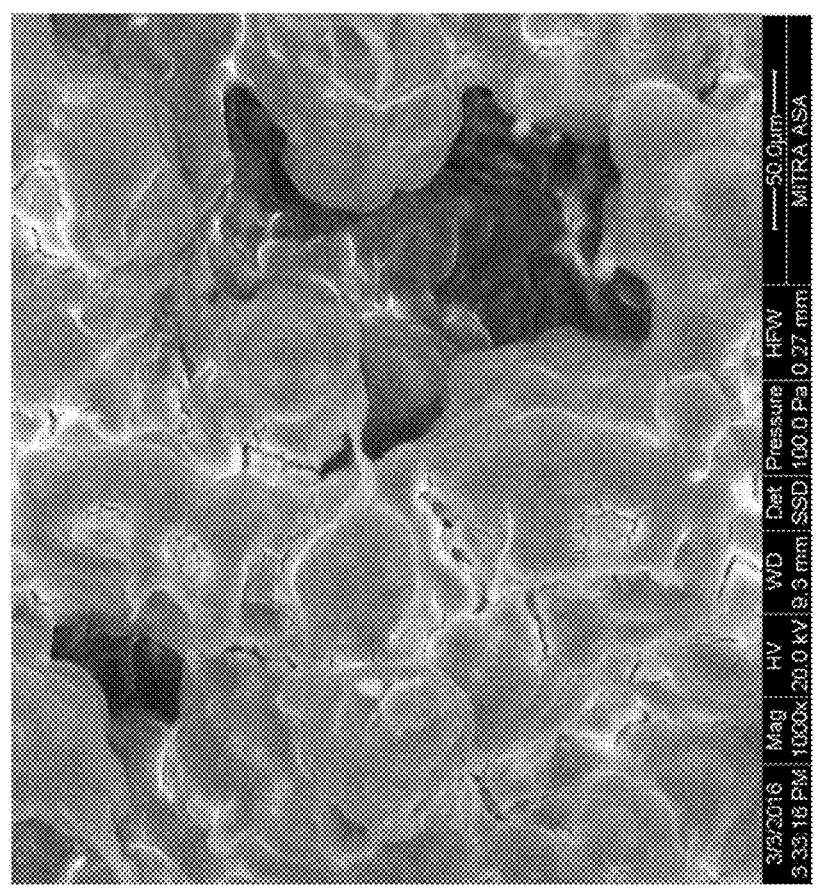
FIGS. 4A and 4B: Scanning electron microscope (SEM) images of hydrophilic polymeric absorbent probes.
Figure 4A:
Figure 6:
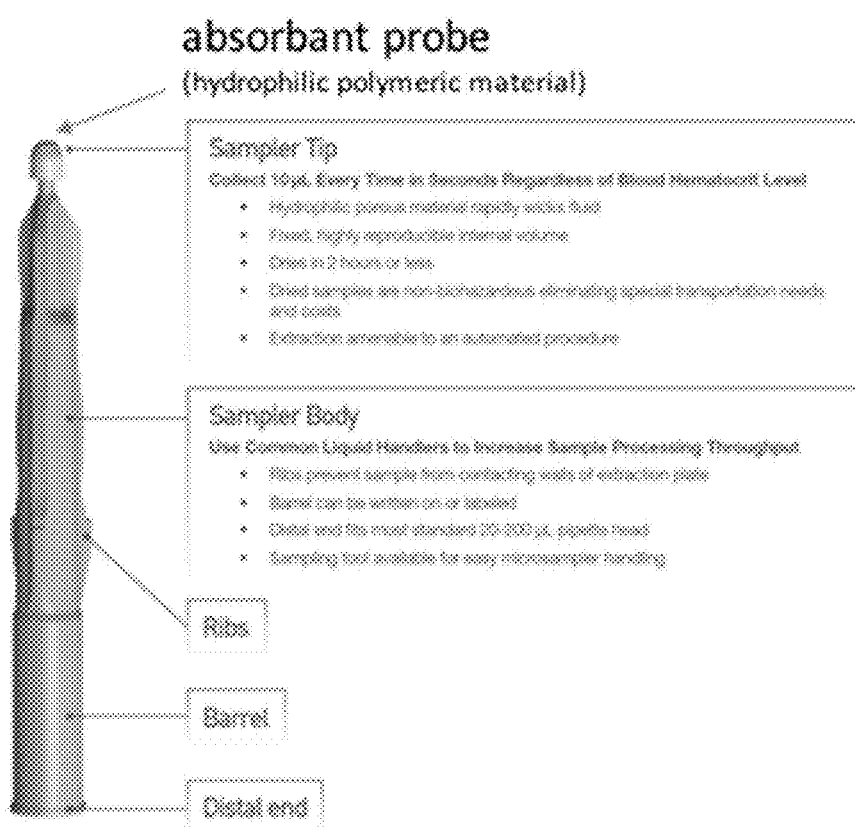
FIG. 6: Mitra Microsampling Device: the hydrophilic absorbent probe is comprised in the top tip of said device.
Figure 7:
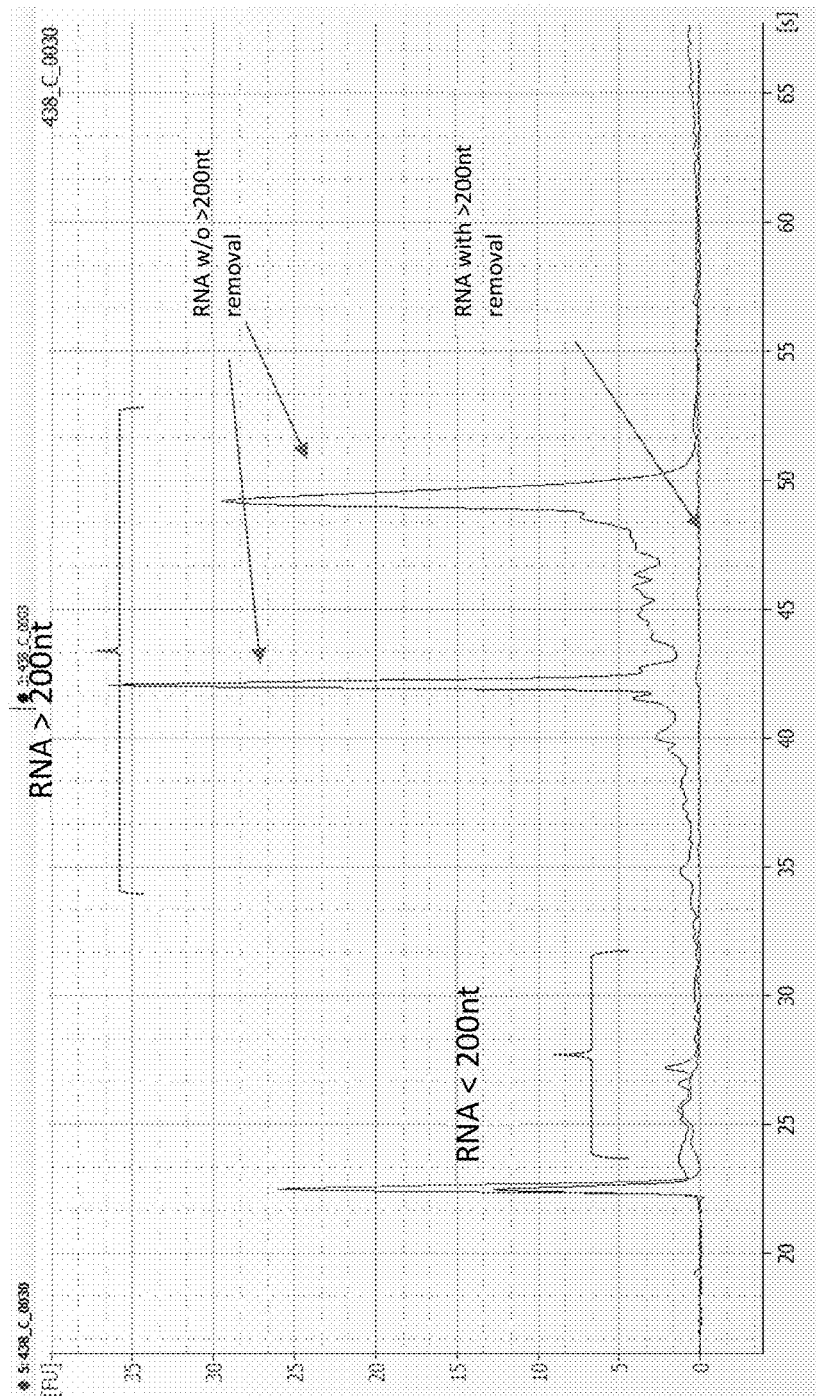
FIG. 7: Depicted is the comparison of the Agilent Bioanalyzer Nano results of RNA isolated from whole blood samples (i) with removal of the RNA-fraction with >200 nt in length making use of an absorbent probe (hydrophilic cellulose comprising absorbent device such as Non-Indicating FTA Classic Card (GE Healthcare Life Science, Buckinghamshire, Great Britain), Non-Indicating FTA Elute Micro Card (GE Healthcare Life Science, Buckinghamshire, Great Britain), HemaSpot HF (Spot On Sciences, Austin, Tex., USA), HemaSpot SE (Spot On Sciences, Austin, Tex., USA), TFN (Munktell, Bärenstein, Germany), TFN-Di (Munktell, Bärenstein, Germany)), lower curve) and (ii) without removal of the RNA-fraction with >200 nt in length (whole blood collected in PAXgene Blood RNA Tube, upper curve) from a human individual. The upper curve clearly shows that the mayor RNA peaks (18S, 28S ribosomal RNA ist still present, while in the lower curve said 18S and 28S RNAs and other RNA species with >200 nt in length have been effectively removed by absorbing the whole blood sample to an absorbent probe of hydrophilic polymeric material.

Blood was collected from different individuals (n=3) by puncture of the middle finger of the left hand using sterile safety lancets (Safety-Lancet Extra 18G, Sarstedt, Nümbrecht, Germany) and four Mitra Microsampling Devices (neoteryx, Torrance, Calif., USA, Ordering No. 10005) per individual. Blood on Mitra Microsampling Device (FIG. 6) was dried for 2 hours at ambient temperature. Four blood filled Sampler Tips per individual were removed from Sampler Body of the Mitra Microsampling Device and transferred to a 2 ml Tube (Eppendorf, Hamburg, Germany)

Example 2: Extraction of Small RNA from Mitra Microsampling Device

Small RNA extraction with length <200 nt (including the microRNA-fraction) was carried out using Phenol-Chloroform extraction technique. Purification of the small RNA was performed by use of the miRNeasy® Serum Plasma Kit (Qiagen GmbH, Hilden, Germany). Herein, 1 mL Qiazol reagent (Qiagen GmbH, Hilden, Germany, comprising guanidinium thiocyanate as a chaotropic reagent and phenol) was pipetted to the 2 mL tube containing four Mitra Sampler Tips (see Example 1, blood sample collection). The tube was then incubated at 4° C. on a shaker at 1,000 rpm for 16 hours. Afterwards, complete supernatant was transferred to a fresh 2 mL Eppendorf tube. After addition of 200 µl Chloroform, mixture was thoroughly vortexed for 15 sec and incubated for 2 min at room temperature, followed by centrifugation at 12,000×g for 15 min at 4° C. Afterwards, the upper, aqueous phase was transferred to a new 1 mL tube without touching the other two phases. 1.5 volumes of 100% ethanol were added to the aqueous phase, thoroughly mixed by pipetting and incubated for 10 min at room temperature. 700 µl of the sample were then transferred into a Qiagen MinElute® column and centrifuged at 13,000 rpm for 15 sec at RT, discarding the flow-through. The last two steps were repeated until complete sample volume was applied to the column. Afterwards, 700 µl of buffer RWT were added to each column, centrifuged again at 13,000 rpm for 15 sec at RT, discarding the flow-through. Then 500 µl Buffer RPE was added to the column and centrifuged at 13,000 rpm for 15 sec at RT, discarding the flow-through. Afterwards 500 µl 80% ethanol was added to the column and centrifuged at 13,000 rpm for 2 min at RT, discarding the flow-through. Then the column was placed into a new 2 ml collection tube, and centrifuged with open lid at 13,000 rpm for 5 min at RT to dry it. The column was transferred into anew 1.5 ml collection tube. For elution of the total RNA incl. microRNA 14 µl RNase-free water was pipetted onto the column, incubated for 1 min and centrifuged at 13.000 rpm at RT for 1 min. Another 14 µl of RNase-free water was pipetted to the column, incubated for 1 min at RT and centrifuged at 13.000 rpm at RT for 1 min. The eluted small RNA fraction with length <200 nt (including the microRNA-fraction) was stored on ice until Quality Control and quantification.

Example 3: Blood Sample Collection Using a Hydrophilic Cellulose Comprising Absorbent Device Blood was collected from different individuals (n=3) by puncture of the ring finger of the left hand using sterile safety lancets (Safety-Lancet Extra 18G, Sarstedt, Nümbrecht, Germany). Two blood drops per individual were added to the hydrophilic cellulose comprising absorbent device (cellulose comprising filter paper from various manufactures, including Non-Indicating FTA Classic Card (GE Healthcare Life Science, Buckinghamshire, Great Britain), Non-Indicating FTA Elute Micro Card (GE Healthcare Life Science, Buckinghamshire, Great Britain), HemaSpot HF (Spot On Sciences, Austin, Tex., USA), HemaSpot SE (Spot On Sciences, Austin, Tex., USA), TFN (Munktell, Bärenstein, Germany), TFN-Di (Munktell, Bärenstein, Germany)) covering an area of approximate 0.5-4.0 square cm The various hydrophilic cellulose comprising absorbent probes were dried for 2 hours and then stored for 1 week at ambient temperature. Blood absorbed area of the hydrophilic cellulose comprising absorbent probes were cut out and transferred to a 2 mL Tube (Eppendorf, Hamburg, Germany).

Example 4: Extraction of Small RNA from a Hydrophilic Cellulose Comprising Absorbent Device Small RNA with a length <200 nt (including the microRNA-fraction) extraction was carried out using Phenol-Chloroform extraction technique. Purification of small RNA was performed by use of the miRNeasy® Serum Plasma Kit (Qiagen GmbH, Hilden, Germany). 1 mL Qiazol reagent (Qiagen GmbH, Hilden, Germany) was pipetted to the 2 mL tube containing the hydrophilic cellulose comprising absorbent device to which the whole blood sample was absorbed to by drying (see blood sample collection, example 3). The tube was then incubated at 4° C. on a shaker at 1,000 rpm for 16 hours. Afterwards, complete supernatant was transferred to a fresh 2 mL Eppendorf tube. After addition of 200 µl Chloroform, mixture was thoroughly vortexed for 15 sec and incubated for 2 min at room temperature, followed by centrifugation at 12,000×g for 15 min at 4° C. Afterwards, the upper, aqueous phase was transferred to a new 2 mL tube without touching the other two phases. 1.5 volumes of 100% ethanol were added to the aqueous phase, thoroughly mixed by pipetting and incubated for 10 min at room temperature. 700 µl of the sample were then transferred into a Qiagen MinElute® column and centrifuged at 13,000 rpm for 15 sec at RT, discarding the flow-through. The last two steps were repeated until complete sample volume was applied to the column. Afterwards, 700 µl of buffer RWT were added to each column, centrifuged again at 13,000 rpm for 15 sec at RT, discarding the flow-through. Then 500 µl Buffer RPE was added to the column and centrifuged at 13,000 rpm for 15 sec at RT, discarding the flow-through. Afterwards 500 µl 80% ethanol was added to the column and centrifuged at 13,000 rpm for 2 min at RT, discarding the flow-through. Then the column was placed into a new 2 ml collection tube, and centrifuged with open lid at 13,000 rpm for 5 min at RT to dry it. The column was transferred into anew 1.5 ml collection tube. For elution of the small RNA incl. microRNA 14 µl RNase-free water was pipetted onto the column, incubated for 1 min and centrifuged at 13.000 rpm at RT for 1 min. Another 14 µl of RNase-free water was pipetted to the column, incubated for 1 min at RT and centrifuged at 13.000 rpm at RT for 1 min. The eluted small RNA with <200 nt in length (incl. microRNA) was stored on ice until Quality Control and quantification.

Example 5: Blood Sample Collection Using PaxGene Blood RNA Tubes

Blood was collected from different individuals (n=3). Herein, for each blood donor 2.5 ml of whole blood was collected by venous puncture into a PAXgene Blood RNA Tube (PreAnalytix, Hombrechticon, Switzerland). The blood cells were derived/obtained from processing the whole blood samples by centrifugation. Herein, the blood cells from the whole blood collected in said blood collection tubes were spun down by 10 min, 5000×g centrifugation. The blood cell pellet (the cellular blood fraction comprising red blood cells, white blood cells and platelets) was harvested for further processing, while the supernatant (including the extra-cellular blood fraction) was discarded. Total RNA, including the small RNA (<200nt including the miRNA-fraction), but also the >200 nt RNA fraction was extracted from the harvested blood cells using the miRNeasy Mini Kit (Qiagen GmbH, Hilden, Germany); for details see Example 6.

Example 6: Extraction of Total RNA (Incl. RNA-Fraction with >200 nt) from PAXgene Blood RNA Tubes The isolation of total RNA, including the small RNA (<200nt including the miRNA-fraction) and the >200 nt RNA fraction was performed by use of the miRNeasy® Mini Kit (Qiagen GmbH, Hilden, Germany). Herein, the blood cell pellet (obtained as outlined in Example 5) was thoroughly resuspended in 700 µl QIAzol lysis reagent by pipetting up and down and immediately the suspension was transferred to a new 1.5 ml Eppendorf tube. Then 140 µl chloroform were added, vortexed thoroughly and incubated for 2-3 min at room temperature, followed by centrifugation at 12,000 g for 15 min at 4° C. Afterwards, the upper, aqueous phase was transferred to a new 2 ml tube with great care, without touching the other two phases. Then 1.5 volumes of 100% ethanol were added to the transferred aqueous phase and thoroughly mixing was done by pipetting. 700 µl of sample were then transferred into a column and centrifuged at 13,000 rpm for 15 sec at RT, discarding the flow-through. Afterwards 700 µl of Buffer RWT were added to each column, centrifuged again at 13,000 rpm for 15 sec at RT, discarding the flow-through. Then 500 µl Buffer RPE was added to the column and centrifuged at 13,000 rpm for 15 sec at RT, discarding the flow-through. Afterwards another 500 µl Buffer RPE was added to the column and centrifuged at 13,000 rpm for 2 min at RT, discarding the flow-through. Then the column was placed into a new 2 ml collection tube and centrifuged at 13,000 rpm for 1 min at RT to dry it. The column was transferred into a new 1.5 ml collection tube. For elution of the total RNA incl. microRNA 40 µl RNase-free water was pipetted onto the column and incubated for 1 min, centrifuged at 13.000 rpm at RT for 1 min. Then the eluate was put back onto the same column, incubated for 1 min at RT and centrifuged again for 1 min. The eluted total RNA, including the small RNA (<200nt, including the miRNA-fraction) and the ≥200 nt RNA fraction was quantified using the Nano-Drop 1000 and stored at −20° C. before use in expression profiling experiments.

Example 7: Quality Control of Small RNA Fraction

Quality control and quantification of extracted RNA was performed by using Agilent's Bioanalyzer (Agilent Technologies, Santa Clara, Calif., USA) according to manufacturer's protocol and the Bioanalyzer Small and Nano Assay. The RNA was denatured for 2 min at 70° C., afterwards 1 µl was applied to the Bioanalyzer Chip for both Small and Nano Assay. Chips were vortexed at 2,400 rpm and run on Bioanalyzer Instrument within 5 min.

Example 8: Microarray-Based Determination of microRNA Expression Profiles

Total RNA sample including microRNA-fraction was analyzed on Agilent human miRNA 8×60k microarray (release v21) according to manufacturer's protocol. After enzymatic Cy3-labeling of microRNA and 20 hours of array hybridization at 55° C. in a rotating hybridization oven, the microarray slide was washed twice (non-stringent and stringent) and afterwards scanned with Agilent's SureScan Microarray Scanner. Resulting image data was evaluated using Agilent Feature Extraction software (v11). Raw data files (GeneView) generated by Feature Extraction software were imported in Excel for present call analysis.

Part II:

It has further systematically be explored whether dried blood spots (DBS) facilitate stable miRNA measurements and compared technical stability to biological variability. First, the stability of DBS samples by generating whole-genome wide miRNA profiles of samples from the same individuals exposed to different environmental conditions (e.g. temperature and humidity) was tested. Second, technical reproducibility by performing seven replicates of samples taken from the same individual was investigated. Third, samples from 53 lung cancer patients undergoing different therapies were investigated. Across the three stages, 108 genome-wide miRNA profiles were generated and evaluated by biostatistical means.

Material and Methods

Sample collection: For the study, a total of 78 samples on dried blood spots were collected. TFN paper from (Munktell, Bärenstein, Germany) (Ahlstrom) was used. After arrival, dried blood spots were stored at −80 degrees Celsius until RNA extraction. For the stability analysis, one individual was included and exposed to different environmental conditions. The temperature was varied between 26 and 35 degrees Celsius, the humidity between 38.5 and 60%. To capture reproducibility across the whole workflow, i.e. between different extractions and also on different microarrays, we performed 7 technical replicates of another individual. The respective sample has been measured as process control along with the lung cancer study. The same individual has also been investigated using PAXGene Blood Tubes (BD) to compare the miRNA repertoire on dried blood spots and using the blood tubes. As clinical case, 53 lung cancer samples exposed to different therapy regimens were investigated. In detail, 17 samples belonged to patients with curative (adjuvant) therapy and 36 samples to patients with palliative care. The adjuvant therapy was additionally applied to the primary surgically therapy to improve the chances of cure, while the palliative care was used for improving quality of life is case of advances cancer. The study has been approved by the local ethics committee and participants gave written informed consent. Blood samples have been collected on dried blood spots. All samples were measured on miRBase V21 microarrays (Agilent). A subset of 26 samples has also been measured on miRBase V19 microarrays (Agilent) in order to compare the different microarrays. In total, 30 whole miRNomes were profiled on V19 and 78 whole miRNomes on V21 microarrays.

miRNA extraction: Prior to RNA extraction, DBS samples were thawed at RT for one hour. Complete blood drop was cut out and transferred to a 2 mL Eppendorf tube. DBS papers were incubated for 16 hours in 1 mL Qiazol Lysis Reagent (Qiagen GmbH, Hilden, Germany) on a shaker at 1.000 rpm and 4 degrees Celsius. Supernatant was transferred to a fresh 2 mL tube for further processing. RNA extraction and purification was performed using Qiagen's miRNeasy® Serum/Plasma Kit (Qiagen GmbH, Hilden, Germany). RNA content and miRNA quality was checked (Quality Control and quantification of RNA eluates were performed) with Agilent 2100 Bioanalyzer using the Small RNA Kit according to manufacturer's instructions (Agilent Technologies, Santa Clara, USA).

miRNA measurement: For microRNA expression profiling, samples were analyzed on Agilent Sureprint G3 Human miRNA (8×60k) microarray slides with latest miRBase v21 content. Each array targets 2,549 microRNAs with 20 replicates per probe. Additionally, a part of the samples was measured on previous v19 version of Agilent's Sureprint miRNA Slides for technical evaluation. Extracted microRNA was labeled and hybridized using miRNA Complete Labeling and Hybridization Kit from Agilent according to manufacturer's protocol. After rotating hybridization for 20 hours at 55 degrees Celsius, slides were washed twice and scanned on Agilent's SureScan Microarray Scanner. Image files from the scanner were transformed to text raw data using Feature Extraction Software (Agilent Technologies).

Data preprocessing: For the preprocessing of the profiled samples, the Bioconductor library AgiMicroRna, that is designed to preprocess and analyze microRNA Agilent microarray data, was applied. The processed expression values were produced in the following three steps by the robust multiarray average (RMA) algorithm. The measured signal of a probe (one of 20 probe replicates for a miRNA) were first background corrected, then the arrays were normalized by quantile, and at last, the final signal of a miRNA was estimated by summarizing the corresponding probe signals. By applying an additional filtering, control features and miRNAs that are not detected in any experimental group are removed from the data set to obtain only expressed features for the bioinformatics analyses.

Bioinformatics analyses: To assess technical reproducibility, Pearson's correlation was computed for the process controls. Thereby, a comparison between chips belonging to one miRBase version and a comparison between chips belonging to different miRBase versions (v19 and v21) was made. At the same time, the coefficient of variation (CV) was estimated for relative miRNA expression values of the technical replicates. These miRNAs were also analyzed regarding their GC content and their first introduction to miRBase.

Furthermore, hierarchical clustering approach was applied for evaluation of the experimental groups and categories in terms of different environmental conditions like humidity and temperature. The measure of distance between pairs of observations was based on Euclidean distance.

For biostatistical evaluation to find candidates distinguishing between the three groups (adjuvant, palliative and process controls), pairwise comparisons have been performed using t-test. To control the false discovery rate, all p-values were adjusted by using Benjamin-Hochberg adjustment. Additional to the significance values, the Area Under the Receiver Operating Characteristics Curve (AUC) value was calculated.

Results

Aim of the study was to understand whether genome-wide miRNA profiles from dried blood spots can be reliably measured, facilitating the application in disease diagnosis. A three-staged approach was carried out. First, replicates under different environmental conditions were profiled. Second, technical replicates as process control were established and measured on a series of microarrays. Third, clinical feasibility was tested using lung cancer patient samples. An overview of the number of measured miRNomes in the three stages is presented in Table 1 below.

TABLE 1

Number of whole miRNomes measured in each stage

| miRBase Version | Environmental factors [technical stability] | Process controls [technical stability] | Lung Cancer Therapy [biological variability] |
|---|---|---|---|
| V19 | — | 4 | 26 |
| V21 | 18 | 7 | 53 |

Stability of miRNomes from Dried Blood Spots

Figure 8A:
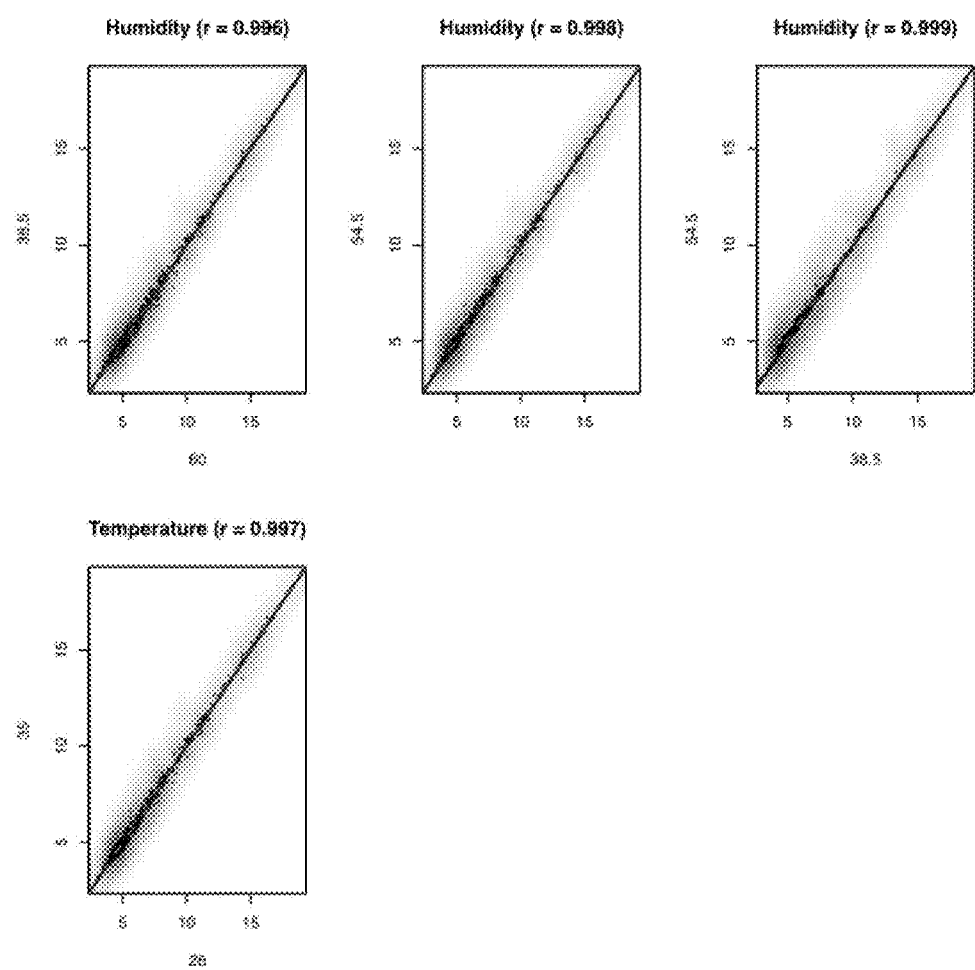
FIGS. 8A and 8B: Stability of miRNomes from dried blood spots.
Figure 8B:
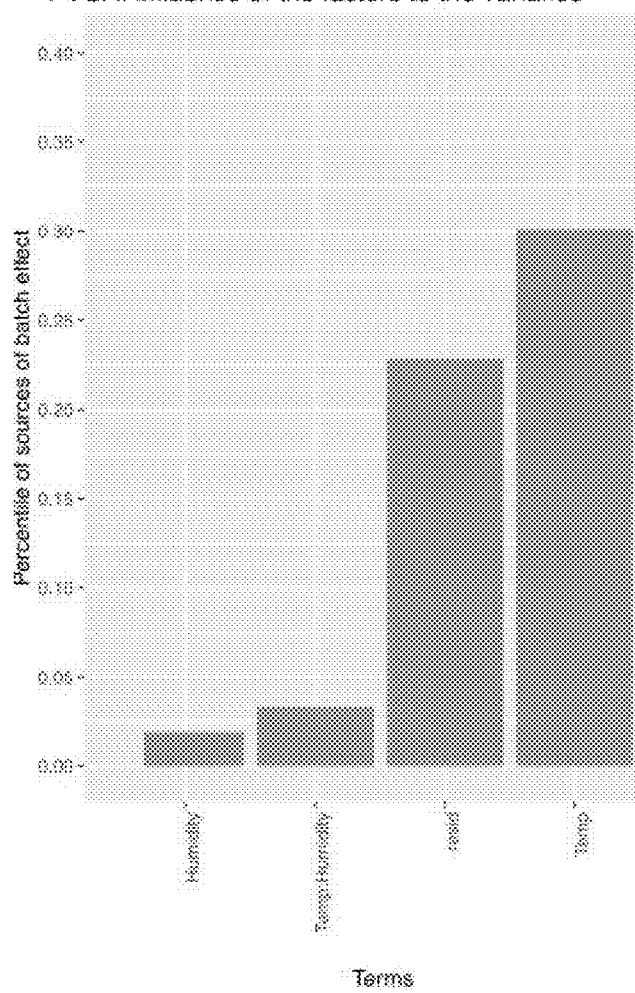

MiRNAs were extracted from a series of dried blood spot samples exposed to different environmental conditions. Combinations of three temperatures and three humidity levels were explored, while each combination was measured in triplicates. Thus, by having six combinations in form of triplicates, a total of 18 miRNomes has been profiled on microarrays. A cluster heat-map was established (data not shown). The different conditions were compared with each other. The results are shown in FIG. 8A. The lowest correlation of 0.997 was calculated for the temperature. The highest correlation—corresponding to the lowest influence—was calculated for the humidity (correlation of 0.999). These results have been also confirmed by a principal variant component analysis (see FIG. 8B). These results show that miRNAs measured from dried blood spots have an inherent stability and are technically suited as carriers of diagnostic information, even if they are exposed to varying conditions, e.g. induced by shipment of samples to a central lab.

Reproducibility of miRNAs Over Time

Next, it was explored how reproducible miRNomes from dried blood spots can be profiled on microarrays. From one individual, seven technical replicates on seven different Agilent slides (the Agilent technique allows for parallel processing of 8 samples on 8 physically separated arrays on one slide) were performed. In this regard, the sample to be processed can also be considered as a process control (=healthy control). The mean correlation of these process controls was as high as 0.993. The same measurements have been repeated with the previous version of the Agilent microarrays from miRBAse version 19 instead of 21. Here, four process controls were included, leading to comparable correlation (data not shown). As the results in the previous analysis, the replicated process controls from one individual underline that miRNAs from dried blood spots are—from a technical perspective—suited as diagnostic tools.

Biological Variation Depending on Lung Cancer Therapy

As last, the biological variation between the samples of lung cancer patients and the process controls were investigated. This was realized in two steps. First, 30 samples (26 lung cancer and four process controls) on Agilent microarrays from both versions, V19 and V2, were profiled. 1. By applying hierarchical clustering, for each version two clusters with similar sample distribution were obtained (data not shown). Not only the samples with the same therapy form had a tendency to cluster together but also the process controls fell in one cluster. In the second step, 60 samples (53 lung cancer and the afore mentioned 7 process controls) were profiled on Agilent microarrays from miRBase V21. The average correlation of this analysis step was 0.974. While the average correlation for the process controls (0.993) and the lung cancer samples (0.976) exceeded this value, the lowest average correlation (0.967) was calculated between process controls and lung cancer samples.

Figure 9:
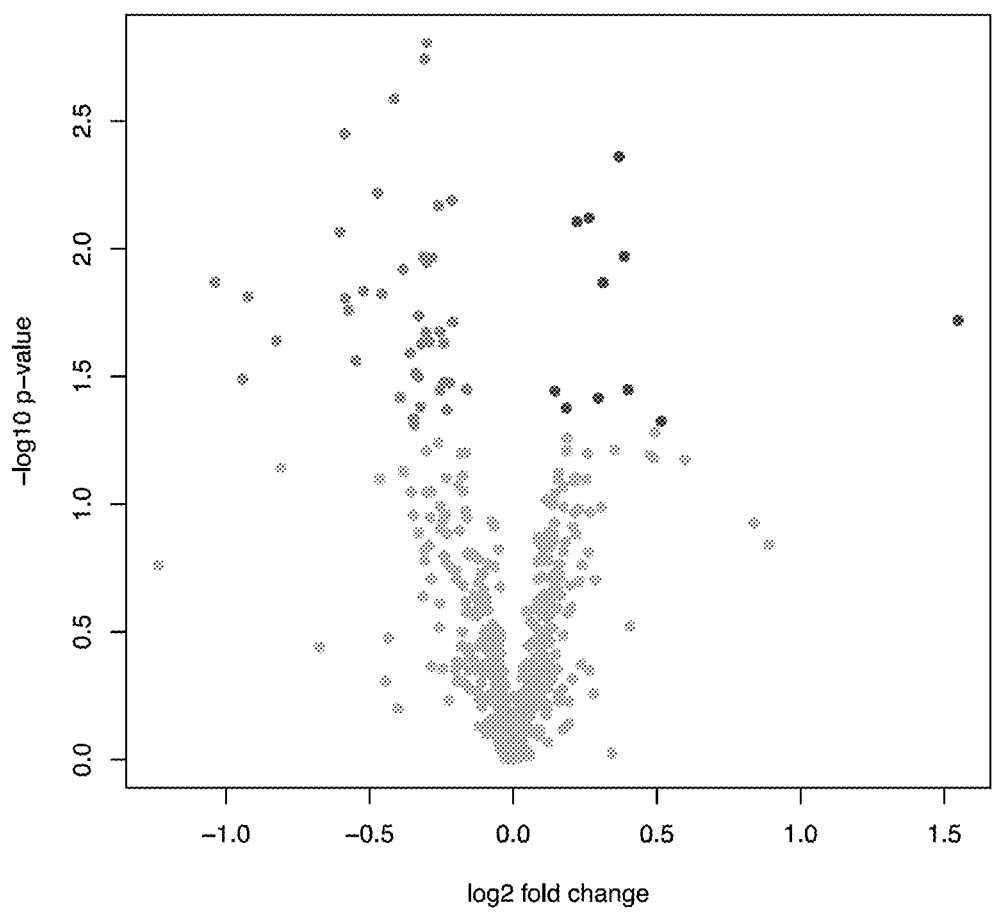
FIG. 9: Volcano plot of deregulated miRNAs regarding the comparison between adjuvant and palliative treated patients.

Further of interest were the differences between two different lung cancer treatment cohorts. Therefore, statistical pairwise comparisons between the groups "adjuvant" and "palliative" treated patients were preformed next by using two-tailed t-test. Due to the exploratory nature of the study, miRNAs with raw p-values <0.05 were considered as significantly deregulated. For the above-mentioned comparison (adjuvant vs. palliative), 51 significant deregulated miRNAs (8.6% of all 591 expressed miRNAs) were found based on two-tailed t-tests and the selected alpha-level of 0.05. Of these 51 miRNAs, 11 had higher expression in the adjuvant group (20%). The most up-regulated miRNA with a p-value of 0.019 was hsa-miR-150-5p, the most down-regulated marker with p-value of 0.014 was hsa-miR-642a-3p. All miRNAs are shown in the volcano plot in FIG. 9, where up- and down-regulated miRNAs are highlighted in dark grew (right upper corner) and light grew (left upper corner) respectively. Detailed information on expression intensities, fold changes, p-values and the area under the receiver operator characteristics curve (AUC value) are provided in FIG. 10.

Discussion

A growing number of studies dealt with miRNAs as non-invasive-biomarkers for various human diseases. In many cases, these miRNAs were derived from serum, plasma or whole blood. While preservation tubes like PAXgene and EDTA are commonly used, the investigation of miRNAs from DBS is still a new ground.

In the present study, the reliability of measurements of miRNA from DBS was analyzed by going after the following three aspects: (1) sample stability under different environmental conditions, (2) technical stability and reproducibility between chip versions, and (3) comparison of clinical samples using the example of lung cancer patients.

Regarding the first aspect, it has been shown that the measured miRNAs from DBS had high stability by considering the comparisons of the different environmental conditions (humidity and temperature) within one category.

In the second part of the study, it has been shown with the process controls on the one side that the equal and high correlations give evidences for technical stability across the different chip versions V19 and V21. On the other side, the clustering pattern of the clinical samples and process controls from V21 could also be retrieved with similar structure from v19. These similar results indicate the high reproducibility of miRNAs measured in DBS despite different miRBase versions on the chips.

The third part of the study was about the clinical comparison between the three different groups: process controls, patients getting adjuvant and patients getting palliative therapy. In case of statistical significance of deregulated miRNAs, there was a very high number of significant miRNAs (adjusted p-value <0.05) between lung cancer patients and process controls. This high number could be caused by the lung cancer disease itself and the application of the therapies.

The invention claimed is:

1. A method of separating an RNA fraction with <200 nucleotides in length from an RNA fraction with ≥200 nucleotides in length comprised in a whole blood sample, the method comprising the steps of:
   providing an absorbent probe comprising a hydrophilic polymeric material into which whole blood from the whole blood sample has been absorbed, wherein the hydrophilic polymeric material has a density of ≤6 g/cm$^3$ and is selected from the group consisting of cotton, a polysaccharide, a polyolefin, and a polyester,
   (ii) contacting the absorbent probe with a fluid comprising a chaotropic agent for a time period of 29 minutes to 20 hours, and
   (iii) recovering the fluid from step (ii), thereby separating the RNA fraction with <200 nucleotides in length, which is in the recovered fluid, from the RNA fraction with ≥200 nucleotides in length, which remains absorbed to the hydrophilic polymeric material.

2. The method of claim 1, wherein the hydrophilic polymeric material has a density of ≤4 g/cm$^3$.

3. The method of claim 1, further comprising step (iv) of: isolating the RNA fraction with <200 nucleotides in length from the recovered fluid by one or more separation techniques selected from the group consisting of centrifugation, evaporation/reconstitution, concentration, precipitation, liquid/liquid extraction, and solid phase extraction.

4. The method of claim 3, further comprising step (v) of: determining in the RNA fraction isolated in step (iv) the level of RNA molecules with <200 nucleotides in length.

5. The method of claim 4, wherein the level of RNA molecules with <200 nucleotides in length is determined by a technique selected from the group consisting of nucleic acid hybridization, nucleic acid amplification, polymerase extension, sequencing, and mass spectroscopy, or any combination thereof.

6. The method of claim 1, wherein
   (i) the polysaccharide is cellulose,
   (ii) the polyolefin is selected from the group consisting of polyethylene, polypropylene, polybutylene, polyisobutylene, and polymethylpentene, or
   (iii) the polyester is selected from the group consisting of polycarbonate and polyethylenterephthalate.

7. The method of claim 1, wherein the chaotropic agent comprises guanidinium thiocyanate, guanidinium isothiocyanate, guanidinium hydrochloride, guanidinium chloride, alkali thiocyanate, alkali isothiocyanate, alkali iodide, or alkali perchlorate.

8. The method of claim 1, wherein the hydrophilic polymeric material is a hydrophilic cellulose.

9. The method of claim 1, wherein the chaotropic agent is guanidinium thiocyanate.

10. A method for diagnosing a disease in an individual comprising the steps of:
    carrying out the method of claim 1, wherein the whole blood sample is from an individual,
    (ii) determining the level of RNA molecules with <200 nucleotides in length by a suitable technique,
    (iii) comparing said level to one or more reference level(s), and
    (iv) diagnosing or differentially diagnosing whether the individual is afflicted by the disease based on the comparison; or
    (i) carrying out the method of claim 6, wherein the whole blood sample is from an individual,
    (ii) comparing said level to one or more reference level(s), and
    (iii) diagnosing or differentially diagnosing whether the individual is afflicted by the disease based on the comparison.

11. The method of claim 10, wherein the suitable technique is selected from the group consisting of nucleic acid hybridization, nucleic acid amplification, polymerase extension, sequencing, mass spectroscopy and any combination thereof.

12. The method of claim 10, wherein the one or more reference level(s) are from:
    one or more healthy subject(s),
    one or more subject(s) suffering from a disease, and/or
    one or more subject(s) suffering from another disease.

* * * * *

SEQUENCE LISTING

```
<160> NUMBER OF SEQ ID NOS: 475

<210> SEQ ID NO 1
<211> LENGTH: 22
<212> TYPE: RNA
<213> ORGANISM: Homo sapiens

<400> SEQUENCE: 1
aaaccguuac cauuacugag uu                                              22

<210> SEQ ID NO 2
<211> LENGTH: 22
<212> TYPE: RNA
<213> ORGANISM: Homo sapiens

<400> SEQUENCE: 2
uagcagcacg uaaauauugg cg                                              22

<210> SEQ ID NO 3
<211> LENGTH: 22
<212> TYPE: RNA
<213> ORGANISM: Homo sapiens

<400> SEQUENCE: 3
uagcagcaca ucaugguuua ca                                              22

<210> SEQ ID NO 4
<211> LENGTH: 20
<212> TYPE: RNA
<213> ORGANISM: Homo sapiens

<400> SEQUENCE: 4
uacaguauag augauguacu                                                 20
```

```
<210> SEQ ID NO 5
<211> LENGTH: 22
<212> TYPE: RNA
<213> ORGANISM: Homo sapiens

<400> SEQUENCE: 5
ugagguagua gguuguauag uu                                              22

<210> SEQ ID NO 6
<211> LENGTH: 23
<212> TYPE: RNA
<213> ORGANISM: Homo sapiens

<400> SEQUENCE: 6
ugugcaaauc caugcaaaac uga                                             23

<210> SEQ ID NO 7
<211> LENGTH: 22
<212> TYPE: RNA
<213> ORGANISM: Homo sapiens

<400> SEQUENCE: 7
ugagguagua gauuguauag uu                                              22

<210> SEQ ID NO 8
<211> LENGTH: 22
<212> TYPE: RNA
<213> ORGANISM: Homo sapiens

<400> SEQUENCE: 8
ugagguagua gguugugugg uu                                              22

<210> SEQ ID NO 9
<211> LENGTH: 23
<212> TYPE: RNA
<213> ORGANISM: Homo sapiens

<400> SEQUENCE: 9
uaaagugcuu auagugcagg uag                                             23

<210> SEQ ID NO 10
<211> LENGTH: 22
<212> TYPE: RNA
<213> ORGANISM: Homo sapiens

<400> SEQUENCE: 10
uccuguacug agcugccccg ag                                              22

<210> SEQ ID NO 11
<211> LENGTH: 22
<212> TYPE: RNA
<213> ORGANISM: Homo sapiens

<400> SEQUENCE: 11
uagcagcaca uaaugguuug ug                                              22

<210> SEQ ID NO 12
<211> LENGTH: 21
<212> TYPE: RNA
<213> ORGANISM: Homo sapiens

<400> SEQUENCE: 12
uucaaguaau ucaggauagg u                                               21
```

```
<210> SEQ ID NO 13
<211> LENGTH: 23
<212> TYPE: RNA
<213> ORGANISM: Homo sapiens

<400> SEQUENCE: 13
uguaguguuu ccuacuuuau gga                                              23

<210> SEQ ID NO 14
<211> LENGTH: 22
<212> TYPE: RNA
<213> ORGANISM: Homo sapiens

<400> SEQUENCE: 14
ugagguagua guuuguacag uu                                               22

<210> SEQ ID NO 15
<211> LENGTH: 22
<212> TYPE: RNA
<213> ORGANISM: Homo sapiens

<400> SEQUENCE: 15
ugagguagua guuugugcug uu                                               22

<210> SEQ ID NO 16
<211> LENGTH: 21
<212> TYPE: RNA
<213> ORGANISM: Homo sapiens

<400> SEQUENCE: 16
uaaagugcug acagugcaga u                                                21

<210> SEQ ID NO 17
<211> LENGTH: 23
<212> TYPE: RNA
<213> ORGANISM: Homo sapiens

<400> SEQUENCE: 17
agcagcauug uacagggcua uca                                              23

<210> SEQ ID NO 18
<211> LENGTH: 22
<212> TYPE: RNA
<213> ORGANISM: Homo sapiens

<400> SEQUENCE: 18
cauugcacuu gucucggucu ga                                               22

<210> SEQ ID NO 19
<211> LENGTH: 23
<212> TYPE: RNA
<213> ORGANISM: Homo sapiens

<400> SEQUENCE: 19
ugugcaaauc uaugcaaaac uga                                              23

<210> SEQ ID NO 20
<211> LENGTH: 22
<212> TYPE: RNA
<213> ORGANISM: Homo sapiens

<400> SEQUENCE: 20
ugucaguuug ucaaauaccc ca                                               22
```

```
<210> SEQ ID NO 21
<211> LENGTH: 17
<212> TYPE: RNA
<213> ORGANISM: Homo sapiens

<400> SEQUENCE: 21
uggagagaaa ggcagua                                                  17

<210> SEQ ID NO 22
<211> LENGTH: 22
<212> TYPE: RNA
<213> ORGANISM: Homo sapiens

<400> SEQUENCE: 22
uauugcacuu gucccggccu gu                                            22

<210> SEQ ID NO 23
<211> LENGTH: 22
<212> TYPE: RNA
<213> ORGANISM: Homo sapiens

<400> SEQUENCE: 23
ggauaucauc auauacugua ag                                            22

<210> SEQ ID NO 24
<211> LENGTH: 23
<212> TYPE: RNA
<213> ORGANISM: Homo sapiens

<400> SEQUENCE: 24
agcagcauug uacagggcua uga                                           23

<210> SEQ ID NO 25
<211> LENGTH: 23
<212> TYPE: RNA
<213> ORGANISM: Homo sapiens

<400> SEQUENCE: 25
caaagugcuc auagugcagg uag                                           23

<210> SEQ ID NO 26
<211> LENGTH: 22
<212> TYPE: RNA
<213> ORGANISM: Homo sapiens

<400> SEQUENCE: 26
uagcuuauca gacugauguu ga                                            22

<210> SEQ ID NO 27
<211> LENGTH: 22
<212> TYPE: RNA
<213> ORGANISM: Homo sapiens

<400> SEQUENCE: 27
agagguagua gguugcauag uu                                            22

<210> SEQ ID NO 28
<211> LENGTH: 23
<212> TYPE: RNA
<213> ORGANISM: Homo sapiens
```

-continued

<400> SEQUENCE: 28
caaagugcuu acagugcagg uag                           23

<210> SEQ ID NO 29
<211> LENGTH: 21
<212> TYPE: RNA
<213> ORGANISM: Homo sapiens

<400> SEQUENCE: 29
uacaguacug ugauaacuga a                             21

<210> SEQ ID NO 30
<211> LENGTH: 22
<212> TYPE: RNA
<213> ORGANISM: Homo sapiens

<400> SEQUENCE: 30
uggagagaaa ggcaguuccu ga                            22

<210> SEQ ID NO 31
<211> LENGTH: 18
<212> TYPE: RNA
<213> ORGANISM: Homo sapiens

<400> SEQUENCE: 31
uucccagcca acgcacca                                 18

<210> SEQ ID NO 32
<211> LENGTH: 22
<212> TYPE: RNA
<213> ORGANISM: Homo sapiens

<400> SEQUENCE: 32
ugagguagua gguuguaugg uu                            22

<210> SEQ ID NO 33
<211> LENGTH: 22
<212> TYPE: RNA
<213> ORGANISM: Homo sapiens

<400> SEQUENCE: 33
ucguaccgug aguaauaaug cg                            22

<210> SEQ ID NO 34
<211> LENGTH: 23
<212> TYPE: RNA
<213> ORGANISM: Homo sapiens

<400> SEQUENCE: 34
caaagugcug uucgugcagg uag                           23

<210> SEQ ID NO 35
<211> LENGTH: 22
<212> TYPE: RNA
<213> ORGANISM: Homo sapiens

<400> SEQUENCE: 35
aagcugccag uugaagaacu gu                            22

<210> SEQ ID NO 36
<211> LENGTH: 22
<212> TYPE: RNA

```
<213> ORGANISM: Homo sapiens

<400> SEQUENCE: 36
aauugcacgg uauccaucug ua                                              22

<210> SEQ ID NO 37
<211> LENGTH: 22
<212> TYPE: RNA
<213> ORGANISM: Homo sapiens

<400> SEQUENCE: 37
uuauaauaca accugauaag ug                                              22

<210> SEQ ID NO 38
<211> LENGTH: 21
<212> TYPE: RNA
<213> ORGANISM: Homo sapiens

<400> SEQUENCE: 38
cauaaaguag aaagcacuac u                                               21

<210> SEQ ID NO 39
<211> LENGTH: 22
<212> TYPE: RNA
<213> ORGANISM: Homo sapiens

<400> SEQUENCE: 39
uagcaccauu ugaaaucggu ua                                              22

<210> SEQ ID NO 40
<211> LENGTH: 22
<212> TYPE: RNA
<213> ORGANISM: Homo sapiens

<400> SEQUENCE: 40
uucagauccc agcggugccu cu                                              22

<210> SEQ ID NO 41
<211> LENGTH: 22
<212> TYPE: RNA
<213> ORGANISM: Homo sapiens

<400> SEQUENCE: 41
uguaaacauc cuacacucag cu                                              22

<210> SEQ ID NO 42
<211> LENGTH: 23
<212> TYPE: RNA
<213> ORGANISM: Homo sapiens

<400> SEQUENCE: 42
aaugacacga ucacucccgu uga                                             23

<210> SEQ ID NO 43
<211> LENGTH: 22
<212> TYPE: RNA
<213> ORGANISM: Homo sapiens

<400> SEQUENCE: 43
uucaaguaau ccaggauagg cu                                              22

<210> SEQ ID NO 44
<211> LENGTH: 21
```

```
<212> TYPE: RNA
<213> ORGANISM: Homo sapiens

<400> SEQUENCE: 44
uaccacaggg uagaaccacg g                                            21

<210> SEQ ID NO 45
<211> LENGTH: 22
<212> TYPE: RNA
<213> ORGANISM: Homo sapiens

<400> SEQUENCE: 45
cagugcaaug uuaaaagggc au                                           22

<210> SEQ ID NO 46
<211> LENGTH: 22
<212> TYPE: RNA
<213> ORGANISM: Homo sapiens

<400> SEQUENCE: 46
uguaaacauc cuugacugga ag                                           22

<210> SEQ ID NO 47
<211> LENGTH: 19
<212> TYPE: RNA
<213> ORGANISM: Homo sapiens

<400> SEQUENCE: 47
aaaagcuggg uugagagga                                               19

<210> SEQ ID NO 48
<211> LENGTH: 22
<212> TYPE: RNA
<213> ORGANISM: Homo sapiens

<400> SEQUENCE: 48
aaaagcuggg uugagagggc aa                                           22

<210> SEQ ID NO 49
<211> LENGTH: 23
<212> TYPE: RNA
<213> ORGANISM: Homo sapiens

<400> SEQUENCE: 49
uuuggcacua gcacauuuuu gcu                                          23

<210> SEQ ID NO 50
<211> LENGTH: 23
<212> TYPE: RNA
<213> ORGANISM: Homo sapiens

<400> SEQUENCE: 50
ggaugguugg gggcggucgg cgu                                          23

<210> SEQ ID NO 51
<211> LENGTH: 18
<212> TYPE: RNA
<213> ORGANISM: Homo sapiens

<400> SEQUENCE: 51
aaagcugggu ugagaagg                                                18

<210> SEQ ID NO 52
```

```
<211> LENGTH: 21
<212> TYPE: RNA
<213> ORGANISM: Homo sapiens

<400> SEQUENCE: 52
ucgaggagcu cacagucuag u                                              21

<210> SEQ ID NO 53
<211> LENGTH: 20
<212> TYPE: RNA
<213> ORGANISM: Homo sapiens

<400> SEQUENCE: 53
aaaagcuggg uugagagggu                                                20

<210> SEQ ID NO 54
<211> LENGTH: 23
<212> TYPE: RNA
<213> ORGANISM: Homo sapiens

<400> SEQUENCE: 54
uagcaccauu ugaaaucagu guu                                            23

<210> SEQ ID NO 55
<211> LENGTH: 23
<212> TYPE: RNA
<213> ORGANISM: Homo sapiens

<400> SEQUENCE: 55
uaaggugcau cuagugcaga uag                                            23

<210> SEQ ID NO 56
<211> LENGTH: 23
<212> TYPE: RNA
<213> ORGANISM: Homo sapiens

<400> SEQUENCE: 56
uagugcaaua uugcuuauag ggu                                            23

<210> SEQ ID NO 57
<211> LENGTH: 22
<212> TYPE: RNA
<213> ORGANISM: Homo sapiens

<400> SEQUENCE: 57
auauaauaca accugcuaag ug                                             22

<210> SEQ ID NO 58
<211> LENGTH: 19
<212> TYPE: RNA
<213> ORGANISM: Homo sapiens

<400> SEQUENCE: 58
uugaucucgg aagcuaagc                                                 19

<210> SEQ ID NO 59
<211> LENGTH: 22
<212> TYPE: RNA
<213> ORGANISM: Homo sapiens

<400> SEQUENCE: 59
uguaacagca acuccaugug ga                                             22
```

```
<210> SEQ ID NO 60
<211> LENGTH: 23
<212> TYPE: RNA
<213> ORGANISM: Homo sapiens

<400> SEQUENCE: 60
cagugcaaua guauugucaa agc                                             23

<210> SEQ ID NO 61
<211> LENGTH: 22
<212> TYPE: RNA
<213> ORGANISM: Homo sapiens

<400> SEQUENCE: 61
aaaagcuggg uugagagggc ga                                              22

<210> SEQ ID NO 62
<211> LENGTH: 21
<212> TYPE: RNA
<213> ORGANISM: Homo sapiens

<400> SEQUENCE: 62
cugaccuaug aauugacagc c                                               21

<210> SEQ ID NO 63
<211> LENGTH: 17
<212> TYPE: RNA
<213> ORGANISM: Homo sapiens

<400> SEQUENCE: 63
gggagaaggg ucggggc                                                    17

<210> SEQ ID NO 64
<211> LENGTH: 21
<212> TYPE: RNA
<213> ORGANISM: Homo sapiens

<400> SEQUENCE: 64
gccccugggc cuauccuaga a                                               21

<210> SEQ ID NO 65
<211> LENGTH: 22
<212> TYPE: RNA
<213> ORGANISM: Homo sapiens

<400> SEQUENCE: 65
uacccauugc auaucggagu ug                                              22

<210> SEQ ID NO 66
<211> LENGTH: 22
<212> TYPE: RNA
<213> ORGANISM: Homo sapiens

<400> SEQUENCE: 66
ucucccaacc cuuguaccag ug                                              22

<210> SEQ ID NO 67
<211> LENGTH: 22
<212> TYPE: RNA
<213> ORGANISM: Homo sapiens

<400> SEQUENCE: 67
uggcucaguu cagcaggaac ag                                              22
```

```
<210> SEQ ID NO 68
<211> LENGTH: 21
<212> TYPE: RNA
<213> ORGANISM: Homo sapiens

<400> SEQUENCE: 68
aucacauugc cagggauuuc c                                              21

<210> SEQ ID NO 69
<211> LENGTH: 23
<212> TYPE: RNA
<213> ORGANISM: Homo sapiens

<400> SEQUENCE: 69
uaaggugcau cuagugcagu uag                                            23

<210> SEQ ID NO 70
<211> LENGTH: 22
<212> TYPE: RNA
<213> ORGANISM: Homo sapiens

<400> SEQUENCE: 70
uagcaccauc ugaaaucggu ua                                             22

<210> SEQ ID NO 71
<211> LENGTH: 23
<212> TYPE: RNA
<213> ORGANISM: Homo sapiens

<400> SEQUENCE: 71
uguaaacauc cuacacucuc agc                                            23

<210> SEQ ID NO 72
<211> LENGTH: 22
<212> TYPE: RNA
<213> ORGANISM: Homo sapiens

<400> SEQUENCE: 72
uauggcacug guagaauuca cu                                             22

<210> SEQ ID NO 73
<211> LENGTH: 20
<212> TYPE: RNA
<213> ORGANISM: Homo sapiens

<400> SEQUENCE: 73
ggcggcggcg gaggcggggg                                                20

<210> SEQ ID NO 74
<211> LENGTH: 22
<212> TYPE: RNA
<213> ORGANISM: Homo sapiens

<400> SEQUENCE: 74
gagcuuauuc auaaaagugc ag                                             22

<210> SEQ ID NO 75
<211> LENGTH: 21
<212> TYPE: RNA
<213> ORGANISM: Homo sapiens

<400> SEQUENCE: 75
uucacagugg cuaaguuccg c                                              21
```

<210> SEQ ID NO 76
<211> LENGTH: 20
<212> TYPE: RNA
<213> ORGANISM: Homo sapiens

<400> SEQUENCE: 76
acugccccag gugcugcugg                                               20

<210> SEQ ID NO 77
<211> LENGTH: 22
<212> TYPE: RNA
<213> ORGANISM: Homo sapiens

<400> SEQUENCE: 77
uguaaacauc cccgacugga ag                                            22

<210> SEQ ID NO 78
<211> LENGTH: 24
<212> TYPE: RNA
<213> ORGANISM: Homo sapiens

<400> SEQUENCE: 78
ggaggccggg gugggcggg gcgg                                           24

<210> SEQ ID NO 79
<211> LENGTH: 22
<212> TYPE: RNA
<213> ORGANISM: Homo sapiens

<400> SEQUENCE: 79
caaagaauuc uccuuuuggg cu                                            22

<210> SEQ ID NO 80
<211> LENGTH: 23
<212> TYPE: RNA
<213> ORGANISM: Homo sapiens

<400> SEQUENCE: 80
uggaagacua gugauuuugu ugu                                           23

<210> SEQ ID NO 81
<211> LENGTH: 18
<212> TYPE: RNA
<213> ORGANISM: Homo sapiens

<400> SEQUENCE: 81
ucgaggagcu cacagucu                                                 18

<210> SEQ ID NO 82
<211> LENGTH: 21
<212> TYPE: RNA
<213> ORGANISM: Homo sapiens

<400> SEQUENCE: 82
aauggcgcca cuaggguugu g                                             21

<210> SEQ ID NO 83
<211> LENGTH: 21
<212> TYPE: RNA
<213> ORGANISM: Homo sapiens

```
<400> SEQUENCE: 83
augaccuaug aauugacaga c                                        21

<210> SEQ ID NO 84
<211> LENGTH: 23
<212> TYPE: RNA
<213> ORGANISM: Homo sapiens

<400> SEQUENCE: 84
aacauucaac gcugucggug agu                                      23

<210> SEQ ID NO 85
<211> LENGTH: 22
<212> TYPE: RNA
<213> ORGANISM: Homo sapiens

<400> SEQUENCE: 85
cagcagcaau ucauguuuug aa                                       22

<210> SEQ ID NO 86
<211> LENGTH: 18
<212> TYPE: RNA
<213> ORGANISM: Homo sapiens

<400> SEQUENCE: 86
aggcugggcu gggacgga                                            18

<210> SEQ ID NO 87
<211> LENGTH: 22
<212> TYPE: RNA
<213> ORGANISM: Homo sapiens

<400> SEQUENCE: 87
ucagugcacu acagaacuuu gu                                       22

<210> SEQ ID NO 88
<211> LENGTH: 21
<212> TYPE: RNA
<213> ORGANISM: Homo sapiens

<400> SEQUENCE: 88
accacugcac uccagccuga g                                        21

<210> SEQ ID NO 89
<211> LENGTH: 19
<212> TYPE: RNA
<213> ORGANISM: Homo sapiens

<400> SEQUENCE: 89
ggggagcgag gggcggggc                                           19

<210> SEQ ID NO 90
<211> LENGTH: 22
<212> TYPE: RNA
<213> ORGANISM: Homo sapiens

<400> SEQUENCE: 90
acugcaguga aggcacuugu ag                                       22

<210> SEQ ID NO 91
<211> LENGTH: 18
<212> TYPE: RNA
```

```
<213> ORGANISM: Homo sapiens

<400> SEQUENCE: 91
aucccaccuc ugccacca                                                    18

<210> SEQ ID NO 92
<211> LENGTH: 22
<212> TYPE: RNA
<213> ORGANISM: Homo sapiens

<400> SEQUENCE: 92
ugagguagua aguuguauug uu                                               22

<210> SEQ ID NO 93
<211> LENGTH: 22
<212> TYPE: RNA
<213> ORGANISM: Homo sapiens

<400> SEQUENCE: 93
cagugcaaug augaaagggc au                                               22

<210> SEQ ID NO 94
<211> LENGTH: 17
<212> TYPE: RNA
<213> ORGANISM: Homo sapiens

<400> SEQUENCE: 94
accccacucc ugguacc                                                     17

<210> SEQ ID NO 95
<211> LENGTH: 22
<212> TYPE: RNA
<213> ORGANISM: Homo sapiens

<400> SEQUENCE: 95 cuggggugg ggggcugggc gu                                                22

<210> SEQ ID NO 96
<211> LENGTH: 22
<212> TYPE: RNA
<213> ORGANISM: Homo sapiens

<400> SEQUENCE: 96
cagugguuuu acccuauggu ag                                               22

<210> SEQ ID NO 97
<211> LENGTH: 22
<212> TYPE: RNA
<213> ORGANISM: Homo sapiens

<400> SEQUENCE: 97
ucagugcauc acagaacuuu gu                                               22

<210> SEQ ID NO 98
<211> LENGTH: 21
<212> TYPE: RNA
<213> ORGANISM: Homo sapiens

<400> SEQUENCE: 98
uagcagcaca gaaauauugg c                                                21

<210> SEQ ID NO 99
<211> LENGTH: 22
```

```
<212> TYPE: RNA
<213> ORGANISM: Homo sapiens

<400> SEQUENCE: 99
cugugcgugu gacagcggcu ga                                    22

<210> SEQ ID NO 100
<211> LENGTH: 23
<212> TYPE: RNA
<213> ORGANISM: Homo sapiens

<400> SEQUENCE: 100
ugaggggcag agagcgagac uuu                                   23

<210> SEQ ID NO 101
<211> LENGTH: 20
<212> TYPE: RNA
<213> ORGANISM: Homo sapiens

<400> SEQUENCE: 101 cugguuggg cugggcuggg                                        20

<210> SEQ ID NO 102
<211> LENGTH: 22
<212> TYPE: RNA
<213> ORGANISM: Homo sapiens

<400> SEQUENCE: 102
uauugcacau uacuaaguug ca                                    22

<210> SEQ ID NO 103
<211> LENGTH: 22
<212> TYPE: RNA
<213> ORGANISM: Homo sapiens

<400> SEQUENCE: 103
caugccuuga guguaggacc gu                                    22

<210> SEQ ID NO 104
<211> LENGTH: 22
<212> TYPE: RNA
<213> ORGANISM: Homo sapiens

<400> SEQUENCE: 104
acaguagucu gcacauuggu ua                                    22

<210> SEQ ID NO 105
<211> LENGTH: 20
<212> TYPE: RNA
<213> ORGANISM: Homo sapiens

<400> SEQUENCE: 105
gcggaaggcg gagcggcgga                                       20

<210> SEQ ID NO 106
<211> LENGTH: 22
<212> TYPE: RNA
<213> ORGANISM: Homo sapiens

<400> SEQUENCE: 106
ucaggcucag uccccucccg au                                    22

<210> SEQ ID NO 107
```

```
<211> LENGTH: 23
<212> TYPE: RNA
<213> ORGANISM: Homo sapiens

<400> SEQUENCE: 107
ucucacacag aaaucgcacc cgu                                              23

<210> SEQ ID NO 108
<211> LENGTH: 24
<212> TYPE: RNA
<213> ORGANISM: Homo sapiens

<400> SEQUENCE: 108
aauccuugga accuaggugu gagu                                             24

<210> SEQ ID NO 109
<211> LENGTH: 22
<212> TYPE: RNA
<213> ORGANISM: Homo sapiens

<400> SEQUENCE: 109
ugucuuacuc ccucaggcac au                                               22

<210> SEQ ID NO 110
<211> LENGTH: 22
<212> TYPE: RNA
<213> ORGANISM: Homo sapiens

<400> SEQUENCE: 110
gugaguagug gcgcgcggcg gc                                               22

<210> SEQ ID NO 111
<211> LENGTH: 21
<212> TYPE: RNA
<213> ORGANISM: Homo sapiens

<400> SEQUENCE: 111
ugagggaccc aggacaggag a                                                21

<210> SEQ ID NO 112
<211> LENGTH: 21
<212> TYPE: RNA
<213> ORGANISM: Homo sapiens

<400> SEQUENCE: 112
uucacagugg cuaaguucug c                                                21

<210> SEQ ID NO 113
<211> LENGTH: 20
<212> TYPE: RNA
<213> ORGANISM: Homo sapiens

<400> SEQUENCE: 113
uugggcuggg cuggguuggg                                                  20

<210> SEQ ID NO 114
<211> LENGTH: 21
<212> TYPE: RNA
<213> ORGANISM: Homo sapiens

<400> SEQUENCE: 114
cauuauuacu uuuggguacgc g                                               21
```

```
<210> SEQ ID NO 115
<211> LENGTH: 17
<212> TYPE: RNA
<213> ORGANISM: Homo sapiens

<400> SEQUENCE: 115
uuggaggcgu ggguuuu                                              17

<210> SEQ ID NO 116
<211> LENGTH: 21
<212> TYPE: RNA
<213> ORGANISM: Homo sapiens

<400> SEQUENCE: 116
cuagacugaa gcuccuugag g                                         21

<210> SEQ ID NO 117
<211> LENGTH: 22
<212> TYPE: RNA
<213> ORGANISM: Homo sapiens

<400> SEQUENCE: 117
ugagaacuga auuccauagg cu                                        22

<210> SEQ ID NO 118
<211> LENGTH: 23
<212> TYPE: RNA
<213> ORGANISM: Homo sapiens

<400> SEQUENCE: 118
cgcauccccu agggcauugg ugu                                       23

<210> SEQ ID NO 119
<211> LENGTH: 23
<212> TYPE: RNA
<213> ORGANISM: Homo sapiens

<400> SEQUENCE: 119
gugcguggug gcucgaggcg ggg                                       23

<210> SEQ ID NO 120
<211> LENGTH: 21
<212> TYPE: RNA
<213> ORGANISM: Homo sapiens

<400> SEQUENCE: 120
ucacagugaa ccggucucuu u                                         21

<210> SEQ ID NO 121
<211> LENGTH: 22
<212> TYPE: RNA
<213> ORGANISM: Homo sapiens

<400> SEQUENCE: 121
augcaccugg gcaaggauuc ug                                        22

<210> SEQ ID NO 122
<211> LENGTH: 18
<212> TYPE: RNA
<213> ORGANISM: Homo sapiens

<400> SEQUENCE: 122
gggucccggg gaggggggg                                            18
```

```
<210> SEQ ID NO 123
<211> LENGTH: 19
<212> TYPE: RNA
<213> ORGANISM: Homo sapiens

<400> SEQUENCE: 123
ugagggagug ggugggagg                                              19

<210> SEQ ID NO 124
<211> LENGTH: 22
<212> TYPE: RNA
<213> ORGANISM: Homo sapiens

<400> SEQUENCE: 124
aacacaccua uucaaggauu ca                                          22

<210> SEQ ID NO 125
<211> LENGTH: 22
<212> TYPE: RNA
<213> ORGANISM: Homo sapiens

<400> SEQUENCE: 125
uuauaaagca augagacuga uu                                          22

<210> SEQ ID NO 126
<211> LENGTH: 21
<212> TYPE: RNA
<213> ORGANISM: Homo sapiens

<400> SEQUENCE: 126
acuggacuag gagucagaag g                                           21

<210> SEQ ID NO 127
<211> LENGTH: 20
<212> TYPE: RNA
<213> ORGANISM: Homo sapiens

<400> SEQUENCE: 127
agugccugag ggaguaagag                                             20

<210> SEQ ID NO 128
<211> LENGTH: 22
<212> TYPE: RNA
<213> ORGANISM: Homo sapiens

<400> SEQUENCE: 128
ugagaacuga auuccauggg uu                                          22

<210> SEQ ID NO 129
<211> LENGTH: 18
<212> TYPE: RNA
<213> ORGANISM: Homo sapiens

<400> SEQUENCE: 129
agcaggugcg gggcggcg                                               18

<210> SEQ ID NO 130
<211> LENGTH: 22
<212> TYPE: RNA
<213> ORGANISM: Homo sapiens

<400> SEQUENCE: 130
ccucccacac ccaaggcuug ca                                          22
```

```
<210> SEQ ID NO 131
<211> LENGTH: 21
<212> TYPE: RNA
<213> ORGANISM: Homo sapiens

<400> SEQUENCE: 131
uggcuguugg aggggggcagg c                                            21

<210> SEQ ID NO 132
<211> LENGTH: 18
<212> TYPE: RNA
<213> ORGANISM: Homo sapiens

<400> SEQUENCE: 132
ugaggcgggg gggcgagc                                                 18

<210> SEQ ID NO 133
<211> LENGTH: 22
<212> TYPE: RNA
<213> ORGANISM: Homo sapiens

<400> SEQUENCE: 133
aaugcaccug ggcaaggauu ca                                            22

<210> SEQ ID NO 134
<211> LENGTH: 17
<212> TYPE: RNA
<213> ORGANISM: Homo sapiens

<400> SEQUENCE: 134
ggcgggugcg gggugg                                                   17

<210> SEQ ID NO 135
<211> LENGTH: 24
<212> TYPE: RNA
<213> ORGANISM: Homo sapiens

<400> SEQUENCE: 135
uuuggcaaug guagaacuca cacu                                          24

<210> SEQ ID NO 136
<211> LENGTH: 22
<212> TYPE: RNA
<213> ORGANISM: Homo sapiens

<400> SEQUENCE: 136
ccaauauuac ugugcugcuu ua                                            22

<210> SEQ ID NO 137
<211> LENGTH: 22
<212> TYPE: RNA
<213> ORGANISM: Homo sapiens

<400> SEQUENCE: 137
acugcauuau gagcacuuaa ag                                            22

<210> SEQ ID NO 138
<211> LENGTH: 23
<212> TYPE: RNA
<213> ORGANISM: Homo sapiens
```

```
<400> SEQUENCE: 138
cugggcccgc ggcgggcgug ggg                                          23

<210> SEQ ID NO 139
<211> LENGTH: 19
<212> TYPE: RNA
<213> ORGANISM: Homo sapiens

<400> SEQUENCE: 139
aucccaccac ugccaccau                                               19

<210> SEQ ID NO 140
<211> LENGTH: 21
<212> TYPE: RNA
<213> ORGANISM: Homo sapiens

<400> SEQUENCE: 140
aucacauugc cagggauuac c                                            21

<210> SEQ ID NO 141
<211> LENGTH: 20
<212> TYPE: RNA
<213> ORGANISM: Homo sapiens

<400> SEQUENCE: 141
agagaugaag cgggggggcg                                              20

<210> SEQ ID NO 142
<211> LENGTH: 18
<212> TYPE: RNA
<213> ORGANISM: Homo sapiens

<400> SEQUENCE: 142
gggugcgggc cggcgggg                                                18

<210> SEQ ID NO 143
<211> LENGTH: 18
<212> TYPE: RNA
<213> ORGANISM: Homo sapiens

<400> SEQUENCE: 143
gggcucacau caccccau                                                18

<210> SEQ ID NO 144
<211> LENGTH: 21
<212> TYPE: RNA
<213> ORGANISM: Homo sapiens

<400> SEQUENCE: 144
guaggugaca gucaggggcg g                                            21

<210> SEQ ID NO 145
<211> LENGTH: 19
<212> TYPE: RNA
<213> ORGANISM: Homo sapiens

<400> SEQUENCE: 145
cggggucggc ggcgacgug                                               19

<210> SEQ ID NO 146
<211> LENGTH: 23
<212> TYPE: RNA
```

<213> ORGANISM: Homo sapiens

<400> SEQUENCE: 146
cucggggcag gcggcuggga gcg                                          23

<210> SEQ ID NO 147
<211> LENGTH: 19
<212> TYPE: RNA
<213> ORGANISM: Homo sapiens

<400> SEQUENCE: 147
ggggccuggc ggugggcgg                                               19

<210> SEQ ID NO 148
<211> LENGTH: 22
<212> TYPE: RNA
<213> ORGANISM: Homo sapiens

<400> SEQUENCE: 148
acuggacuug gagucagaag gc                                           22

<210> SEQ ID NO 149
<211> LENGTH: 21
<212> TYPE: RNA
<213> ORGANISM: Homo sapiens

<400> SEQUENCE: 149
agcuacaucu ggcuacuggg u                                            21

<210> SEQ ID NO 150
<211> LENGTH: 22
<212> TYPE: RNA
<213> ORGANISM: Homo sapiens

<400> SEQUENCE: 150
uaguaccagu accuuguguu ca                                           22

<210> SEQ ID NO 151
<211> LENGTH: 22
<212> TYPE: RNA
<213> ORGANISM: Homo sapiens

<400> SEQUENCE: 151
uuaugguuug ccugggacug ag                                           22

<210> SEQ ID NO 152
<211> LENGTH: 22
<212> TYPE: RNA
<213> ORGANISM: Homo sapiens

<400> SEQUENCE: 152
ugaccgauuu cuccuggugu uc                                           22

<210> SEQ ID NO 153
<211> LENGTH: 22
<212> TYPE: RNA
<213> ORGANISM: Homo sapiens

<400> SEQUENCE: 153
ccaggaggcg gaggaggugg ag                                           22

<210> SEQ ID NO 154
<211> LENGTH: 23

```
<212> TYPE: RNA
<213> ORGANISM: Homo sapiens

<400> SEQUENCE: 154
agcuacauug ucugcugggu uuc                                    23

<210> SEQ ID NO 155
<211> LENGTH: 22
<212> TYPE: RNA
<213> ORGANISM: Homo sapiens

<400> SEQUENCE: 155
uccagcauca gugauuuugu ug                                     22

<210> SEQ ID NO 156
<211> LENGTH: 20
<212> TYPE: RNA
<213> ORGANISM: Homo sapiens

<400> SEQUENCE: 156
ccccagggcg acgcggcggg                                        20

<210> SEQ ID NO 157
<211> LENGTH: 17
<212> TYPE: RNA
<213> ORGANISM: Homo sapiens

<400> SEQUENCE: 157
cacugugggu acaugcu                                           17

<210> SEQ ID NO 158
<211> LENGTH: 22
<212> TYPE: RNA
<213> ORGANISM: Homo sapiens

<400> SEQUENCE: 158
ucgggccugg gguuggggga gc                                     22

<210> SEQ ID NO 159
<211> LENGTH: 21
<212> TYPE: RNA
<213> ORGANISM: Homo sapiens

<400> SEQUENCE: 159
uggguuuacg uugggagaac u                                      21

<210> SEQ ID NO 160
<211> LENGTH: 23
<212> TYPE: RNA
<213> ORGANISM: Homo sapiens

<400> SEQUENCE: 160
cccaguguuc agacuaccug uuc                                    23

<210> SEQ ID NO 161
<211> LENGTH: 21
<212> TYPE: RNA
<213> ORGANISM: Homo sapiens

<400> SEQUENCE: 161
auccuugcua ucugggugcu a                                      21

<210> SEQ ID NO 162
```

```
<211> LENGTH: 19
<212> TYPE: RNA
<213> ORGANISM: Homo sapiens

<400> SEQUENCE: 162
aaggggcugg gggagcaca                                                  19

<210> SEQ ID NO 163
<211> LENGTH: 22
<212> TYPE: RNA
<213> ORGANISM: Homo sapiens

<400> SEQUENCE: 163
ugauauguuu gauauauuag gu                                              22

<210> SEQ ID NO 164
<211> LENGTH: 20
<212> TYPE: RNA
<213> ORGANISM: Homo sapiens

<400> SEQUENCE: 164 caggggacu gggggugagc                                                  20

<210> SEQ ID NO 165
<211> LENGTH: 23
<212> TYPE: RNA
<213> ORGANISM: Homo sapiens

<400> SEQUENCE: 165 uccccaggu gugauucuga uuu                                              23

<210> SEQ ID NO 166
<211> LENGTH: 21
<212> TYPE: RNA
<213> ORGANISM: Homo sapiens

<400> SEQUENCE: 166 aggggggaaag uucuauaguc c                                              21

<210> SEQ ID NO 167
<211> LENGTH: 22
<212> TYPE: RNA
<213> ORGANISM: Homo sapiens

<400> SEQUENCE: 167
cgaaucauua uuugcugcuc ua                                              22

<210> SEQ ID NO 168
<211> LENGTH: 22
<212> TYPE: RNA
<213> ORGANISM: Homo sapiens

<400> SEQUENCE: 168
auaauacaac cugcuaagug cu                                              22

<210> SEQ ID NO 169
<211> LENGTH: 24
<212> TYPE: RNA
<213> ORGANISM: Homo sapiens

<400> SEQUENCE: 169
aggcaggggc uggugcuggg cggg                                            24
```

-continued

<210> SEQ ID NO 170
<211> LENGTH: 22
<212> TYPE: RNA
<213> ORGANISM: Homo sapiens

<400> SEQUENCE: 170
uuaucagaau cuccaggggu ac                                            22

<210> SEQ ID NO 171
<211> LENGTH: 18
<212> TYPE: RNA
<213> ORGANISM: Homo sapiens

<400> SEQUENCE: 171
cccagcagga cgggagcg                                                 18

<210> SEQ ID NO 172
<211> LENGTH: 22
<212> TYPE: RNA
<213> ORGANISM: Homo sapiens

<400> SEQUENCE: 172
ugagguagga gguuguauag uu                                            22

<210> SEQ ID NO 173
<211> LENGTH: 21
<212> TYPE: RNA
<213> ORGANISM: Homo sapiens

<400> SEQUENCE: 173
cugggagggg cuggguuugg c                                             21

<210> SEQ ID NO 174
<211> LENGTH: 25
<212> TYPE: RNA
<213> ORGANISM: Homo sapiens

<400> SEQUENCE: 174
agggaucgcg ggcgguggc ggccu                                          25

<210> SEQ ID NO 175
<211> LENGTH: 22
<212> TYPE: RNA
<213> ORGANISM: Homo sapiens

<400> SEQUENCE: 175
uagguaguuu ccuguugu ug gg                                           22

<210> SEQ ID NO 176
<211> LENGTH: 24
<212> TYPE: RNA
<213> ORGANISM: Homo sapiens

<400> SEQUENCE: 176
agggcuggac ucagcggcgg agcu                                          24

<210> SEQ ID NO 177
<211> LENGTH: 20
<212> TYPE: RNA
<213> ORGANISM: Homo sapiens

<400> SEQUENCE: 177
gcggagagag aauggggagc                                               20

```
<210> SEQ ID NO 178
<211> LENGTH: 22
<212> TYPE: RNA
<213> ORGANISM: Homo sapiens

<400> SEQUENCE: 178
gggagccagg aaguauugau gu                                              22

<210> SEQ ID NO 179
<211> LENGTH: 21
<212> TYPE: RNA
<213> ORGANISM: Homo sapiens

<400> SEQUENCE: 179
gugccagcug caguggggga g                                               21

<210> SEQ ID NO 180
<211> LENGTH: 22
<212> TYPE: RNA
<213> ORGANISM: Homo sapiens

<400> SEQUENCE: 180
cuuucagucg gauguuuaca gc                                              22

<210> SEQ ID NO 181
<211> LENGTH: 21
<212> TYPE: RNA
<213> ORGANISM: Homo sapiens

<400> SEQUENCE: 181
uggcagggag gcugggaggg g                                               21

<210> SEQ ID NO 182
<211> LENGTH: 22
<212> TYPE: RNA
<213> ORGANISM: Homo sapiens

<400> SEQUENCE: 182
cagggcaggg aaggugggag ag                                              22

<210> SEQ ID NO 183
<211> LENGTH: 22
<212> TYPE: RNA
<213> ORGANISM: Homo sapiens

<400> SEQUENCE: 183
aaggagcuca cagucuauug ag                                              22

<210> SEQ ID NO 184
<211> LENGTH: 22
<212> TYPE: RNA
<213> ORGANISM: Homo sapiens

<400> SEQUENCE: 184
caacaaauca cagucugcca ua                                              22

<210> SEQ ID NO 185
<211> LENGTH: 22
<212> TYPE: RNA
<213> ORGANISM: Homo sapiens

<400> SEQUENCE: 185
uucaccaccu ucuccaccca gc                                              22
```

```
<210> SEQ ID NO 186
<211> LENGTH: 23
<212> TYPE: RNA
<213> ORGANISM: Homo sapiens

<400> SEQUENCE: 186 agggugggggc uggaggtuggg gcu                                              23

<210> SEQ ID NO 187
<211> LENGTH: 21
<212> TYPE: RNA
<213> ORGANISM: Homo sapiens

<400> SEQUENCE: 187
ugauugucca aacgcaauuc u                                                  21

<210> SEQ ID NO 188
<211> LENGTH: 23
<212> TYPE: RNA
<213> ORGANISM: Homo sapiens

<400> SEQUENCE: 188
uuagggagua gaagggugggg gag                                               23

<210> SEQ ID NO 189
<211> LENGTH: 21
<212> TYPE: RNA
<213> ORGANISM: Homo sapiens

<400> SEQUENCE: 189
aggggugcua ucugugauug a                                                  21

<210> SEQ ID NO 190
<211> LENGTH: 22
<212> TYPE: RNA
<213> ORGANISM: Homo sapiens

<400> SEQUENCE: 190
gugagucucu aagaaaagag ga                                                 22

<210> SEQ ID NO 191
<211> LENGTH: 23
<212> TYPE: RNA
<213> ORGANISM: Homo sapiens

<400> SEQUENCE: 191
ucaagagcaa uaacgaaaaa ugu                                                23

<210> SEQ ID NO 192
<211> LENGTH: 23
<212> TYPE: RNA
<213> ORGANISM: Homo sapiens

<400> SEQUENCE: 192
aggaagcccu ggaggggcug gag                                                23

<210> SEQ ID NO 193
<211> LENGTH: 22
<212> TYPE: RNA
<213> ORGANISM: Homo sapiens
```

```
<400> SEQUENCE: 193
uuacggacca gcuaagggag gc                                          22

<210> SEQ ID NO 194
<211> LENGTH: 17
<212> TYPE: RNA
<213> ORGANISM: Homo sapiens

<400> SEQUENCE: 194
gagacugggg uggggcc                                                17

<210> SEQ ID NO 195
<211> LENGTH: 22
<212> TYPE: RNA
<213> ORGANISM: Homo sapiens

<400> SEQUENCE: 195
aauccuuugu cccuggguga ga                                          22

<210> SEQ ID NO 196
<211> LENGTH: 22
<212> TYPE: RNA
<213> ORGANISM: Homo sapiens

<400> SEQUENCE: 196 gcggggugg cggcggcauc cc                                           22

<210> SEQ ID NO 197
<211> LENGTH: 23
<212> TYPE: RNA
<213> ORGANISM: Homo sapiens

<400> SEQUENCE: 197
uggggaaggc uuggcaggga aga                                         23

<210> SEQ ID NO 198
<211> LENGTH: 20
<212> TYPE: RNA
<213> ORGANISM: Homo sapiens

<400> SEQUENCE: 198
acuggacuug gagucagaaa                                             20

<210> SEQ ID NO 199
<211> LENGTH: 22
<212> TYPE: RNA
<213> ORGANISM: Homo sapiens

<400> SEQUENCE: 199
cacgcucaug cacacaccca ca                                          22

<210> SEQ ID NO 200
<211> LENGTH: 22
<212> TYPE: RNA
<213> ORGANISM: Homo sapiens

<400> SEQUENCE: 200
ucagcaaaca uuuauugugu gc                                          22

<210> SEQ ID NO 201
<211> LENGTH: 23
<212> TYPE: RNA
```

```
<213> ORGANISM: Homo sapiens

<400> SEQUENCE: 201
uaauccuugc uaccugggug aga                                          23

<210> SEQ ID NO 202
<211> LENGTH: 22
<212> TYPE: RNA
<213> ORGANISM: Homo sapiens

<400> SEQUENCE: 202
uaacagucua cagccauggu cg                                           22

<210> SEQ ID NO 203
<211> LENGTH: 22
<212> TYPE: RNA
<213> ORGANISM: Homo sapiens

<400> SEQUENCE: 203
ugggauccag acagugggag aa                                           22

<210> SEQ ID NO 204
<211> LENGTH: 22
<212> TYPE: RNA
<213> ORGANISM: Homo sapiens

<400> SEQUENCE: 204
uacgucaucg uugucaucgu ca                                           22

<210> SEQ ID NO 205
<211> LENGTH: 22
<212> TYPE: RNA
<213> ORGANISM: Homo sapiens

<400> SEQUENCE: 205
ugcggggcua gggcuaacag ca                                           22

<210> SEQ ID NO 206
<211> LENGTH: 21
<212> TYPE: RNA
<213> ORGANISM: Homo sapiens

<400> SEQUENCE: 206
ucuguggagu ggggugccug u                                            21

<210> SEQ ID NO 207
<211> LENGTH: 23
<212> TYPE: RNA
<213> ORGANISM: Homo sapiens

<400> SEQUENCE: 207
uuaaugcuaa ucgugauagg ggu                                          23

<210> SEQ ID NO 208
<211> LENGTH: 22
<212> TYPE: RNA
<213> ORGANISM: Homo sapiens

<400> SEQUENCE: 208
aguuugggau ggagagagga ga                                           22

<210> SEQ ID NO 209
<211> LENGTH: 22
```

```
<212> TYPE: RNA
<213> ORGANISM: Homo sapiens

<400> SEQUENCE: 209
caguuaucac agugcugaug cu                                          22

<210> SEQ ID NO 210
<211> LENGTH: 25
<212> TYPE: RNA
<213> ORGANISM: Homo sapiens

<400> SEQUENCE: 210
aagggaggag gagcggaggg gcccu                                       25

<210> SEQ ID NO 211
<211> LENGTH: 19
<212> TYPE: RNA
<213> ORGANISM: Homo sapiens

<400> SEQUENCE: 211
cagcaggagg ugaggggag                                              19

<210> SEQ ID NO 212
<211> LENGTH: 22
<212> TYPE: RNA
<213> ORGANISM: Homo sapiens

<400> SEQUENCE: 212
acucaaaaga uggcggcacu uu                                          22

<210> SEQ ID NO 213
<211> LENGTH: 18
<212> TYPE: RNA
<213> ORGANISM: Homo sapiens

<400> SEQUENCE: 213
gugaaggccc ggcggaga                                               18

<210> SEQ ID NO 214
<211> LENGTH: 20
<212> TYPE: RNA
<213> ORGANISM: Homo sapiens

<400> SEQUENCE: 214
gggaaaagga aggggagga                                              20

<210> SEQ ID NO 215
<211> LENGTH: 22
<212> TYPE: RNA
<213> ORGANISM: Homo sapiens

<400> SEQUENCE: 215
aaucugagaa ggcgcacaag gu                                          22

<210> SEQ ID NO 216
<211> LENGTH: 22
<212> TYPE: RNA
<213> ORGANISM: Homo sapiens

<400> SEQUENCE: 216
guggguacgg cccagugggg gg                                          22

<210> SEQ ID NO 217
```

```
<211> LENGTH: 19
<212> TYPE: RNA
<213> ORGANISM: Homo sapiens

<400> SEQUENCE: 217
aauggauuuu uggagcagg                                            19

<210> SEQ ID NO 218
<211> LENGTH: 23
<212> TYPE: RNA
<213> ORGANISM: Homo sapiens

<400> SEQUENCE: 218
uguagagcag ggagcaggaa gcu                                       23

<210> SEQ ID NO 219
<211> LENGTH: 21
<212> TYPE: RNA
<213> ORGANISM: Homo sapiens

<400> SEQUENCE: 219
ccugcgaguc uccggcggug g                                         21

<210> SEQ ID NO 220
<211> LENGTH: 22
<212> TYPE: RNA
<213> ORGANISM: Homo sapiens

<400> SEQUENCE: 220
caggccauau ugugcugccu ca                                        22

<210> SEQ ID NO 221
<211> LENGTH: 22
<212> TYPE: RNA
<213> ORGANISM: Homo sapiens

<400> SEQUENCE: 221
ucggccuggg gaggaggaag gg                                        22

<210> SEQ ID NO 222
<211> LENGTH: 23
<212> TYPE: RNA
<213> ORGANISM: Homo sapiens

<400> SEQUENCE: 222
cggguagaga gggcaguggg agg                                       23

<210> SEQ ID NO 223
<211> LENGTH: 23
<212> TYPE: RNA
<213> ORGANISM: Homo sapiens

<400> SEQUENCE: 223
aacauucauu gcugucggug ggu                                       23

<210> SEQ ID NO 224
<211> LENGTH: 24
<212> TYPE: RNA
<213> ORGANISM: Homo sapiens

<400> SEQUENCE: 224 gugggguaggg uuugggggag agcg                                     24
```

```
<210> SEQ ID NO 225
<211> LENGTH: 23
<212> TYPE: RNA
<213> ORGANISM: Homo sapiens

<400> SEQUENCE: 225
ucaauaggaa agagguggga ccu                                              23

<210> SEQ ID NO 226
<211> LENGTH: 24
<212> TYPE: RNA
<213> ORGANISM: Homo sapiens

<400> SEQUENCE: 226 ugggagcug aggcucuggg ggug                                              24

<210> SEQ ID NO 227
<211> LENGTH: 20
<212> TYPE: RNA
<213> ORGANISM: Homo sapiens

<400> SEQUENCE: 227 gugguuggg gcgggcucug                                                   20

<210> SEQ ID NO 228
<211> LENGTH: 20
<212> TYPE: RNA
<213> ORGANISM: Homo sapiens

<400> SEQUENCE: 228
gugagucagg gugggcugg                                                   20

<210> SEQ ID NO 229
<211> LENGTH: 22
<212> TYPE: RNA
<213> ORGANISM: Homo sapiens

<400> SEQUENCE: 229
aacauucaac cugucgguga gu                                               22

<210> SEQ ID NO 230
<211> LENGTH: 21
<212> TYPE: RNA
<213> ORGANISM: Homo sapiens

<400> SEQUENCE: 230
aacauagagg aaauuccacg u                                                21

<210> SEQ ID NO 231
<211> LENGTH: 22
<212> TYPE: RNA
<213> ORGANISM: Homo sapiens

<400> SEQUENCE: 231
aggcgaugug gggauguaga ga                                               22

<210> SEQ ID NO 232
<211> LENGTH: 22
<212> TYPE: RNA
<213> ORGANISM: Homo sapiens

<400> SEQUENCE: 232
cgucaacacu ugcugguuuc cu                                               22
```

```
<210> SEQ ID NO 233
<211> LENGTH: 26
<212> TYPE: RNA
<213> ORGANISM: Homo sapiens

<400> SEQUENCE: 233
cccagggcuu ggagugggc aagguu                                         26

<210> SEQ ID NO 234
<211> LENGTH: 22
<212> TYPE: RNA
<213> ORGANISM: Homo sapiens

<400> SEQUENCE: 234
ugaaacauac acgggaaacc uc                                            22

<210> SEQ ID NO 235
<211> LENGTH: 22
<212> TYPE: RNA
<213> ORGANISM: Homo sapiens

<400> SEQUENCE: 235
aguucuucag uggcaagcuu ua                                            22

<210> SEQ ID NO 236
<211> LENGTH: 22
<212> TYPE: RNA
<213> ORGANISM: Homo sapiens

<400> SEQUENCE: 236
augugccuga gggaguaaga ca                                            22

<210> SEQ ID NO 237
<211> LENGTH: 23
<212> TYPE: RNA
<213> ORGANISM: Homo sapiens

<400> SEQUENCE: 237
uuacaguugu ucaaccaguu acu                                           23

<210> SEQ ID NO 238
<211> LENGTH: 22
<212> TYPE: RNA
<213> ORGANISM: Homo sapiens

<400> SEQUENCE: 238
uguaaacauc cucgacugga ag                                            22

<210> SEQ ID NO 239
<211> LENGTH: 19
<212> TYPE: RNA
<213> ORGANISM: Homo sapiens

<400> SEQUENCE: 239
ggcuggucag augggagug                                                19

<210> SEQ ID NO 240
<211> LENGTH: 22
<212> TYPE: RNA
<213> ORGANISM: Homo sapiens

<400> SEQUENCE: 240
uucauuugcc ucccagccua ca                                            22
```

```
<210> SEQ ID NO 241
<211> LENGTH: 22
<212> TYPE: RNA
<213> ORGANISM: Homo sapiens

<400> SEQUENCE: 241
caccuugcgc uacucagguc ug                                            22

<210> SEQ ID NO 242
<211> LENGTH: 22
<212> TYPE: RNA
<213> ORGANISM: Homo sapiens

<400> SEQUENCE: 242
aacuggccua caaaguccca gu                                            22

<210> SEQ ID NO 243
<211> LENGTH: 19
<212> TYPE: RNA
<213> ORGANISM: Homo sapiens

<400> SEQUENCE: 243
uaaggagggg gaugagggg                                                19

<210> SEQ ID NO 244
<211> LENGTH: 23
<212> TYPE: RNA
<213> ORGANISM: Homo sapiens

<400> SEQUENCE: 244
cccaguguuu agacuaucug uuc                                           23

<210> SEQ ID NO 245
<211> LENGTH: 21
<212> TYPE: RNA
<213> ORGANISM: Homo sapiens

<400> SEQUENCE: 245
caggaguggg ggugggacg u                                              21

<210> SEQ ID NO 246
<211> LENGTH: 20
<212> TYPE: RNA
<213> ORGANISM: Homo sapiens

<400> SEQUENCE: 246
gguagugagu uaucagcuac                                               20

<210> SEQ ID NO 247
<211> LENGTH: 21
<212> TYPE: RNA
<213> ORGANISM: Homo sapiens

<400> SEQUENCE: 247
ucagugcaug acagaacuug g                                             21

<210> SEQ ID NO 248
<211> LENGTH: 23
<212> TYPE: RNA
<213> ORGANISM: Homo sapiens
```

```
<400> SEQUENCE: 248
uugaggggag aaugaggugg aga                                          23

<210> SEQ ID NO 249
<211> LENGTH: 21
<212> TYPE: RNA
<213> ORGANISM: Homo sapiens

<400> SEQUENCE: 249
aucauagagg aaaauccacg u                                            21

<210> SEQ ID NO 250
<211> LENGTH: 22
<212> TYPE: RNA
<213> ORGANISM: Homo sapiens

<400> SEQUENCE: 250
acugcugagc uagcacuucc cg                                           22

<210> SEQ ID NO 251
<211> LENGTH: 18
<212> TYPE: RNA
<213> ORGANISM: Homo sapiens

<400> SEQUENCE: 251
cggggcggca ggggccuc                                                18

<210> SEQ ID NO 252
<211> LENGTH: 22
<212> TYPE: RNA
<213> ORGANISM: Homo sapiens

<400> SEQUENCE: 252
aaugcacccg ggcaaggauu cu                                           22

<210> SEQ ID NO 253
<211> LENGTH: 22
<212> TYPE: RNA
<213> ORGANISM: Homo sapiens

<400> SEQUENCE: 253
guggaguccu ggggaaugga ga                                           22

<210> SEQ ID NO 254
<211> LENGTH: 21
<212> TYPE: RNA
<213> ORGANISM: Homo sapiens

<400> SEQUENCE: 254
gcccugaccu guccuguucu g                                            21

<210> SEQ ID NO 255
<211> LENGTH: 22
<212> TYPE: RNA
<213> ORGANISM: Homo sapiens

<400> SEQUENCE: 255
auaguccgag uaacgucggg gc                                           22

<210> SEQ ID NO 256
<211> LENGTH: 22
<212> TYPE: RNA
```

```
<213> ORGANISM: Homo sapiens

<400> SEQUENCE: 256
uaaugccccu aaaaauccuu au                                          22

<210> SEQ ID NO 257
<211> LENGTH: 16
<212> TYPE: RNA
<213> ORGANISM: Homo sapiens

<400> SEQUENCE: 257
uucagcagga acagcu                                                 16

<210> SEQ ID NO 258
<211> LENGTH: 22
<212> TYPE: RNA
<213> ORGANISM: Homo sapiens

<400> SEQUENCE: 258
gugcggaacg cuggccgggg cg                                          22

<210> SEQ ID NO 259
<211> LENGTH: 24
<212> TYPE: RNA
<213> ORGANISM: Homo sapiens

<400> SEQUENCE: 259
ucccugagac ccuuuaaccu guga                                        24

<210> SEQ ID NO 260
<211> LENGTH: 18
<212> TYPE: RNA
<213> ORGANISM: Homo sapiens

<400> SEQUENCE: 260
cgggcguggu ggugggg                                                18

<210> SEQ ID NO 261
<211> LENGTH: 21
<212> TYPE: RNA
<213> ORGANISM: Homo sapiens

<400> SEQUENCE: 261
cguggaggac gaggaggagg c                                           21

<210> SEQ ID NO 262
<211> LENGTH: 22
<212> TYPE: RNA
<213> ORGANISM: Homo sapiens

<400> SEQUENCE: 262 ccccugggc ugggcaggcg ga                                           22

<210> SEQ ID NO 263
<211> LENGTH: 22
<212> TYPE: RNA
<213> ORGANISM: Homo sapiens

<400> SEQUENCE: 263
cugggacagg aggaggaggc ag                                          22

<210> SEQ ID NO 264
<211> LENGTH: 23
```

```
<212> TYPE: RNA
<213> ORGANISM: Homo sapiens

<400> SEQUENCE: 264
uauucauuua uccccagccu aca                                           23

<210> SEQ ID NO 265
<211> LENGTH: 17
<212> TYPE: RNA
<213> ORGANISM: Homo sapiens

<400> SEQUENCE: 265
cgcgccgggc ccggguu                                                  17

<210> SEQ ID NO 266
<211> LENGTH: 20
<212> TYPE: RNA
<213> ORGANISM: Homo sapiens

<400> SEQUENCE: 266
cgggcguggu ggugggggug                                               20

<210> SEQ ID NO 267
<211> LENGTH: 22
<212> TYPE: RNA
<213> ORGANISM: Homo sapiens

<400> SEQUENCE: 267
uuuucaacuc uaaugggaga ga                                            22

<210> SEQ ID NO 268
<211> LENGTH: 17
<212> TYPE: RNA
<213> ORGANISM: Homo sapiens

<400> SEQUENCE: 268
gccggacaag agggagg                                                  17

<210> SEQ ID NO 269
<211> LENGTH: 22
<212> TYPE: RNA
<213> ORGANISM: Homo sapiens

<400> SEQUENCE: 269
ucugggcaac aaagugagac cu                                            22

<210> SEQ ID NO 270
<211> LENGTH: 22
<212> TYPE: RNA
<213> ORGANISM: Homo sapiens

<400> SEQUENCE: 270
uccgucucag uuacuuuaua gc                                            22

<210> SEQ ID NO 271
<211> LENGTH: 22
<212> TYPE: RNA
<213> ORGANISM: Homo sapiens

<400> SEQUENCE: 271
gugggcuggg cugggcuggg cc                                            22

<210> SEQ ID NO 272
```

```
<211> LENGTH: 22
<212> TYPE: RNA
<213> ORGANISM: Homo sapiens

<400> SEQUENCE: 272
agacacauuu ggagagggaa cc                                               22

<210> SEQ ID NO 273
<211> LENGTH: 22
<212> TYPE: RNA
<213> ORGANISM: Homo sapiens

<400> SEQUENCE: 273
ggcuggagcg agugcagugg ug                                               22

<210> SEQ ID NO 274
<211> LENGTH: 21
<212> TYPE: RNA
<213> ORGANISM: Homo sapiens

<400> SEQUENCE: 274
guguggccgg caggcgggug g                                                21

<210> SEQ ID NO 275
<211> LENGTH: 19
<212> TYPE: RNA
<213> ORGANISM: Homo sapiens

<400> SEQUENCE: 275
gagggcgggu ggaggagga                                                   19

<210> SEQ ID NO 276
<211> LENGTH: 22
<212> TYPE: RNA
<213> ORGANISM: Homo sapiens

<400> SEQUENCE: 276
cguguauuug acaagcugag uu                                               22

<210> SEQ ID NO 277
<211> LENGTH: 20
<212> TYPE: RNA
<213> ORGANISM: Homo sapiens

<400> SEQUENCE: 277
acugggcuug gagucagaag                                                  20

<210> SEQ ID NO 278
<211> LENGTH: 23
<212> TYPE: RNA
<213> ORGANISM: Homo sapiens

<400> SEQUENCE: 278
guccaguuuu cccaggaauc ccu                                              23

<210> SEQ ID NO 279
<211> LENGTH: 22
<212> TYPE: RNA
<213> ORGANISM: Homo sapiens

<400> SEQUENCE: 279
ucaaaaucag gagucggggc uu                                               22
```

```
<210> SEQ ID NO 280
<211> LENGTH: 20
<212> TYPE: RNA
<213> ORGANISM: Homo sapiens

<400> SEQUENCE: 280
gggcuggggc gcgggaggu                                            20

<210> SEQ ID NO 281
<211> LENGTH: 18
<212> TYPE: RNA
<213> ORGANISM: Homo sapiens

<400> SEQUENCE: 281
gcuggugaca ugagaggc                                             18

<210> SEQ ID NO 282
<211> LENGTH: 23
<212> TYPE: RNA
<213> ORGANISM: Homo sapiens

<400> SEQUENCE: 282
ugaggauaug gcagggaagg gga                                       23

<210> SEQ ID NO 283
<211> LENGTH: 23
<212> TYPE: RNA
<213> ORGANISM: Homo sapiens

<400> SEQUENCE: 283
ucggggauca ucaugucacg aga                                       23

<210> SEQ ID NO 284
<211> LENGTH: 22
<212> TYPE: RNA
<213> ORGANISM: Homo sapiens

<400> SEQUENCE: 284
gagcaggcga ggcugggcug aa                                        22

<210> SEQ ID NO 285
<211> LENGTH: 21
<212> TYPE: RNA
<213> ORGANISM: Homo sapiens

<400> SEQUENCE: 285
caacaccagu cgaugggcug u                                         21

<210> SEQ ID NO 286
<211> LENGTH: 22
<212> TYPE: RNA
<213> ORGANISM: Homo sapiens

<400> SEQUENCE: 286 ggagggucc cgcacuggga gg                                         22

<210> SEQ ID NO 287
<211> LENGTH: 20
<212> TYPE: RNA
<213> ORGANISM: Homo sapiens

<400> SEQUENCE: 287
ucagggaguc aggggagggc                                           20
```

```
<210> SEQ ID NO 288
<211> LENGTH: 19
<212> TYPE: RNA
<213> ORGANISM: Homo sapiens

<400> SEQUENCE: 288 cugggagug gcugggag                                                      19

<210> SEQ ID NO 289
<211> LENGTH: 22
<212> TYPE: RNA
<213> ORGANISM: Homo sapiens

<400> SEQUENCE: 289
ugugacagau ugauaacuga aa                                                22

<210> SEQ ID NO 290
<211> LENGTH: 24
<212> TYPE: RNA
<213> ORGANISM: Homo sapiens

<400> SEQUENCE: 290
uagguagagu gugaggagga gguc                                              24

<210> SEQ ID NO 291
<211> LENGTH: 22
<212> TYPE: RNA
<213> ORGANISM: Homo sapiens

<400> SEQUENCE: 291
cggaugagca aagaaagugg uu                                                22

<210> SEQ ID NO 292
<211> LENGTH: 22
<212> TYPE: RNA
<213> ORGANISM: Homo sapiens

<400> SEQUENCE: 292
cuccugacuc cagguccugu gu                                                22

<210> SEQ ID NO 293
<211> LENGTH: 19
<212> TYPE: RNA
<213> ORGANISM: Homo sapiens

<400> SEQUENCE: 293
ugcggcagag cuggggguca                                                   19

<210> SEQ ID NO 294
<211> LENGTH: 17
<212> TYPE: RNA
<213> ORGANISM: Homo sapiens

<400> SEQUENCE: 294
gcugggcgag gcuggca                                                      17

<210> SEQ ID NO 295
<211> LENGTH: 20
<212> TYPE: RNA
<213> ORGANISM: Homo sapiens

<400> SEQUENCE: 295
ggggaggugu gcagggcugg                                                   20
```

```
<210> SEQ ID NO 296
<211> LENGTH: 22
<212> TYPE: RNA
<213> ORGANISM: Homo sapiens

<400> SEQUENCE: 296
augcugacau auuuacuaga gg                                              22

<210> SEQ ID NO 297
<211> LENGTH: 22
<212> TYPE: RNA
<213> ORGANISM: Homo sapiens

<400> SEQUENCE: 297
cuauacgacc ugcugccuuu cu                                              22

<210> SEQ ID NO 298
<211> LENGTH: 23
<212> TYPE: RNA
<213> ORGANISM: Homo sapiens

<400> SEQUENCE: 298
guuugcacgg gugggccuug ucu                                             23

<210> SEQ ID NO 299
<211> LENGTH: 21
<212> TYPE: RNA
<213> ORGANISM: Homo sapiens

<400> SEQUENCE: 299
caucccuugc augguggagg g                                               21

<210> SEQ ID NO 300
<211> LENGTH: 18
<212> TYPE: RNA
<213> ORGANISM: Homo sapiens

<400> SEQUENCE: 300
aauccuugcu accugggu                                                   18

<210> SEQ ID NO 301
<211> LENGTH: 23
<212> TYPE: RNA
<213> ORGANISM: Homo sapiens

<400> SEQUENCE: 301
ugagcaccac acaggccggg cgc                                             23

<210> SEQ ID NO 302
<211> LENGTH: 24
<212> TYPE: RNA
<213> ORGANISM: Homo sapiens

<400> SEQUENCE: 302
guaggggcgu cccgggcgcg cggg                                            24

<210> SEQ ID NO 303
<211> LENGTH: 22
<212> TYPE: RNA
<213> ORGANISM: Homo sapiens
```

```
<400> SEQUENCE: 303
aucacacaaa ggcaacuuuu gu                                              22

<210> SEQ ID NO 304
<211> LENGTH: 18
<212> TYPE: RNA
<213> ORGANISM: Homo sapiens

<400> SEQUENCE: 304
cggcuggagg ugugagga                                                   18

<210> SEQ ID NO 305
<211> LENGTH: 23
<212> TYPE: RNA
<213> ORGANISM: Homo sapiens

<400> SEQUENCE: 305
ucgcagacag ggacacaugg aga                                             23

<210> SEQ ID NO 306
<211> LENGTH: 21
<212> TYPE: RNA
<213> ORGANISM: Homo sapiens

<400> SEQUENCE: 306
ucgaccggac cucgaccggc u                                               21

<210> SEQ ID NO 307
<211> LENGTH: 22
<212> TYPE: RNA
<213> ORGANISM: Homo sapiens

<400> SEQUENCE: 307
agccuuccag gagaaaugga ga                                              22

<210> SEQ ID NO 308
<211> LENGTH: 22
<212> TYPE: RNA
<213> ORGANISM: Homo sapiens

<400> SEQUENCE: 308
aacccguaga uccgaucuug ug                                              22

<210> SEQ ID NO 309
<211> LENGTH: 22
<212> TYPE: RNA
<213> ORGANISM: Homo sapiens

<400> SEQUENCE: 309 aaggggaag gaaacaugga ga                                               22

<210> SEQ ID NO 310
<211> LENGTH: 22
<212> TYPE: RNA
<213> ORGANISM: Homo sapiens

<400> SEQUENCE: 310
uggggagcgg cccccgggug gg                                              22

<210> SEQ ID NO 311
<211> LENGTH: 21
<212> TYPE: RNA
```

-continued

```
<213> ORGANISM: Homo sapiens

<400> SEQUENCE: 311
cggggcagcu caguacagga u                                      21

<210> SEQ ID NO 312
<211> LENGTH: 22
<212> TYPE: RNA
<213> ORGANISM: Homo sapiens

<400> SEQUENCE: 312
acuccagccc cacagccuca gc                                     22

<210> SEQ ID NO 313
<211> LENGTH: 22
<212> TYPE: RNA
<213> ORGANISM: Homo sapiens

<400> SEQUENCE: 313
uguguccggg aaguggagga gg                                     22

<210> SEQ ID NO 314
<211> LENGTH: 22
<212> TYPE: RNA
<213> ORGANISM: Homo sapiens

<400> SEQUENCE: 314
uaacacuguc ugguaaagau gg                                     22

<210> SEQ ID NO 315
<211> LENGTH: 22
<212> TYPE: RNA
<213> ORGANISM: Homo sapiens

<400> SEQUENCE: 315
ucccugagac ccuaacuugu ga                                     22

<210> SEQ ID NO 316
<211> LENGTH: 21
<212> TYPE: RNA
<213> ORGANISM: Homo sapiens

<400> SEQUENCE: 316
agcaugacag aggagaggug g                                      21

<210> SEQ ID NO 317
<211> LENGTH: 22
<212> TYPE: RNA
<213> ORGANISM: Homo sapiens

<400> SEQUENCE: 317
caggaggcag ugggcgagca gg                                     22

<210> SEQ ID NO 318
<211> LENGTH: 24
<212> TYPE: RNA
<213> ORGANISM: Homo sapiens

<400> SEQUENCE: 318
cauagcccgg ucgcugguac auga                                   24

<210> SEQ ID NO 319
<211> LENGTH: 22
```

```
<212> TYPE: RNA
<213> ORGANISM: Homo sapiens

<400> SEQUENCE: 319
ucuucucugu uuuggccaug ug                                    22

<210> SEQ ID NO 320
<211> LENGTH: 22
<212> TYPE: RNA
<213> ORGANISM: Homo sapiens

<400> SEQUENCE: 320 ugaggguuu ggaaugggau gg                                     22

<210> SEQ ID NO 321
<211> LENGTH: 22
<212> TYPE: RNA
<213> ORGANISM: Homo sapiens

<400> SEQUENCE: 321
uuuugcgaug uguuccuaau au                                    22

<210> SEQ ID NO 322
<211> LENGTH: 17
<212> TYPE: RNA
<213> ORGANISM: Homo sapiens

<400> SEQUENCE: 322 gugggccag gcggugg                                           17

<210> SEQ ID NO 323
<211> LENGTH: 19
<212> TYPE: RNA
<213> ORGANISM: Homo sapiens

<400> SEQUENCE: 323
gggggaagaa aaggugggg                                        19

<210> SEQ ID NO 324
<211> LENGTH: 22
<212> TYPE: RNA
<213> ORGANISM: Homo sapiens

<400> SEQUENCE: 324
uggcaguguc uuagcugguu gu                                    22

<210> SEQ ID NO 325
<211> LENGTH: 22
<212> TYPE: RNA
<213> ORGANISM: Homo sapiens

<400> SEQUENCE: 325
cugcccuggc ccgagggacc ga                                    22

<210> SEQ ID NO 326
<211> LENGTH: 23
<212> TYPE: RNA
<213> ORGANISM: Homo sapiens

<400> SEQUENCE: 326
uggaguuaag gguugcuugg aga                                   23

<210> SEQ ID NO 327
```

```
<211> LENGTH: 22
<212> TYPE: RNA
<213> ORGANISM: Homo sapiens

<400> SEQUENCE: 327
ugagaccucu ggguucugag cu                                              22

<210> SEQ ID NO 328
<211> LENGTH: 22
<212> TYPE: RNA
<213> ORGANISM: Homo sapiens

<400> SEQUENCE: 328
cuggcccucu cugcccuucc gu                                              22

<210> SEQ ID NO 329
<211> LENGTH: 22
<212> TYPE: RNA
<213> ORGANISM: Homo sapiens

<400> SEQUENCE: 329
gugaauuacc gaagggccau aa                                              22

<210> SEQ ID NO 330
<211> LENGTH: 22
<212> TYPE: RNA
<213> ORGANISM: Homo sapiens

<400> SEQUENCE: 330
cugccaauuc cauaggucac ag                                              22

<210> SEQ ID NO 331
<211> LENGTH: 25
<212> TYPE: RNA
<213> ORGANISM: Homo sapiens

<400> SEQUENCE: 331
ucggggcaug ggggagggag gcugg                                           25

<210> SEQ ID NO 332
<211> LENGTH: 22
<212> TYPE: RNA
<213> ORGANISM: Homo sapiens

<400> SEQUENCE: 332
aaucguacag ggucauccac uu                                              22

<210> SEQ ID NO 333
<211> LENGTH: 23
<212> TYPE: RNA
<213> ORGANISM: Homo sapiens

<400> SEQUENCE: 333
acuccauuug uuuugaugau gga                                             23

<210> SEQ ID NO 334
<211> LENGTH: 20
<212> TYPE: RNA
<213> ORGANISM: Homo sapiens

<400> SEQUENCE: 334
ccucugggcc cuuccuccag                                                 20
```

```
<210> SEQ ID NO 335
<211> LENGTH: 23
<212> TYPE: RNA
<213> ORGANISM: Homo sapiens

<400> SEQUENCE: 335
cgggcugucc ggaggggucg gcu                                              23

<210> SEQ ID NO 336
<211> LENGTH: 22
<212> TYPE: RNA
<213> ORGANISM: Homo sapiens

<400> SEQUENCE: 336
ugcagggguc ggugggcca gg                                                22

<210> SEQ ID NO 337
<211> LENGTH: 22
<212> TYPE: RNA
<213> ORGANISM: Homo sapiens

<400> SEQUENCE: 337
accuggcaua caauguagau uu                                               22

<210> SEQ ID NO 338
<211> LENGTH: 21
<212> TYPE: RNA
<213> ORGANISM: Homo sapiens

<400> SEQUENCE: 338 agggccccccc cucaauccug u                                               21

<210> SEQ ID NO 339
<211> LENGTH: 19
<212> TYPE: RNA
<213> ORGANISM: Homo sapiens

<400> SEQUENCE: 339
gagccaguug gacaggagc                                                   19

<210> SEQ ID NO 340
<211> LENGTH: 22
<212> TYPE: RNA
<213> ORGANISM: Homo sapiens

<400> SEQUENCE: 340
gugagccagu ggaauggaga gg                                               22

<210> SEQ ID NO 341
<211> LENGTH: 22
<212> TYPE: RNA
<213> ORGANISM: Homo sapiens

<400> SEQUENCE: 341
aaagacccau ugaggagaag gu                                               22

<210> SEQ ID NO 342
<211> LENGTH: 22
<212> TYPE: RNA
<213> ORGANISM: Homo sapiens

<400> SEQUENCE: 342
ugggagggcg uggaugaugg ug                                               22
```

```
<210> SEQ ID NO 343
<211> LENGTH: 21
<212> TYPE: RNA
<213> ORGANISM: Homo sapiens

<400> SEQUENCE: 343
ucuaguaaga guggcagucg a                                              21

<210> SEQ ID NO 344
<211> LENGTH: 23
<212> TYPE: RNA
<213> ORGANISM: Homo sapiens

<400> SEQUENCE: 344
ugagugugug ugugagug ugu                                              23

<210> SEQ ID NO 345
<211> LENGTH: 23
<212> TYPE: RNA
<213> ORGANISM: Homo sapiens

<400> SEQUENCE: 345
uaauacugcc ggguaaugau gga                                            23

<210> SEQ ID NO 346
<211> LENGTH: 21
<212> TYPE: RNA
<213> ORGANISM: Homo sapiens

<400> SEQUENCE: 346
aaggcagggc ccccgcuccc c                                              21

<210> SEQ ID NO 347
<211> LENGTH: 23
<212> TYPE: RNA
<213> ORGANISM: Homo sapiens

<400> SEQUENCE: 347
uacccuguag auccgaauuu gug                                            23

<210> SEQ ID NO 348
<211> LENGTH: 20
<212> TYPE: RNA
<213> ORGANISM: Homo sapiens

<400> SEQUENCE: 348
acuggacuug gagccagaag                                                20

<210> SEQ ID NO 349
<211> LENGTH: 23
<212> TYPE: RNA
<213> ORGANISM: Homo sapiens

<400> SEQUENCE: 349
agcucggucu gaggccccuc agu                                            23

<210> SEQ ID NO 350
<211> LENGTH: 21
<212> TYPE: RNA
<213> ORGANISM: Homo sapiens

<400> SEQUENCE: 350
uggacugccc ugaucuggag a                                              21
```

```
<210> SEQ ID NO 351
<211> LENGTH: 20
<212> TYPE: RNA
<213> ORGANISM: Homo sapiens

<400> SEQUENCE: 351
uagaggaagc uguggagaga                                                    20

<210> SEQ ID NO 352
<211> LENGTH: 22
<212> TYPE: RNA
<213> ORGANISM: Homo sapiens

<400> SEQUENCE: 352
aggugcucca ggcuggcuca ca                                                 22

<210> SEQ ID NO 353
<211> LENGTH: 22
<212> TYPE: RNA
<213> ORGANISM: Homo sapiens

<400> SEQUENCE: 353
cugcgcaagc uacugccuug cu                                                 22

<210> SEQ ID NO 354
<211> LENGTH: 20
<212> TYPE: RNA
<213> ORGANISM: Homo sapiens

<400> SEQUENCE: 354
ucugguccug gacaggaggc                                                    20

<210> SEQ ID NO 355
<211> LENGTH: 21
<212> TYPE: RNA
<213> ORGANISM: Homo sapiens

<400> SEQUENCE: 355
uuacacagcu ggacagaggc a                                                  21

<210> SEQ ID NO 356
<211> LENGTH: 23
<212> TYPE: RNA
<213> ORGANISM: Homo sapiens

<400> SEQUENCE: 356
uugggaggga agacagcugg aga                                                23

<210> SEQ ID NO 357
<211> LENGTH: 21
<212> TYPE: RNA
<213> ORGANISM: Homo sapiens

<400> SEQUENCE: 357
gcagggacag caaagggguug c                                                 21

<210> SEQ ID NO 358
<211> LENGTH: 20
<212> TYPE: RNA
<213> ORGANISM: Homo sapiens
```

```
<400> SEQUENCE: 358
guccgcucgg cgguggccca                                         20

<210> SEQ ID NO 359
<211> LENGTH: 23
<212> TYPE: RNA
<213> ORGANISM: Homo sapiens

<400> SEQUENCE: 359
ugagcgccuc gacgacagag ccg                                     23

<210> SEQ ID NO 360
<211> LENGTH: 22
<212> TYPE: RNA
<213> ORGANISM: Homo sapiens

<400> SEQUENCE: 360
uaccauuaga agagcuggaa ga                                      22

<210> SEQ ID NO 361
<211> LENGTH: 18
<212> TYPE: RNA
<213> ORGANISM: Homo sapiens

<400> SEQUENCE: 361
cuggcagggg gagaggua                                           18

<210> SEQ ID NO 362
<211> LENGTH: 23
<212> TYPE: RNA
<213> ORGANISM: Homo sapiens

<400> SEQUENCE: 362
caacggaauc ccaaaagcag cug                                     23

<210> SEQ ID NO 363
<211> LENGTH: 17
<212> TYPE: RNA
<213> ORGANISM: Homo sapiens

<400> SEQUENCE: 363 guggggaga ggcuguc                                             17

<210> SEQ ID NO 364
<211> LENGTH: 23
<212> TYPE: RNA
<213> ORGANISM: Homo sapiens

<400> SEQUENCE: 364
ucccuguccu ccaggagcuc acg                                     23

<210> SEQ ID NO 365
<211> LENGTH: 20
<212> TYPE: RNA
<213> ORGANISM: Homo sapiens

<400> SEQUENCE: 365
ugggaggagg ggaucuuggg                                         20

<210> SEQ ID NO 366
<211> LENGTH: 21
<212> TYPE: RNA
```

<213> ORGANISM: Homo sapiens

<400> SEQUENCE: 366
ucagcuacua ccucuauuag g          21

<210> SEQ ID NO 367
<211> LENGTH: 21
<212> TYPE: RNA
<213> ORGANISM: Homo sapiens

<400> SEQUENCE: 367
aauauaacac agauggccug u          21

<210> SEQ ID NO 368
<211> LENGTH: 22
<212> TYPE: RNA
<213> ORGANISM: Homo sapiens

<400> SEQUENCE: 368
acccuaucaa uauugucucu gc         22

<210> SEQ ID NO 369
<211> LENGTH: 20
<212> TYPE: RNA
<213> ORGANISM: Homo sapiens

<400> SEQUENCE: 369
augcgaggau gcugacagug            20

<210> SEQ ID NO 370
<211> LENGTH: 21
<212> TYPE: RNA
<213> ORGANISM: Homo sapiens

<400> SEQUENCE: 370
uggggguguy gggagagaga g          21

<210> SEQ ID NO 371
<211> LENGTH: 23
<212> TYPE: RNA
<213> ORGANISM: Homo sapiens

<400> SEQUENCE: 371
aggaugagca aagaaaguag auu        23

<210> SEQ ID NO 372
<211> LENGTH: 22
<212> TYPE: RNA
<213> ORGANISM: Homo sapiens

<400> SEQUENCE: 372
ugggucuuug cgggcgagau ga         22

<210> SEQ ID NO 373
<211> LENGTH: 24
<212> TYPE: RNA
<213> ORGANISM: Homo sapiens

<400> SEQUENCE: 373
cagggcucag ggauuggaug gagg       24

<210> SEQ ID NO 374
<211> LENGTH: 20

<212> TYPE: RNA
<213> ORGANISM: Homo sapiens

<400> SEQUENCE: 374
cggggugggu gaggucgggc                                    20

<210> SEQ ID NO 375
<211> LENGTH: 25
<212> TYPE: RNA
<213> ORGANISM: Homo sapiens

<400> SEQUENCE: 375
auggggugag auggggagga gcagc                              25

<210> SEQ ID NO 376
<211> LENGTH: 24
<212> TYPE: RNA
<213> ORGANISM: Homo sapiens

<400> SEQUENCE: 376
acuggcuagg gaaaaugauu ggau                               24

<210> SEQ ID NO 377
<211> LENGTH: 22
<212> TYPE: RNA
<213> ORGANISM: Homo sapiens

<400> SEQUENCE: 377
cacccguaga accgaccuug cg                                 22

<210> SEQ ID NO 378
<211> LENGTH: 23
<212> TYPE: RNA
<213> ORGANISM: Homo sapiens

<400> SEQUENCE: 378
uagcagcggg aacaguucug cag                                23

<210> SEQ ID NO 379
<211> LENGTH: 22
<212> TYPE: RNA
<213> ORGANISM: Homo sapiens

<400> SEQUENCE: 379
aaaaacugag acuacuuuug ca                                 22

<210> SEQ ID NO 380
<211> LENGTH: 22
<212> TYPE: RNA
<213> ORGANISM: Homo sapiens

<400> SEQUENCE: 380 aggggaugg cagagcaaaa uu                                  22

<210> SEQ ID NO 381
<211> LENGTH: 22
<212> TYPE: RNA
<213> ORGANISM: Homo sapiens

<400> SEQUENCE: 381
acucggcgug gcgucggucg ug                                 22

<210> SEQ ID NO 382

```
<211> LENGTH: 22
<212> TYPE: RNA
<213> ORGANISM: Homo sapiens

<400> SEQUENCE: 382
aaaaguaauu gcgguuuuug cc                                              22

<210> SEQ ID NO 383
<211> LENGTH: 21
<212> TYPE: RNA
<213> ORGANISM: Homo sapiens

<400> SEQUENCE: 383
caggcaggug uagguggag c                                                21

<210> SEQ ID NO 384
<211> LENGTH: 23
<212> TYPE: RNA
<213> ORGANISM: Homo sapiens

<400> SEQUENCE: 384
aucagggcuu guggaauggg aag                                             23

<210> SEQ ID NO 385
<211> LENGTH: 22
<212> TYPE: RNA
<213> ORGANISM: Homo sapiens

<400> SEQUENCE: 385
ggggcugggg ccggggccga gc                                              22

<210> SEQ ID NO 386
<211> LENGTH: 17
<212> TYPE: RNA
<213> ORGANISM: Homo sapiens

<400> SEQUENCE: 386
cuccgggacg gcugggc                                                    17

<210> SEQ ID NO 387
<211> LENGTH: 22
<212> TYPE: RNA
<213> ORGANISM: Homo sapiens

<400> SEQUENCE: 387
gaauguugcu cggugaaccc cu                                              22

<210> SEQ ID NO 388
<211> LENGTH: 23
<212> TYPE: RNA
<213> ORGANISM: Homo sapiens

<400> SEQUENCE: 388
agaggcuuug ugcggauacg ggg                                             23

<210> SEQ ID NO 389
<211> LENGTH: 22
<212> TYPE: RNA
<213> ORGANISM: Homo sapiens

<400> SEQUENCE: 389
uuucuucuua gacauggcaa cg                                              22
```

```
<210> SEQ ID NO 390
<211> LENGTH: 23
<212> TYPE: RNA
<213> ORGANISM: Homo sapiens

<400> SEQUENCE: 390
ugaguggggc ucccgggacg gcg                                          23

<210> SEQ ID NO 391
<211> LENGTH: 26
<212> TYPE: RNA
<213> ORGANISM: Homo sapiens

<400> SEQUENCE: 391
cucggccgcg gcgcguagcc cccgcc                                       26

<210> SEQ ID NO 392
<211> LENGTH: 21
<212> TYPE: RNA
<213> ORGANISM: Homo sapiens

<400> SEQUENCE: 392
cagcagcaca cugugguuug u                                            21

<210> SEQ ID NO 393
<211> LENGTH: 22
<212> TYPE: RNA
<213> ORGANISM: Homo sapiens

<400> SEQUENCE: 393
aaagaucugg aagugggaga ca                                           22

<210> SEQ ID NO 394
<211> LENGTH: 23
<212> TYPE: RNA
<213> ORGANISM: Homo sapiens

<400> SEQUENCE: 394
aucaacagac auuaauuggg cgc                                          23

<210> SEQ ID NO 395
<211> LENGTH: 22
<212> TYPE: RNA
<213> ORGANISM: Homo sapiens

<400> SEQUENCE: 395
uaugucugcu gaccaucacc uu                                           22

<210> SEQ ID NO 396
<211> LENGTH: 23
<212> TYPE: RNA
<213> ORGANISM: Homo sapiens

<400> SEQUENCE: 396
agcuucuuua cagugcugcc uug                                          23

<210> SEQ ID NO 397
<211> LENGTH: 22
<212> TYPE: RNA
<213> ORGANISM: Homo sapiens

<400> SEQUENCE: 397
cuuggcaccu agcaagcacu ca                                           22
```

```
<210> SEQ ID NO 398
<211> LENGTH: 17
<212> TYPE: RNA
<213> ORGANISM: Homo sapiens

<400> SEQUENCE: 398
acauugccag ggaguuu                                                  17

<210> SEQ ID NO 399
<211> LENGTH: 23
<212> TYPE: RNA
<213> ORGANISM: Homo sapiens

<400> SEQUENCE: 399
cugacugaau agguaggguc auu                                           23

<210> SEQ ID NO 400
<211> LENGTH: 22
<212> TYPE: RNA
<213> ORGANISM: Homo sapiens

<400> SEQUENCE: 400
gcccaggacu uugugcgggg ug                                            22

<210> SEQ ID NO 401
<211> LENGTH: 23
<212> TYPE: RNA
<213> ORGANISM: Homo sapiens

<400> SEQUENCE: 401
uucauuuggu auaaaccgcg auu                                           23

<210> SEQ ID NO 402
<211> LENGTH: 23
<212> TYPE: RNA
<213> ORGANISM: Homo sapiens

<400> SEQUENCE: 402
aguuuugcag guuugcaucc agc                                           23

<210> SEQ ID NO 403
<211> LENGTH: 22
<212> TYPE: RNA
<213> ORGANISM: Homo sapiens

<400> SEQUENCE: 403
aaaaccgucu aguuacaguu gu                                            22

<210> SEQ ID NO 404
<211> LENGTH: 17
<212> TYPE: RNA
<213> ORGANISM: Homo sapiens

<400> SEQUENCE: 404
agggugugug uguuuuu                                                  17

<210> SEQ ID NO 405
<211> LENGTH: 21
<212> TYPE: RNA
<213> ORGANISM: Homo sapiens

<400> SEQUENCE: 405
uuaagacuug cagugauguu u                                             21
```

```
<210> SEQ ID NO 406
<211> LENGTH: 22
<212> TYPE: RNA
<213> ORGANISM: Homo sapiens

<400> SEQUENCE: 406
gcuggugcaa aaguaauggc gg                                                  22

<210> SEQ ID NO 407
<211> LENGTH: 22
<212> TYPE: RNA
<213> ORGANISM: Homo sapiens

<400> SEQUENCE: 407
aaacaaacau ggugcacuuc uu                                                  22

<210> SEQ ID NO 408
<211> LENGTH: 22
<212> TYPE: RNA
<213> ORGANISM: Homo sapiens

<400> SEQUENCE: 408
agugggaggc cagggcacgg ca                                                  22

<210> SEQ ID NO 409
<211> LENGTH: 17
<212> TYPE: RNA
<213> ORGANISM: Homo sapiens

<400> SEQUENCE: 409
ggauggagga ggggucu                                                        17

<210> SEQ ID NO 410
<211> LENGTH: 19
<212> TYPE: RNA
<213> ORGANISM: Homo sapiens

<400> SEQUENCE: 410
acuggacuug gagucagga                                                      19

<210> SEQ ID NO 411
<211> LENGTH: 20
<212> TYPE: RNA
<213> ORGANISM: Homo sapiens

<400> SEQUENCE: 411
agcccccugg ccccaaaccc                                                     20

<210> SEQ ID NO 412
<211> LENGTH: 22
<212> TYPE: RNA
<213> ORGANISM: Homo sapiens

<400> SEQUENCE: 412
aaguucuguu auacacucag gc                                                  22

<210> SEQ ID NO 413
<211> LENGTH: 18
<212> TYPE: RNA
<213> ORGANISM: Homo sapiens
```

<400> SEQUENCE: 413
cagccccaca gccucaga                                          18

<210> SEQ ID NO 414
<211> LENGTH: 21
<212> TYPE: RNA
<213> ORGANISM: Homo sapiens

<400> SEQUENCE: 414
ugagcuaaau gugugcuggg a                                      21

<210> SEQ ID NO 415
<211> LENGTH: 19
<212> TYPE: RNA
<213> ORGANISM: Homo sapiens

<400> SEQUENCE: 415
cggcgcgacc ggcccgggg                                         19

<210> SEQ ID NO 416
<211> LENGTH: 23
<212> TYPE: RNA
<213> ORGANISM: Homo sapiens

<400> SEQUENCE: 416
gggggggcag gaggggcuca ggg                                    23

<210> SEQ ID NO 417
<211> LENGTH: 22
<212> TYPE: RNA
<213> ORGANISM: Homo sapiens

<400> SEQUENCE: 417
uauacaaggg caagcucucu gu                                     22

<210> SEQ ID NO 418
<211> LENGTH: 22
<212> TYPE: RNA
<213> ORGANISM: Homo sapiens

<400> SEQUENCE: 418
ugagggcucc aggugacggu gg                                     22

<210> SEQ ID NO 419
<211> LENGTH: 22
<212> TYPE: RNA
<213> ORGANISM: Homo sapiens

<400> SEQUENCE: 419
uuugcaguaa caggugugag ca                                     22

<210> SEQ ID NO 420
<211> LENGTH: 21
<212> TYPE: RNA
<213> ORGANISM: Homo sapiens

<400> SEQUENCE: 420
aggcaagaug cuggcauagc u                                      21

<210> SEQ ID NO 421
<211> LENGTH: 21
<212> TYPE: RNA

<213> ORGANISM: Homo sapiens

<400> SEQUENCE: 421
aagggacagg gaggucgug g                                              21

<210> SEQ ID NO 422
<211> LENGTH: 22
<212> TYPE: RNA
<213> ORGANISM: Homo sapiens

<400> SEQUENCE: 422
cacuggcucc uuucugggua ga                                            22

<210> SEQ ID NO 423
<211> LENGTH: 21
<212> TYPE: RNA
<213> ORGANISM: Homo sapiens

<400> SEQUENCE: 423 gcgugggc cggagggcg u                                                21

<210> SEQ ID NO 424
<211> LENGTH: 22
<212> TYPE: RNA
<213> ORGANISM: Homo sapiens

<400> SEQUENCE: 424
uauaaaauga gggcaguaag ac                                            22

<210> SEQ ID NO 425
<211> LENGTH: 23
<212> TYPE: RNA
<213> ORGANISM: Homo sapiens

<400> SEQUENCE: 425
cuggagauau ggaagagcug ugu                                           23

<210> SEQ ID NO 426
<211> LENGTH: 22
<212> TYPE: RNA
<213> ORGANISM: Homo sapiens

<400> SEQUENCE: 426
agacacauuu ggagagggac cc                                            22

<210> SEQ ID NO 427
<211> LENGTH: 22
<212> TYPE: RNA
<213> ORGANISM: Homo sapiens

<400> SEQUENCE: 427
cugcaaugua agcacuucuu ac                                            22

<210> SEQ ID NO 428
<211> LENGTH: 23
<212> TYPE: RNA
<213> ORGANISM: Homo sapiens

<400> SEQUENCE: 428
uugggauggu aggaccagag ggg                                           23

<210> SEQ ID NO 429
<211> LENGTH: 21

```
<212> TYPE: RNA
<213> ORGANISM: Homo sapiens

<400> SEQUENCE: 429
ugagaugaag cacuguagcu c                                       21

<210> SEQ ID NO 430
<211> LENGTH: 17
<212> TYPE: RNA
<213> ORGANISM: Homo sapiens

<400> SEQUENCE: 430
aagacugaga ggaggga                                            17

<210> SEQ ID NO 431
<211> LENGTH: 23
<212> TYPE: RNA
<213> ORGANISM: Homo sapiens

<400> SEQUENCE: 431
gagggcagcg uggguguggc gga                                     23

<210> SEQ ID NO 432
<211> LENGTH: 22
<212> TYPE: RNA
<213> ORGANISM: Homo sapiens

<400> SEQUENCE: 432
aaaaguaauu gugguuuuug cc                                      22

<210> SEQ ID NO 433
<211> LENGTH: 22
<212> TYPE: RNA
<213> ORGANISM: Homo sapiens

<400> SEQUENCE: 433
uguguggauc cuggaggagg ca                                      22

<210> SEQ ID NO 434
<211> LENGTH: 21
<212> TYPE: RNA
<213> ORGANISM: Homo sapiens

<400> SEQUENCE: 434
acggcccagg cggcauuggu g                                       21

<210> SEQ ID NO 435
<211> LENGTH: 20
<212> TYPE: RNA
<213> ORGANISM: Homo sapiens

<400> SEQUENCE: 435
ucacaccugc cucgccccc                                          20

<210> SEQ ID NO 436
<211> LENGTH: 22
<212> TYPE: RNA
<213> ORGANISM: Homo sapiens

<400> SEQUENCE: 436
ugugacuggu ugaccagagg gg                                      22

<210> SEQ ID NO 437
```

```
<210> SEQ ID NO 437
<211> LENGTH: 20
<212> TYPE: RNA
<213> ORGANISM: Homo sapiens

<400> SEQUENCE: 437
ucucuucauc uaccccccag                                                    20

<210> SEQ ID NO 438
<211> LENGTH: 22
<212> TYPE: RNA
<213> ORGANISM: Homo sapiens

<400> SEQUENCE: 438
ucggccugac cacccacccc ac                                                 22

<210> SEQ ID NO 439
<211> LENGTH: 22
<212> TYPE: RNA
<213> ORGANISM: Homo sapiens

<400> SEQUENCE: 439
guguggaaga ugggaggaga aa                                                 22

<210> SEQ ID NO 440
<211> LENGTH: 21
<212> TYPE: RNA
<213> ORGANISM: Homo sapiens

<400> SEQUENCE: 440
caagucacua gugguuccgu u                                                  21

<210> SEQ ID NO 441
<211> LENGTH: 20
<212> TYPE: RNA
<213> ORGANISM: Homo sapiens

<400> SEQUENCE: 441
ugggcugcug agaaggggca                                                    20

<210> SEQ ID NO 442
<211> LENGTH: 23
<212> TYPE: RNA
<213> ORGANISM: Homo sapiens

<400> SEQUENCE: 442
ucaggcaaag ggauauuuac aga                                                23

<210> SEQ ID NO 443
<211> LENGTH: 22
<212> TYPE: RNA
<213> ORGANISM: Homo sapiens

<400> SEQUENCE: 443
uuggggaaac ggccgcugag ug                                                 22

<210> SEQ ID NO 444
<211> LENGTH: 22
<212> TYPE: RNA
<213> ORGANISM: Homo sapiens

<400> SEQUENCE: 444
aacccguaga uccgaacuug ug                                                 22
```

```
<210> SEQ ID NO 445
<211> LENGTH: 19
<212> TYPE: RNA
<213> ORGANISM: Homo sapiens

<400> SEQUENCE: 445
accgugcaaa gguagcaua                                                19

<210> SEQ ID NO 446
<211> LENGTH: 21
<212> TYPE: RNA
<213> ORGANISM: Homo sapiens

<400> SEQUENCE: 446
uugccagggc aggaggugga a                                             21

<210> SEQ ID NO 447
<211> LENGTH: 21
<212> TYPE: RNA
<213> ORGANISM: Homo sapiens

<400> SEQUENCE: 447
cccaugccuc cugccgcggu c                                             21

<210> SEQ ID NO 448
<211> LENGTH: 22
<212> TYPE: RNA
<213> ORGANISM: Homo sapiens

<400> SEQUENCE: 448
cucaaguagu cugaccaggg ga                                            22

<210> SEQ ID NO 449
<211> LENGTH: 17
<212> TYPE: RNA
<213> ORGANISM: Homo sapiens

<400> SEQUENCE: 449
ucgccuccuc cucuccc                                                  17

<210> SEQ ID NO 450
<211> LENGTH: 20
<212> TYPE: RNA
<213> ORGANISM: Homo sapiens

<400> SEQUENCE: 450
ggcggcgggg agguaggcag                                               20

<210> SEQ ID NO 451
<211> LENGTH: 22
<212> TYPE: RNA
<213> ORGANISM: Homo sapiens

<400> SEQUENCE: 451 gggggugug gagccagggg gc                                             22

<210> SEQ ID NO 452
<211> LENGTH: 22
<212> TYPE: RNA
<213> ORGANISM: Homo sapiens

<400> SEQUENCE: 452
aguauucugu accagggaag gu                                            22
```

```
<210> SEQ ID NO 453
<211> LENGTH: 21
<212> TYPE: RNA
<213> ORGANISM: Homo sapiens

<400> SEQUENCE: 453
uaacagucuc cagucacggc c                                              21

<210> SEQ ID NO 454
<211> LENGTH: 22
<212> TYPE: RNA
<213> ORGANISM: Homo sapiens

<400> SEQUENCE: 454
cagcagggga gagagaggag uc                                             22

<210> SEQ ID NO 455
<211> LENGTH: 20
<212> TYPE: RNA
<213> ORGANISM: Homo sapiens

<400> SEQUENCE: 455
uaggaugggg gugagaggug                                                20

<210> SEQ ID NO 456
<211> LENGTH: 23
<212> TYPE: RNA
<213> ORGANISM: Homo sapiens

<400> SEQUENCE: 456
aacauucauu guugucggug ggu                                            23

<210> SEQ ID NO 457
<211> LENGTH: 23
<212> TYPE: RNA
<213> ORGANISM: Homo sapiens

<400> SEQUENCE: 457
gaguggauag gggagugugu gga                                            23

<210> SEQ ID NO 458
<211> LENGTH: 22
<212> TYPE: RNA
<213> ORGANISM: Homo sapiens

<400> SEQUENCE: 458
cugguacagg ccuggggggac ag                                            22

<210> SEQ ID NO 459
<211> LENGTH: 22
<212> TYPE: RNA
<213> ORGANISM: Homo sapiens

<400> SEQUENCE: 459
cugguuucac augguggcuu ag                                             22

<210> SEQ ID NO 460
<211> LENGTH: 21
<212> TYPE: RNA
<213> ORGANISM: Homo sapiens

<400> SEQUENCE: 460
aguggaccga ggaaggaagg a                                              21
```

```
<210> SEQ ID NO 461
<211> LENGTH: 23
<212> TYPE: RNA
<213> ORGANISM: Homo sapiens

<400> SEQUENCE: 461
ucuuggagua ggucauuggg ugg                                        23

<210> SEQ ID NO 462
<211> LENGTH: 22
<212> TYPE: RNA
<213> ORGANISM: Homo sapiens

<400> SEQUENCE: 462
ucggauccgu cugagcuugg cu                                         22

<210> SEQ ID NO 463
<211> LENGTH: 16
<212> TYPE: RNA
<213> ORGANISM: Homo sapiens

<400> SEQUENCE: 463
aggaaacagg gaccca                                                16

<210> SEQ ID NO 464
<211> LENGTH: 19
<212> TYPE: RNA
<213> ORGANISM: Homo sapiens

<400> SEQUENCE: 464
ggcuugcaug ggggacugg                                             19

<210> SEQ ID NO 465
<211> LENGTH: 23
<212> TYPE: RNA
<213> ORGANISM: Homo sapiens

<400> SEQUENCE: 465
uggugggugg ggaggagaag ugc                                        23

<210> SEQ ID NO 466
<211> LENGTH: 22
<212> TYPE: RNA
<213> ORGANISM: Homo sapiens

<400> SEQUENCE: 466
aagacgggag gaaagaaggg ag                                         22

<210> SEQ ID NO 467
<211> LENGTH: 23
<212> TYPE: RNA
<213> ORGANISM: Homo sapiens

<400> SEQUENCE: 467
aucccuugca ggggcuguug ggu                                        23

<210> SEQ ID NO 468
<211> LENGTH: 19
<212> TYPE: RNA
<213> ORGANISM: homo sapiens
```

```
<400> SEQUENCE: 468
acauuuucca gcccauuca                                            19

<210> SEQ ID NO 469
<211> LENGTH: 24
<212> TYPE: RNA
<213> ORGANISM: homo sapiens

<400> SEQUENCE: 469
uguggacagu gagguagagg gagu                                      24

<210> SEQ ID NO 470
<211> LENGTH: 23
<212> TYPE: RNA
<213> ORGANISM: homo sapiens

<400> SEQUENCE: 470
cgcgggcgcu ccuggccgcc gcc                                       23

<210> SEQ ID NO 471
<211> LENGTH: 21
<212> TYPE: RNA
<213> ORGANISM: homo sapiens

<400> SEQUENCE: 471
gcgacccaua cuugguuuca g                                         21

<210> SEQ ID NO 472
<211> LENGTH: 18
<212> TYPE: RNA
<213> ORGANISM: homo sapiens

<400> SEQUENCE: 472
aggagaaguc gggaaggu                                             18

<210> SEQ ID NO 473
<211> LENGTH: 22
<212> TYPE: RNA
<213> ORGANISM: homo sapiens

<400> SEQUENCE: 473
uccgaacucu ccauccucu gc                                         22

<210> SEQ ID NO 474
<211> LENGTH: 21
<212> TYPE: RNA
<213> ORGANISM: homo sapiens

<400> SEQUENCE: 474
cuuccgcccc gccgggcguc g                                         21

<210> SEQ ID NO 475
<211> LENGTH: 20
<212> TYPE: RNA
<213> ORGANISM: homo sapiens

<400> SEQUENCE: 475
cgguggacug gaguggugg                                            20
```